US011993632B2

United States Patent
Chan et al.

(10) Patent No.: US 11,993,632 B2
(45) Date of Patent: May 28, 2024

(54) COMPOSITIONS AND METHODS FOR MODULATING INFLAMMATORY RESPONSES

(71) Applicants: Duke University, Durham, NC (US); University of Massachusetts, Boston, MA (US)

(72) Inventors: Francis Chan, Durham, NC (US); Himani Nailwal, Durham, NC (US)

(73) Assignees: Duke University, Durham, NC (US); University of Massachusetts, Boston, MA (US)

( * ) Notice: Subject to any disclaimer, the term of this patent is extended or adjusted under 35 U.S.C. 154(b) by 132 days.

(21) Appl. No.: 16/874,804

(22) Filed: May 15, 2020

(65) Prior Publication Data
US 2020/0361998 A1    Nov. 19, 2020

Related U.S. Application Data

(60) Provisional application No. 62/848,255, filed on May 15, 2019.

(51) Int. Cl.
| | | |
|---|---|---|
| *A61K 38/16* | (2006.01) | |
| *A61P 37/02* | (2006.01) | |
| *C07K 14/005* | (2006.01) | |
| *C12N 7/00* | (2006.01) | |
| *A61K 38/00* | (2006.01) | |

(52) U.S. Cl.
CPC ............ *C07K 14/005* (2013.01); *A61P 37/02* (2018.01); *C12N 7/00* (2013.01); *A61K 38/00* (2013.01); *C12N 2710/24122* (2013.01); *C12N 2710/24132* (2013.01)

(58) Field of Classification Search
None
See application file for complete search history.

(56) References Cited

PUBLICATIONS

NCBI GenBAnk entry AAM13662.1 (uploaded 2006).*
Hawkins, P. T. and Stephens, L. R.; "PI3K signalling in inflammation." Biochim. Biophys. Acta (2015) 1851 p. 882-897.*
Liu, Ting et al; "NF-kb signaling in inflammation." Signal Transduction and Targeted Therapy (2017) 2 e17023.*
Reynolds, Fred et al; "A functional proteomic method for biomarker discovery." PLoS One (2011) 6(7) e22471.*
Bhattacharya, Roshni et al; "Impact of genetic variation on three diminsional structure and function of proteins." PLoS One (2017) 12(3) e0171355.*
Yampolsky, Lev Y. and Stoltzfus, Arlin; "The exchangeability of amino acids in proteins." Genetics (2005) 170 p. 1459-1472.*
medical-dictionary.thefreedictionary.com/ankyrin+repeat, downloaded Mar. 16, 2022.*
Howes, Laura "Deepmine ai predicts protein structures." C&EN (2020).*
Mohamed, Mohamed R. et al, "Proteomic screening of variola virus reveals a unique nf-kb inhibitor that is highly conserved among pahtogenic orthopoxviruses." PNAS (2009) 106(22) p. 9045-9050.*
Genbank entry AAA60932 (1995).*
Zhang, Bin and Peng, Zheng-Yu; "A minimum folding unit in the ankyrin repeat protein p16ink4." J. Mol. Biol. (2000) 299 p. 1121-1132.*
NCBI sequence P42771, available 1995.*
Liu, Zhijun et al; "A class of viral inducer of degradation of the necroptosis adaptor ripk3 regulates virus induced inflammation." Immunity (2021) 54 p. 247-258.*
Mauldin, Mathew R. et al; "Cowpox virus: what's in a name." Viruses (2017) 9(101).*
GenBank entry QEM25151, available

(56) References Cited

PUBLICATIONS

Mohamed et al., Cowpox virus expresses a novel ankyrin repeat NF-kappaB inhibitor that controls inflammatory cell influx into virus-infected tissues and is critical for virus pathogenesis. J Virol. Sep. 2009;83(18):9223-36.

Moriwaki et al., Distinct Kinase-Independent Role of RIPK3 in CD11c + Mononuclear Phagocytes in Cytokine-Induced Tissue Repair. Cell Rep. Mar. 7, 2017;18(10):2441-2451.

Myskiw et al., Vaccinia virus E3 suppresses expression of diverse cytokines through inhibition of the PKR, NF-kappaB, and IRF3 pathways. J Virol. Jul. 2009;83(13):6757-68.

Nailwal et al., Necroptosis in anti-viral inflammation. Cell Death Differ. Jan. 2019;26(1):4-13.

Petrie et al., Viral MLKL Homologs Subvert Necroptotic Cell Death by Sequestering Cellular RIPK3. Cell Rep. Sep. 24, 2019;28(13):3309-3319.e5.

Polykratis et al., Cutting edge: RIPK1 Kinase inactive mice are viable and protected from TNF-induced necroptosis in vivo. J Immunol. Aug. 15, 2014;193(4):1539-1543.

Sanchez-Sampedro et al., The evolution of poxvirus vaccines. Viruses. Apr. 7, 2015;7(4):1726-803.

Satheshkumar et al., Inhibition of the ubiquitin-proteasome system prevents vaccinia virus DNA replication and expression of intermediate and late genes. J Virol. Mar. 2009;83(6):2469-79.

Sumner et al., Vaccinia virus inhibits NF-κB-dependent gene expression downstream of p65 translocation. J Virol. Mar. 2014;88(6):3092-102.

Teale et al., Orthopoxviruses require a functional ubiquitin-proteasome system for productive replication. J Virol. Mar. 2009;83(5):2099-108.

Weir et al., Regulation of expression and nucleotide sequence of a late vaccinia virus gene. J Virol. Sep. 1984;51(3):662-9.

Mosavi et al., "The ankyrin repeat as molecular architecture for protein recognition" Protein Science (2004), 13:1435-1448.

Bratke et al., A survey of host range genes in poxvirus genomes. Infect Genet Evol. Mar. 2013;14:406-25.

Chan et al., Programmed necrosis in the cross talk of cell death and inflammation. Annu Rev Immunol. 2015;33:79-106.

Dondelinger et al., An evolutionary perspective on the necroptotic pathway. Trends Cell Biol. Oct. 2016;26(10):721-732.

Guo et al., Herpes simplex virus suppresses necroptosis in human cells. Cell Host Microbe. Feb. 11, 2015;17(2):243-51.

Holler et al., Fas triggers an alternative, caspase-8-independent cell death pathway using the kinase RIP as effector molecule. Nat Immunol. Dec. 2000;1(6):489-95.

Huang et al., RIP1/RIP3 binding to HSV-1 ICP6 initiates necroptosis to restrict virus propagation in mice. Cell Host Microbe. Feb. 11, 2015;17(2):229-42.

Li et al., Induction of necrotic-like cell death by tumor necrosis factor alpha and caspase inhibitors: novel mechanism for killing virus-infected cells. J Virol. Aug. 2000;74(16):7470-7.

Meylan et al., RIP1 is an essential mediator of Toll-like receptor 3-induced NF-kappa B activation. Nat Immunol. May 2004;5(5):503-7.

Mocarski et al., Necroptosis: The Trojan horse in cell autonomous antiviral host defense. Virology. May 2015;479-480:160-6.

Mohamed et al., Proteomic screening of variola virus reveals a unique NF-kappaB inhibitor that is highly conserved among pathogenic orthopoxviruses. Proc Natl Acad Sci U S A. Jun. 2, 2009;106(22):9045-50.

Sun et al., Identification of a novel homotypic interaction motif required for the phosphorylation of receptor-interacting protein (RIP) by RIP3. J Biol Chem. Mar. 15, 2002;277(11):9505-11.

Sun et al., RIP3, a novel apoptosis-inducing kinase. J Biol Chem. Jun. 11, 1999;274(24):16871-5.

Upton et al., DAI/ZBP1/DLM-1 complexes with RIP3 to mediate virus-induced programmed necrosis that is targeted by murine cytomegalovirus vIRA. Cell Host Microbe. Mar. 15, 2012;11(3):290-7.

Upton et al., Staying alive: cell death in antiviral immunity. Mol Cell. Apr. 24, 2014;54(2):273-80.

Upton et al., Virus inhibition of RIP3-dependent necrosis. Cell Host Microbe. Apr. 22, 2010;7(4):302-313.

Yu et al., Herpes Simplex Virus 1 (HSV-1) and HSV-2 Mediate Species-Specific Modulations of Programmed Necrosis through the Viral Ribonucleotide Reductase Large Subunit R1. J Virol. Nov. 11, 2015;90(2):1088-95.

\* cited by examiner

COMPOSITIONS AND METHODS FOR MODULATING INFLAMMATORY RESPONSES

CROSS REFERENCE TO RELATED APPLICATIONS

This application claims priority to and the benefit of U.S. Provisional Patent Application No. 62/848,255 filed May 15, 2019, which is incorporated herein by reference in its entirety and for all purposes.

GOVERNMENT FUNDING

This invention was made with government support under grant number R21 AI128197 awarded by the National Institute of Allergy and Infectious Diseases, and grant number 5R01AI48302-02 awarded by the National Institutes of Health. The government has certain rights to this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 62,000 Byte ASCII (Text) file named "38488-202_ST25" created on May 15, 2020.

FIELD

The present disclosure provides compositions and methods related to the modulation of the inflammation response activated by a host's immune system. In particular, the present disclosure provides novel inhibitors of proteins that exhibit pro-inflammatory activity (e.g., RIPK1, RIPK3, ZBP1, TRIF, CUL1, SKP1, and NF-κB, among others), as well as corresponding therapeutic compositions and methods of treatment using these inhibitors.

BACKGROUND

Interference of the host immune response is critical in determining the fitness and pathogenicity of viruses. Evasion of host cell death is a common strategy used by viruses to facilitate their replication within the host. While apoptosis is tolerogenic, lytic cell death is widely believed to promote anti-viral inflammation. Large DNA viruses in the herpesvirus and poxvirus families are adept at subverting host cell apoptosis. Inhibition of apoptosis can prime the infected cells to lytic cell death such as necroptosis, an inflammatory form of cell death mediated by the serine/threonine kinase RIPK3 and its downstream effector mixed lineage kinase domain-like (MLKL). Caspase 8 cleaves and inactivates the necroptosis adaptors RIPK1 and RIPK3. Thus, optimal induction of necroptosis requires caspase 8 inhibition. The orthopoxvirus vaccinia virus encodes the CrmA-like orthologue B13R/Spi2 to inhibit caspase 8 and sensitize the infected cells to necroptosis. Mice that are deficient in necroptosis failed to control vaccinia virus (VACV) replication and often succumbed to the infection.

In contrast to VACV, herpesviruses such as murine cytomegalovirus (MCMV), herpes simplex virus 1 (HSV1) and HSV2 encode inhibitors that block both caspase-dependent apoptosis and RIP kinase-mediated necroptosis. In these herpesviruses, the viral inhibitors encode "RIP homotypic interaction motif" (RHIM) that mediates binding to and sequestration of RIPK3 and another necroptosis adaptor ZBP1. Hence, unlike VACV, apoptosis and necroptosis are both inhibited in these herpesviruses. As such, despite the wide acceptance of necroptosis as an anti-viral host response, VACV remains the only example in which necroptosis plays a role in host response and viral pathogenesis.

The primary function of the immune system is to protect the host from invading pathogens. In response, microbial pathogens such as VACV and MCMV have developed various strategies to evade detection and destruction by the immune system. This tug-of-war between the host and the pathogen is a powerful force that shapes organismal evolution. Regulated cell death (RCD) is a host response that limits the reservoir for intracellular pathogens such as viruses. Since pathogen-specific T cell and B cell responses typically take several days and is therefore slow-developing, RCD of infected cells during the first few days of the infection is critical for organismal survival. This innate immune response not only restricts viral replication, but also serves to promote anti-viral inflammation through cell death-associated release of damage-associated molecular patterns (DAMPs). In recent years, necroptosis has been recognized as an important response against many viruses. The central adaptor for necroptosis, RIPK3, also exerts anti-viral effects through cell death-independent activities such as promoting cytokine gene expression.

Viral decoys and inhibitors target the host inflammatory response to evade immune detection. For example, poxvirus encode soluble TNF receptor to neutralize the anti-viral effects of TNF. Using a similar strategy, Enbrel, a soluble TNF receptor 2 decoy, has been highly successful in treating a wide range of inflammatory diseases including rheumatoid arthritis, Crohn's disease and psoriasis. Thus, variants of viral immune inhibitors hold promise as therapeutic options in many autoinflammatory diseases.

SUMMARY

Embodiments of the present disclosure include a recombinant polypeptide inhibitor of at least one inflammatory-modulating protein comprising a plurality of Ankyrin repeat motifs and at least 65% sequence identity with SEQ ID NO: 1. In some embodiments, the polypeptide comprises at least 85% sequence identity with SEQ ID NO: 1. In some embodiments, the polypeptide comprises at least 90% sequence identity with SEQ ID NO: 1.

In some embodiments, the polypeptide comprises between 2 and 6 Ankyrin repeat motifs. In some embodiments, the polypeptide comprises at least 5 Ankyrin repeat motifs.

In some embodiments, the polypeptide is derived from a poxvirus polypeptide. In some embodiments, the poxvirus is a cowpox virus, a ectromelia virus, a monkeypox virus, a variola virus (smallpox), a horsepox virus, a skunkpox virus, a taterapox virus, a camelpox virus, or a volepox virus.

In some embodiments, the polypeptide comprises any one of SEQ ID NOs: 1-4. In some embodiments, the polypeptide comprises any one of SEQ ID NOs: 5-12. In some embodiments, the polypeptide comprises less than 100% sequence identity with any one of SEQ ID NOs: 1 and 5-12. In some embodiments, the polypeptide comprises at least one amino acid substitution that is not present in any one of SEQ ID NOs: 1 and 5-12.

In some embodiments, the inflammatory-modulating protein is one or more of receptor interacting protein kinase-1 (RIPK1), receptor interacting protein kinases-3 (RIPK3), TIR-domain-containing adapter-inducing interferon-β

(TRIF), Z-DNA binding protein 1 (ZBP1), Cullin-1 (CUL1), and/or S-phase kinase associated protein 1 (SKP1). In some embodiments, the polypeptide binds to one or more of RIPK1, RIPK3, TRIF, ZBP1, CUL1, and/or SKP1.

Embodiments of the present disclosure also include a nucleic acid molecule encoding any of the polypeptides described above. Embodiments of the present disclosure also include a vector comprising this nucleic acid molecule.

Embodiments of the present disclosure include a pharmaceutical composition comprising a recombinant polypeptide inhibitor of at least one inflammatory-modulating protein comprising a plurality of Ankyrin repeat motifs and at least 65% sequence identity with SEQ ID NO: 1, and a pharmaceutically acceptable carrier or excipient. In accordance with these embodiments, administration of the composition treats an inflammatory disease or condition.

In some embodiments, the polypeptide comprises at least 85% sequence identity with SEQ ID NO: 1. In some embodiments, the polypeptide comprises at least 5 Ankyrin repeat motifs. In some embodiments, the polypeptide is derived from a poxvirus polypeptide. In some embodiments, the polypeptide comprises any one of SEQ ID NOs: 1-12.

In some embodiments, the inflammatory-modulating protein is one or more of receptor interacting protein kinase-1 (RIPK1), receptor interacting protein kinases-3 (RIPK3), TIR-domain-containing adapter-inducing interferon-β (TRIF), Z-DNA binding protein 1 (ZBP1), Cullin-1 (CUL1), and/or S-phase kinase associated protein 1 (SKP1).

Embodiments of the present disclosure include a method of modulating an immune response in a subject in need thereof that includes administering a recombinant polypeptide inhibitor of at least one inflammatory-modulating protein comprising a plurality of Ankyrin repeat motifs and at least 65% sequence identity with SEQ ID NO: 1. In accordance with these embodiments, inhibition of the at least one inflammatory-modulating protein modulates the immune response in the subject.

In some embodiments, the polypeptide comprises at least 85% sequence identity with SEQ ID NO: 1. In some embodiments, the polypeptide comprises at least 5 Ankyrin repeat motifs. In some embodiments, the polypeptide is derived from a poxvirus polypeptide. In some embodiments, the polypeptide comprises any one of SEQ ID NOs: 1-12.

In some embodiments, the inflammatory-modulating protein is one or more of receptor interacting protein kinase-1 (RIPK1), receptor interacting protein kinases-3 (RIPK3), TIR-domain-containing adapter-inducing interferon-β (TRIF), Z-DNA binding protein 1 (ZBP1), Cullin-1 (CUL1), and/or S-phase kinase associated protein 1 (SKP1).

In some embodiments, modulating the immune response in the subject comprises enhancing expression and/or activity of one or more genes selected from the group consisting of: C-C motif chemokine ligand 2 (Ccl2), C-C motif chemokine ligand 4 (Ccl4), C-X-C motif chemokine ligand 1 (Cxcl1), C-X-C motif chemokine ligand 2 (Cxcl2), and Interleukin 6 (Il6).

In some embodiments, modulating the immune response in the subject comprises attenuating expression and/or activity of one or more genes selected from the group consisting of: C-C motif chemokine ligand 8 (Ccl8), Arachidonate 15-lipoxygenase (Alox15), Complement C3 (C3), Prostaglandin-endoperoxide synthase 1 (Ptgs1), and Arginase 1 (Argl).

In some embodiments, modulating the immune response in the subject comprises inhibiting expression of at least one gene controlled by Nuclear Factor kappa B (NF-κB).

In some embodiments, modulating the immune response in the subject treats at least one inflammatory symptom associated with an autoinflammatory disease.

In some embodiments, the autoinflammatory disease is selected from the group consisting of: rheumatoid arthritis, inflammatory bowel disease, skin inflammation, atopic dermatitis, and systemic lupus erythematosus.

Other aspects and embodiments of the disclosure will be apparent in light of the following detailed description.

BRIEF DESCRIPTION OF THE DRAWINGS

FIGS. 1A-1F: CPXV confers resistance to necroptosis through proteasome-mediated RIPK3 degradation. (A) MEFs infected with the indicated viruses or uninfected (UI) MEFs were stimulated with 10 ng/ml of mTNF for 16 hours. Cell death was determined by propidium iodide staining and flow cytometry. (B) L929 cells were infected with the indicated viruses for 18 hours and the expression of the indicated proteins were determined by Western blot. (C) L929 cells were infected with CPXV (moi=2) for the indicated amount of time. RIPK3 and HSP90 expression was determined by Western blot. (D) CPXV-infected L929 cells were treated with the indicated protease inhibitors. RIPK3 expression was determined by Western blot 6 hours post-infection. (E) L929 cells infected with CPXV were treated with AraC or MG132. RIPK3 expression was determined by Western blot. (F) RIPK3 was purified by immunoprecipitation from CPXV infected or uninfected L929 cells. K48-linked RIPK3 ubiquitination was determined by Western blot using K48 ubiquitin-specific antibody.

FIGS. 2A-2F: CPXV006 co-opts the host SCF machinery to promote RIPK3 degradation and necroptosis resistance. (A) Schematic diagram of the domain organization of vIRD from CPXV and the vIRD orthologues from VACV Western Reserve and Copenhagen strains. (B) L929 cells infected with wild type or the indicated mutant CPXV were analyzed for RIPK3 expression by Western blot. (C) Kinetics of vIRD expression was determined by Western blot at the indicated after CPXV infection. (D) Immunoprecipitation of SKP1 and Western blot detection of vIRD and CUL1 recruitment upon CPXV infection. n.s.=non-specific band. (E) Effect of the neddylation inhibitor MLN4924 on CUL1 neddylation, RIPK3 degradation and vIRD expression was determined by Western blot. (F) CPXV-infected L929 cells were treated with the indicated inhibitors. Cell death was monitored by Incucyte.

FIGS. 3A-3C: Ankyrin repeats and RHIM-mediated interaction between vIRD and RIPK3. (A) HEK293T cells were transfected with the indicated GFP-tagged vIRD and RIPK3. Interaction was determined by GFP immunoprecipitation and Western blot as indicated. Schematic diagram on the right indicate the truncation mutants used. (B) HEK293T cells were transfected with the indicated plasmids. Interaction between RIPK3 mutants and vIRD was determined by Western blot after anti-FLAG immunoprecipitation. (C) Interaction of vIRD with SKP1 and CUL1 requires an intact F-box. L929 cells were infected with rVACV-FLAG-vIRD or rVACV-FLAG-vIRD-ΔF. Binding between vIRD, CUL1 and SKP1 was determined by immunoprecipitation and Western blot.

FIGS. 4A-4F: vIRD restores RIPK3 degradation and necroptosis resistance of VACV. (A) Expression and assembly of vIRD with SKP1 and CUL1 in L929 cells infected with the indicated rVACV. (B) Cell death in L929 cells infected with the indicated rVACV. (C) Western blot analysis of RIPK3 expression in L929 cells infected with the indicated rVACV. CPXV006 (601) is a rabbit polyclonal antibody specific for the C-terminus of vIRD. (D) L929 cells infected with the indicated viruses were examined for RIPK3 degradation by Western blot. (E) ECTV-infected L929 cells are resistant to necroptosis. (F) Resistance of ECTV-infected L929 cells to necroptosis is reversed in the presence of the neddylation inhibitor MLN4924.

FIGS. 5A-5C: vIRD regulates viral replication in vivo. (A) Wild type (WT) or Ripk3$^{\Delta R/\Delta R}$ (DR) mice were infected with wild type (WT) or CPXV-ΔvIRD (Mut) via the intraperitoneal route as indicated. Three and a half days post-infection, viral load in the indicated tissues was determined by Vero cell plaque assay. (B) Mice were infected with the indicated rVACV for 3.5 days. Viral titers in the indicated tissues were determined by Vero cell plaque assay. (C) Survival of wild type or Ripk3$^{\Delta R/\Delta R}$ (DR) mice infected with the indicated wild type or ΔvIRD CPXV.

FIGS. 6A-6D: vIRD regulates virus-induced inflammation. (A) Heat map of the expression of the top DE genes in WT CPXV and UI and CPXV-ΔvIRD vs UI groups were shown. (B) Q-PCR analysis of Ccl2 and Cxcl2 expression in infected mice of the indicated groups. (C) FACS analysis of CD11b$^+$GR1$^+$ neutrophils isolated from the visceral fat pad of the infected mice. (D) H&E staining of infected visceral fat pad from mice in the different groups. *p<0.05, #p<0.01.

FIG. 7: Representative sequence alignment of vIRD polypeptide sequences from genomes of various orthopoxviruses. The alignment demonstrates that the majority encode highly conserved vIRD orthologues, each having at least 65% amino acid sequence identity with CPXV-vIRD.

FIGS. 8A-8G: CPXV confers resistance to necroptosis in mouse, human primary and transformed cells. (A) MEFs were infected with the indicated GFP recombinant viruses for 18 hours, followed by TNF stimulation for 16 hours. Cell death in the GFP+ infected cells were enumerated by propidium iodide (PI) staining and flow cytometry. Representative FACS plots are shown. (B) L929 cells were infected with the indicated viruses and cell death was determined using Incucyte. (C) Caspase 8-deficient Jurkat cells (J3.2) were infected with rCPXV-GFP or rVACV-GFP. TNF-induced cell death in the infected (GFP+) and uninfected (GFP-) populations were determined by PI staining and flow cytometry. (D-E) FADD-deficient Jurkat cells (142) infected with (D) rCPXV-GFP or (E) rVACV-GFP were stimulated with TNF and cell death was measured by PI and flow cytometry. (F-G) Wild type TNFR2+ Jurkat cells (clone 4E3) treated with (F) TNF or (G) TNF and the Smac mimetic (TS) BV6. #p<0.01.

FIGS. 9A-9E: CPXV induces RIPK3 degradation via the proteasome. (A) L929 cells were infected with CPXV for 18 hours followed by TNF treatment for the indicated times. Total cell lysates were analyzed for expression of the indicated cell death signal adaptors by Western blot. (B) Human colorectal cancer cell line Colo205 and FADD-deficient Jurkat cells (142) were infected with CPXV and expression of cell death adaptors was determined by Western blot. (C) Bone marrow-derived macrophages were infected with CPXV for the indicated times and expression of the indicated necroptosis adaptors was determined by Western blot. (D) mRNA level of Ripk3 in response to CPXV infection was determined by Q-PCR. (E) L929 cells treated with the indicated inhibitors and infected with CPXV was determined by Western blot.

FIGS. 10A-10D: vIRD interacts with CUL1 to promote RIPK3 degradation. (A-B) HEK293T cells were transfected with the indicated plasmids. Immunoprecipitation was done with (A) anti-Myc tag antibody or (B) anti-HA antibody. Binding between vIRD and different Cullins was determined by Western blot. (C) CPXV-induced cell death in L929 cells is partially dependent on autocrine TNF production. L929 cells infected with CPXV were treated with the neddylation inhibitor MLN4924 and anti-TNF neutralizing antibody as indicated. Cell death was determined using Cytotox Green and Incucyte imaging. (D) HEK293T cells were transfected with the indicated plasmids. Binding between vIRD and the RIPK3 truncations was determined by co-IP with the indicated antibodies. (E) vIRD does not interact with other RHIM-containing adaptors. HEK293T cells transfected with the indicated plasmids. Binding was determined by Western blot as indicated.

FIGS. 11A-11D: vIRD is sufficient to induce RIPK3 degradation. (A) L929 cells infected with the indicated virus was monitored for cell death with Cytotox Green and Incucyte. UI: Uninfected. (B) Sequence alignment of vIRD orthologues from CPXV, ECTV, MPXV and VARV. Identical residues are highlighted in red. Conserved non-polar (dark green), polar (light green), positive charge (brown) and negative charge (light blue) residues are highlighted. C) ECTV encodes a functional vIRD. HEK293T cells were transfected with the indicated plasmids. Binding with RIPK3 and RIPK3 degradation was determined by co-immunoprecipitation and Western blot as indicated. (D) RIPK3 degradation by vIRD orthologues from MPXV, CPXV but not MYXV. HEK293T cells were transfected with the indicated vIRDs and RIPK3. RIPK3 expression was determined by Western blot.

FIGS. 12A-12B: vIRD regulates virus-induced NF-κB activation and survival in mouse infection. (A) Human THP1 cells were differentiated with phorbol ester for 24 hours, followed by infection with wild type or vIRD-deficient CPXV as indicated. Phosphorylation and degradation of IxBa was determined by Western blot. (B) Viral load in the indicated tissues were determined by Vero plaque assay on the indicated days post-infection. Mice that were moribund were taken down on day 5-6, while surviving mice that were healthy were kept until day 26 prior to viral titer determination.

FIGS. 13A-13B: vIRD regulates inflammatory gene expression. (A) Expression of the indicated cytokines in the visceral fat pad was analyzed by Q-PCR in each of the indicated groups. (B) Expression of the indicated inflammatory genes in mice infected with wild type or vIRD-deleted CPXV. *p<0.05, #p<0.01.

DETAILED DESCRIPTION

Figures 1A, 1B, 1C, 1D, 1E, 1F:
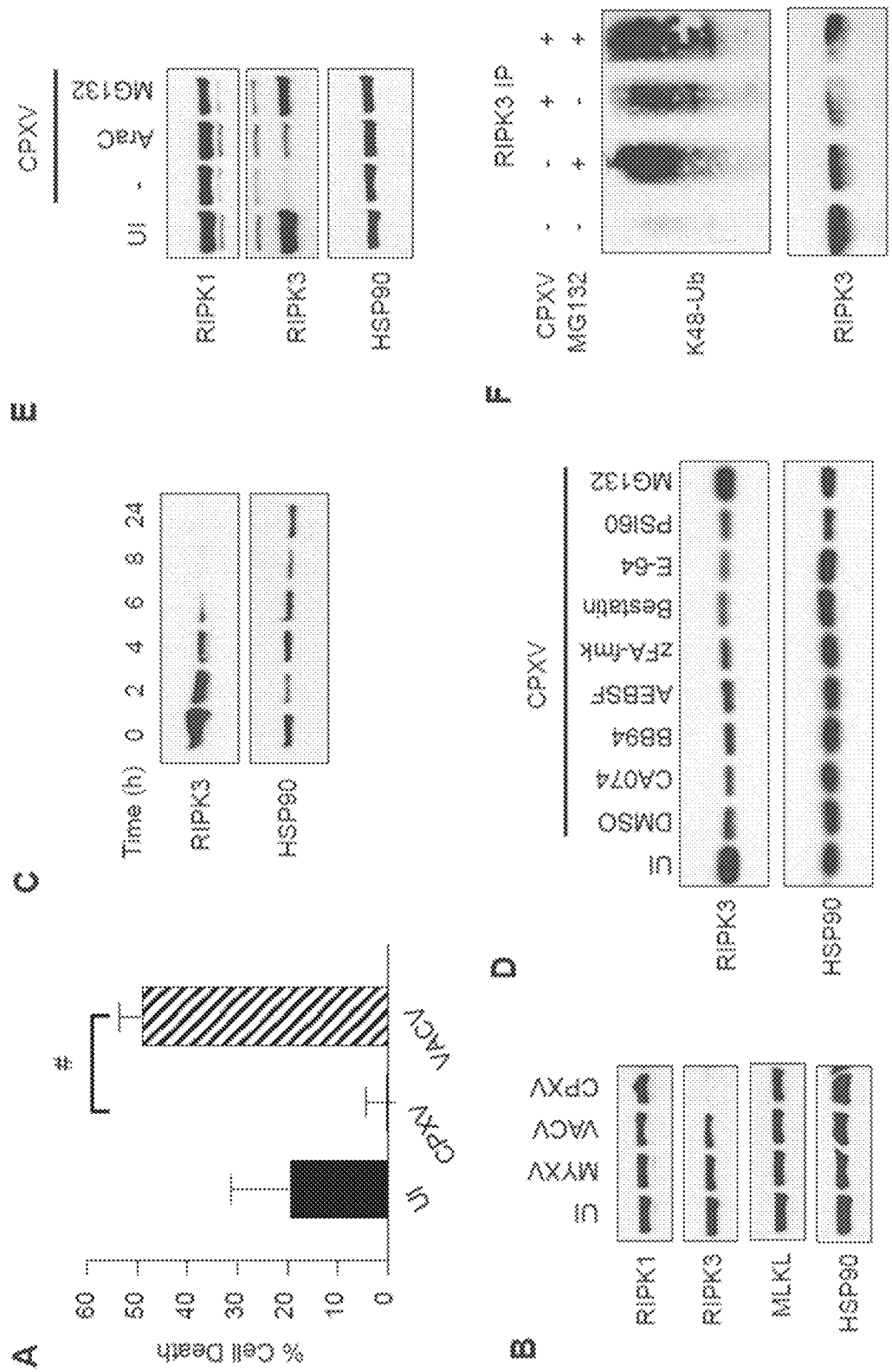

The present disclosure provides compositions and methods related to the modulation of the inflammation response activated by a host's immune system. In particular, the present disclosure provides novel inhibitors of proteins that exhibit pro-inflammatory activity (e.g., RIPK1, RIPK3, ZBP1, TRIF, CUL1, SKP1, and NF-κB, among others), as well as corresponding therapeutic compositions and methods of treatment using these inhibitors.

The vaccine strain against smallpox, vaccinia virus (VACV), is highly immunogenic yet causes relatively benign disease. This differential pathogenicity is attributed to gene loss in VACV, although the responsible viral factor has not been identified. Using a targeted siRNA screen, results provided herein have identified a viral inhibitor found in cowpox virus (CPXV) and several other orthopoxviruses that binds to the host SKP1-Cullinl-F-box (SCF) machinery and the essential necroptosis kinase Receptor Interacting Protein Kinase 3 (RIPK3). This "viral inducer of RIPK3 degradation (vIRD)" triggers ubiquitination and proteasome-mediated degradation of RIPK3 and inhibits necroptosis. The distantly related leporipoxvirus Myxoma virus (MYXV) infects host that lacks Ripk3 and encodes a non-functional vIRD. Introduction of vIRD into VACV, which also encodes a defective vIRD, enhance viral replication in mice. Moreover, deletion of vIRD reduced CPXV-induced inflammation, viral replication and mortality in mice. Thus, results provided herein demonstrate that vIRD-RIPK3 drives pathogen-host evolution and regulates poxviral pathogenesis.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the present disclosure may be readily combined, without departing from the scope or spirit of the embodiments provided herein. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences for the production of a polypeptide, precursor, or RNA (e.g., rRNA, tRNA, sRNA, microRNA, lincRNA). The polypeptide can be encoded by a full-length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than about 300 residues long (e.g., between 15 and 100), however, as used herein, the term is also intended to encompass longer polynucleotide chains. Oligonucleotides are often referred to by their length. For example, a 24-residue oligonucleotide is referred to as a "24-mer." Oligonucleotides can form secondary and tertiary structures by self-hybridizing or by hybridizing to other polynucleotides. Such structures can include, but are not limited to, duplexes, hairpins, cruciforms, bends, and triplexes.

"Peptide" and "polypeptide" as used herein, and unless otherwise specified, refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

As used herein, the term "fragment" refers to a peptide or polypeptide that results from dissection or "fragmentation" of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or polypeptide that is not a subsequence of a preexisting whole protein is not a fragment (e.g., not a fragment of a preexisting protein).

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

In some embodiments the substitutions can be conservative amino acid substitutions. Examples of conservative amino acid substitutions, unlikely to affect biological activity, include the following: alanine for serine, valine for isoleucine, aspartate for glutamate, threonine for serine, alanine for glycine, alanine for threonine, serine for asparagine, alanine for valine, serine for glycine, tyrosine for phenylalanine, alanine for proline, lysine for arginine, aspartate for asparagine, leucine for isoleucine, leucine for valine, alanine for glutamate, aspartate for glycine, and these changes in the reverse. See e.g. Neurath et al., The Proteins, Academic Press, New York (1979), the relevant portions of which are incorporated herein by reference. Further, an exchange of one amino acid within a group for another amino acid within the same group is a conservative substitution, where the groups are the following: (1) alanine, valine, leucine, isoleucine, methionine, norleucine, and phenylalanine: (2) histidine, arginine, lysine, glutamine, and asparagine; (3) aspartate and glutamate; (4) serine, threonine, alanine, tyrosine, phenylalanine, tryptophan, and cysteine; and (5) glycine, proline, and alanine.

The term "homology" and "homologous" refers to a degree of identity. There may be partial homology or complete homology. A partially homologous sequence is one that is less than 100% identical to another sequence.

As used herein, the terms "complementary" or "complementarity" are used in reference to polynucleotides (e.g., a sequence of nucleotides such as an oligonucleotide or a target nucleic acid) related by the base-pairing rules. For example, for the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

In some contexts, the term "complementarity" and related terms (e.g., "complementary", "complement") refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. The percentage complementarity need not be calculated over the entire length of a nucleic acid sequence. The percentage of complementarity may be limited to a specific region of which the nucleic acid sequences that are base-paired, e.g., starting from a first base-paired nucleotide and ending at a last base-paired nucleotide. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present disclosure and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Thus, in some embodiments, "complementary" refers to a first nucleobase sequence that is at least 60%, 65%, 70%, 75%, 80%, 85%, 90%, 95%, 97%, 98%, or 99% identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases, or that the two sequences hybridize under stringent hybridization conditions. "Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleic acid has a nucleobase sequence that is identical to the complement of the nucleic acid over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases.

As used herein, a "double-stranded nucleic acid" may be a portion of a nucleic acid, a region of a longer nucleic acid, or an entire nucleic acid. A "double-stranded nucleic acid" may be, e.g., without limitation, a double-stranded DNA, a double-stranded RNA, a double-stranded DNA/RNA hybrid, etc. A single-stranded nucleic acid having secondary structure (e.g., base-paired secondary structure) and/or higher order structure comprises a "double-stranded nucleic acid". For example, triplex structures are considered to be "double-stranded". In some embodiments, any base-paired nucleic acid is a "double-stranded nucleic acid"

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence. The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions.

As used herein, "operably linked" refers a nucleic acid sequence, e.g., a gene encoding a recombinant vIRD, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

As used herein, "promoter" refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Prokaryotic promoters are typically classified into two classes: inducible and constitutive.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample. The term "substantially purified" as used herein refers to a molecule such as a polypeptide, carbohydrate, nucleic acid etc. which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens such as polysaccharides, small molecule, mimics etc. are included within the present disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, a "pharmaceutically acceptable excipient and/or carrier" or "diagnostically acceptable excipient and/or carrier" includes but is not limited to, sterile distilled water, saline, phosphate buffered solutions, amino acid-based buffers, or bicarbonate buffered solutions. An excipient selected and the amount of excipient used will depend upon the mode of administration. Administration comprises an injection, infusion, or a combination thereof.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

2. RECOMBINANT vIRD POLYPEPTIDES

Embodiments of the present disclosure include the identification of a viral inhibitor termed "viral Inducer of RIPK3 Degradation" (vIRD). vIRD was identified from a targeted siRNA screen in CPXV-infected cells. During CPXV infection, vIRD binds to RIPK3 via its N-terminal ankyrin repeats and the cellular SKP1-CUL1 complex via its C-terminal F-box. vIRD promotes RIPK3 ubiquitination and proteasome-mediated degradation, leading to necroptosis resistance of the infected cells. Deletion of vIRD or pharmacologic inhibition of the SKP1-CUL1 complex restored virus-induced RIPK3 degradation and sensitivity to necroptosis of CPXV-infected cells. In mouse infection, deletion of vIRD greatly reduced chemokine expression, immune cell recruitment, tissue injury, viral replication and mortality of CPXV infection. These effects were reversed when infection was performed in RIPK3-deficient mice, indicating that RIPK3 is the main cellular target of vIRD-mediated immune evasion.

Intact vIRD orthologues were identified in other orthopoxviruses such as variola virus, monkeypox virus and ectromelia virus. Surprisingly, different VACV strains encode either a truncated and inactive vIRD orthologue or are missing the gene entirely. Introduction of an intact vIRD increased VACV replication in vivo. These results demonstrate that vIRD critically regulates pathogenicity of orthopoxvirus infection. Moreover, vIRD and RIPK3 may play an important role in pathogen-host co-evolution.

Figures 13A, 13B:
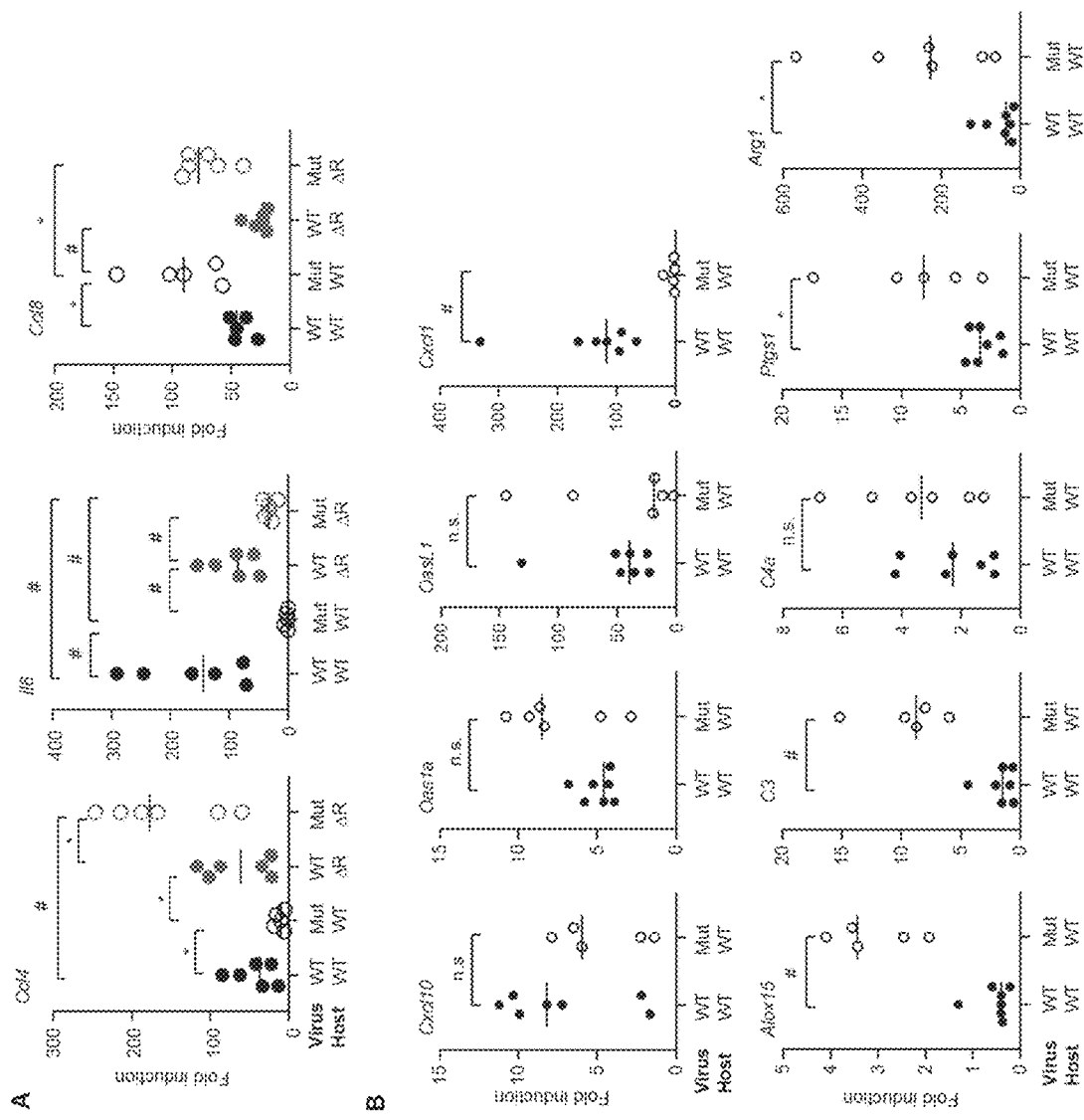

Using CPXV-ΔvIRD and infection in RIPK3-deficient mice, embodiments of the present disclosure demonstrate that vIRD targeting of RIPK3 is a key mechanism by which orthopoxviruses regulate viral pathogenesis. Although necroptosis is widely believed to promote anti-viral inflammation (Nailwal and Chan, 2018), results provided herein surprisingly indicated that vIRD-mediated inhibition of necroptosis did not restrict inflammation. Rather, vIRD promotes expression of many chemokines and infiltration of neutrophils in infected visceral fat tissue. While there are inflammatory genes whose expression was either unchanged or induced in the absence of vIRD (FIG. 13B), the increased expression of select inflammatory genes does challenge the dogma that necroptosis promotes anti-viral inflammation. In some embodiments provided herein, expression of certain inflammatory genes was significantly upregulated in RIPK3-deficient mice in response to CPXV-ΔvIRD (FIG. 13A).

Koehler and colleagues recently reported that the VACV E3 protein binds to another necroptosis adaptor ZBP1 via its Zα domain to inhibit ZBP1/RIPK3-dependent necroptosis (Koehler et al., 2017). Cells infected with mutant VACV lacking the Zα domain of E3 were highly sensitive to interferon-induced cell death. It is noteworthy that this E3-ZBP1 axis is distinct from necroptosis induced by TNF and TNF receptors, which drive RIPK1/RIPK3-dependent necroptosis independent of ZBP1 (Carpenter et al., 1994; Cho et al., 2009; Polykratis et al., 2014). Thus, vIRD and E3 are functionally distinct.

Figures 8A, 8B, 8C, 8D, 8E, 8F, 8G:
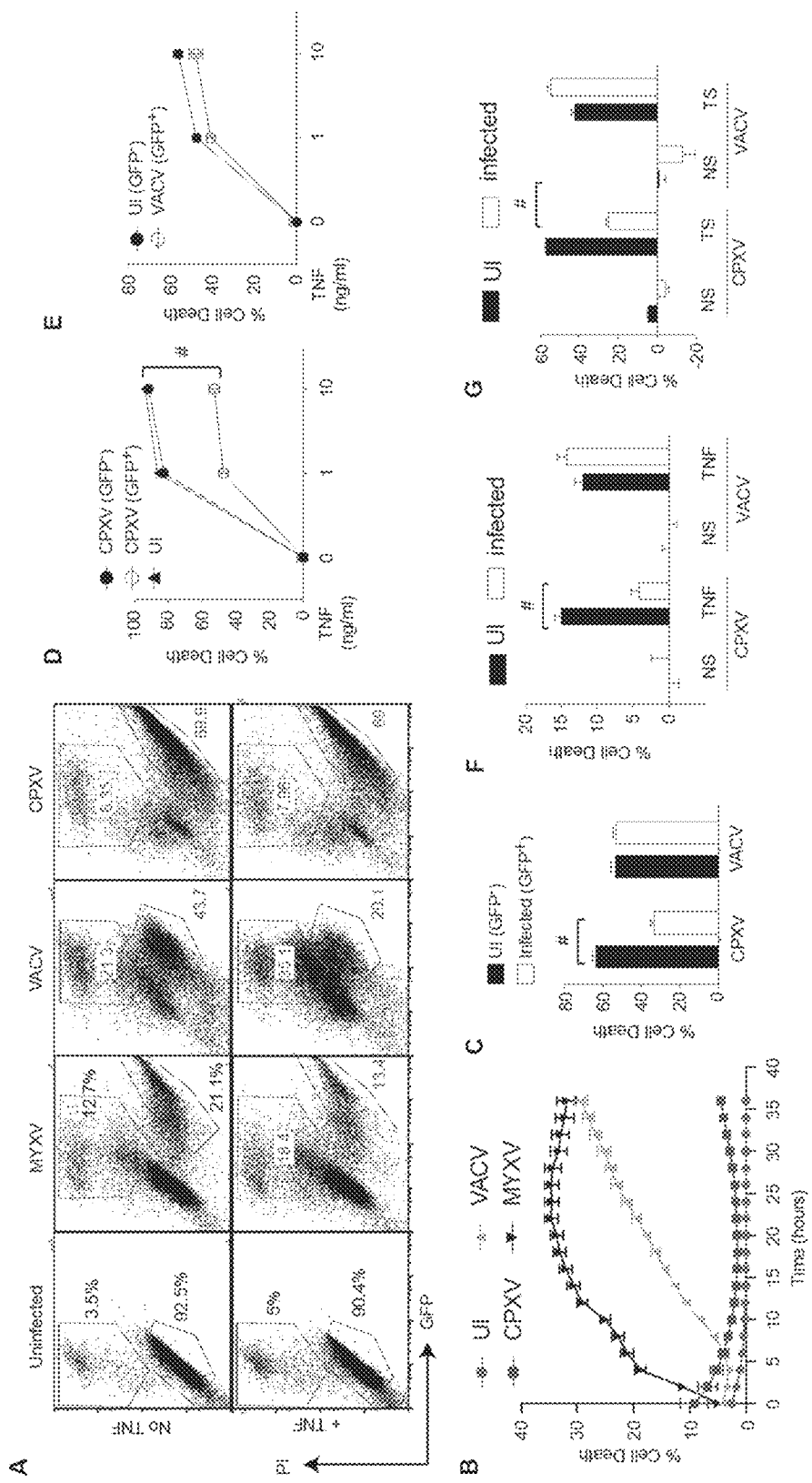

MYXV contains a vIRD-like orthologue that lacks the essential F-box, has poor sequence conservation throughout its ankyrin repeats, and did not induce RIPK3 degradation. Yet, unlike VACV or CPXV that lacks vIRD, MYXV causes deadly disease in its natural host rabbits due to the host's deficiency of Ripk3. Thus, the lack of selective pressure from RIPK3 could have led to the loss of a functional vIRD in MYXV. In contrast to vIRDs, vMLKLs are found in avipoxviruses whose hosts lack RIPK3 expression, but not in orthopoxviruses. Interestingly, despite having a vMLKL (Petrie et al., 2019), MYXV-infected cells were sensitive to TNF-induced necroptosis (FIGS. 8A-8B). Unlike avipoxviruses, orthopoxviruses infect hosts with RIPK3 expression. VACV, which lacks vIRD, or deletion of vIRD in CPXV both greatly reduced virus-induced pathogenesis. By contrast, orthopoxviruses that encode intact vIRD including VARV and ECTV cause severe and often lethal disease in their natural hosts.

The poxvirus genomes encode several proteins with N-terminal ankyrin repeats and a C-terminal F-box. This architecture is not found in mammalian F-box or ankyrin repeats-containing adaptors, indicating that this unique assembly might have arisen from gene recombination or gene shuffling during host-pathogen evolution. The identity of the cellular targets for these viral ankyrin repeat-F box adaptors has been elusive. Results provided herein have identified RIPK3 as a bona fide substrate for one of these viral ankyrin repeats/F-box adaptors. The ankyrin repeat-RHIM binding between vIRD and RIPK3 represents a distinct mode of interaction, since previous studies showed that the RHIM exclusively mediates homotypic RHIM-RHIM interaction. However, it is noteworthy that sequences flanking the RHIM may also contribute to interaction with vIRD. Necroptosis adaptors have critical functions in cell death and inflammation. Since manipulating the activity of vIRD could tune the magnitude and quality of host inflammation, the principles revealed from the data provided herein may inform the design of more efficacious and safer vaccines in the future.

In accordance with the above description, embodiments of the present disclosure include a recombinant polypeptide inhibitor of at least one inflammatory-modulating protein. In some embodiments, the recombinant polypeptide inhibitor is derived from a poxvirus peptide or polypeptide (e.g., a vIRD peptide or polypeptide), including any derivative or variant thereof. In some embodiments, the poxvirus peptide or polypeptide is derived from a cowpox virus, a ectromelia virus, a monkeypox virus, a variola virus (smallpox), a horsepox virus, a skunkpox virus, a taterapox virus, a camelpox virus, or a volepox virus, or any derivative, variant, or isolate thereof. As would be recognized by one of ordinary skill in the art based on the present disclosure, the recombinant polypeptide inhibitor of an inflammatory-modulating protein can be any other recombinant vIRD peptide or polypeptide derived from a poxvirus, that has less than 100% amino acid identity with a naturally-occurring counterpart peptide or polypeptide.

In some embodiments, the polypeptide inhibitor includes a plurality of Ankyrin repeat motifs. In some embodiments, the polypeptide comprises between 2 and 6 Ankyrin repeat motifs. In some embodiments, the polypeptide comprises between 3 and 6 Ankyrin repeat motifs. In some embodiments, the polypeptide comprises between 4 and 6 Ankyrin repeat motifs. In some embodiments, the polypeptide comprises between 5 and 6 Ankyrin repeat motifs. In some embodiments, the polypeptide comprises at least 5 Ankyrin repeat motifs. In some embodiments, the polypeptide comprises greater than 5 Ankyrin repeat motifs.

In some embodiments, the polypeptide inhibitor has at least 65% sequence identity with SEQ ID NO: 1. In some embodiments, the polypeptide inhibitor has at least 70% sequence identity with SEQ ID NO: 1. In some embodiments, the polypeptide inhibitor has at least 75% sequence identity with SEQ ID NO: 1. In some embodiments, the polypeptide inhibitor has at least 80% sequence identity with SEQ ID NO: 1. In some embodiments, the polypeptide inhibitor has at least 85% sequence identity with SEQ ID NO: 1. In some embodiments, the polypeptide inhibitor has at least 90% sequence identity with SEQ ID NO: 1. In some embodiments, the polypeptide comprises at least 95% sequence identity with SEQ ID NO: 1. In some embodiments, the polypeptide comprises at least 96%, 97%, 98%, or 99% sequence identity with SEQ ID NO: 1. In some embodiments, the polypeptide comprises less than 100% sequence identity with SEQ ID NO: 1.

In some embodiments, the polypeptide includes a F-box motif. In some embodiments, the polypeptide comprises a F-box motif but lacks at least one Ankyrin repeat motif as compared to a naturally-occurring counterpart polypeptide. In some embodiments, the polypeptide comprises a plurality of Ankyrin repeat motifs but lacks an F-box motif as compared to a naturally-occurring counterpart polypeptide. In some embodiments, the polypeptide has at least 65% sequence identity with any of SEQ ID NOs: 1-4. In some embodiments, the polypeptide has at least 70% sequence identity with any of SEQ ID NOs: 1-4. In some embodiments, the polypeptide has at least 75% sequence identity with any of SEQ ID NOs: 1-4. In some embodiments, the polypeptide has at least 80% sequence identity with any of SEQ ID NOs: 1-4. In some embodiments, the polypeptide has at least 85% sequence identity with any of SEQ ID NOs: 1-4. In some embodiments, the polypeptide has at least 90% sequence identity with any of SEQ ID NOs: 1-4. In some embodiments, the polypeptide has at least 95% sequence identity with any of SEQ ID NOs: 1-4. In some embodiments, the polypeptide comprises at least 96%, 97%, 98%, or 99% sequence identity with any of SEQ ID NOs: 1-4. In some embodiments, the polypeptide comprises less than 100% sequence identity with any of SEQ ID NOs: 1-4. In some embodiments, the polypeptide comprises any one of SEQ ID NOs: 1-4. In some embodiments, the polypeptide comprises at least one amino acid substitution that is not present in any one of SEQ ID NOs: 1-4.

In some embodiments, the polypeptide has at least 65% sequence identity with any of SEQ ID NOs: 5-12. In some embodiments, the polypeptide has at least 70% sequence identity with any of SEQ ID NOs: 5-12. In some embodiments, the polypeptide has at least 75% sequence identity with any of SEQ ID NOs: 5-12. In some embodiments, the polypeptide has at least 80% sequence identity with any of SEQ ID NOs: 5-12. In some embodiments, the polypeptide has at least 85% sequence identity with any of SEQ ID NOs: 5-12. In some embodiments, the polypeptide has at least 90% sequence identity with any of SEQ ID NOs: 5-12. In some embodiments, the polypeptide has at least 95% sequence identity with any of SEQ ID NOs: 5-12. In some embodiments, the polypeptide comprises at least 96%, 97%, 98%, or 99% sequence identity with any of SEQ ID NOs: 5-12. In some embodiments, the polypeptide comprises less than 100% sequence identity with any of SEQ ID NOs: 5-12. In some embodiments, the polypeptide comprises any one of SEQ ID NOs: 5-12. In some embodiments, the polypeptide comprises less than 100% sequence identity with any one of SEQ ID NOs: 1 and 5-12. In some embodiments, the polypeptide comprises at least one amino acid substitution that is not present in any one of SEQ ID NOs: 1 and 5-12.

In accordance with the embodiments of the recombinant polypeptides described above, the inflammatory-modulating protein(s) that is inhibited by the recombinant polypeptide inhibitor (e.g., vIRD) includes one or more of receptor interacting protein kinase-1 (RIPK1), receptor interacting protein kinases-3 (RIPK3), TIR-domain-containing adapter-inducing interferon-β (TRIF), Z-DNA binding protein 1 (ZBP1), Cullin-1 (CUL1), and/or S-phase kinase associated protein 1 (SKP1). In some embodiments, the polypeptide binds to one or more of RIPK1, RIPK3, TRIF, ZBP1, CUL1, and/or SKP1, such that the binding of the polypeptide inhibits expression, activity, and/or promotes degradation of RIPK1, RIPK3, TRIF, ZBP1, CUL1, and/or SKP1.

Embodiments of the present disclosure also include a nucleic acid molecule comprising a sequence encoding one or more of the recombinant polypeptide inhibitors provided herein (e.g., SEQ ID NOs: 1-12). Embodiments of the present disclosure also include a vector comprising this nucleic acid molecule. In some embodiments, the polynucleotide comprises a sequence encoding one or more recombinant polypeptide inhibitors of any of SEQ ID NOs: 1-12, including any variants, mutants, chimeras, or fusions thereof. In some embodiments, the gene encoding a recombinant polypeptide inhibitor is mutagenized; mutants exhibiting increased activity or decreased activity can be selected, and the mutagenized gene can be isolated and inserted into a host cell for propagation. A gene comprising a recombinant polypeptide inhibitor described herein may be present on a plasmid, vector, or chromosome. In some embodiments, the disclosure provides a nucleic acid comprising gene sequence encoding one or more recombinant polypeptide inhibitors, wherein the recombinant polypeptide inhibitor is mutagenized and synthesized into its corresponding peptide or polypeptide. In some embodiments, the recombinant polypeptide inhibitor is a chimeric protein comprising different peptide motifs conferring various functionality and binding properties, as described further herein.

In some embodiments, the nucleic acid comprises a sequence encoding one or more recombinant polypeptide inhibitors that comprise amino acids in its sequence that are substantially the same as an amino acid sequence described herein. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T. Similarly contemplated is replacing a basic amino acid with another basic amino acid (e.g., replacement among Lys, Arg, His), replacing an acidic amino acid with another acidic amino acid (e.g., replacement among Asp and Glu), replacing a neutral amino acid with another neutral amino acid (e.g., replacement among Ala, Gly, Ser, Met, Thr, Leu, Asn, Gln, Phe, Cys, Pro, Trp, Tyr, Val).

3. COMPOSITIONS

Embodiments of the present disclosure include a pharmaceutical composition comprising a recombinant polypeptide inhibitor of at least one inflammatory-modulating protein comprising a plurality of Ankyrin repeat motifs and at least 65% sequence identity with SEQ ID NO: 1, and a pharmaceutically acceptable carrier or excipient. In accordance with these embodiments, administration of the composition treats an inflammatory disease or condition.

In some embodiments of the composition, the recombinant polypeptide inhibitor is derived from a poxvirus peptide or polypeptide (e.g., a vIRD peptide or polypeptide), including any derivative or variant thereof. In some embodiments, the poxvirus peptide or polypeptide is derived from a cowpox virus, a ectromelia virus, a monkeypox virus, a variola virus (smallpox), a horsepox virus, a skunkpox virus, a taterapox virus, a camelpox virus, or a volepox virus, or any derivative, variant, or isolate thereof. As would be recognized by one of ordinary skill in the art based on the present disclosure, the recombinant polypeptide inhibitor of an inflammatory-modulating protein can be any other recombinant vIRD peptide or polypeptide derived from a poxvirus, that has less than 100% amino acid identity with a naturally-occurring counterpart peptide or polypeptide.

In some embodiments of the composition, the polypeptide inhibitor includes a plurality of Ankyrin repeat motifs. In some embodiments, the polypeptide comprises between 2 and 6 Ankyrin repeat motifs. In some embodiments, the polypeptide comprises between 3 and 6 Ankyrin repeat motifs. In some embodiments, the polypeptide comprises between 4 and 6 Ankyrin repeat motifs. In some embodiments, the polypeptide comprises between 5 and 6 Ankyrin repeat motifs. In some embodiments, the polypeptide comprises at least 5 Ankyrin repeat motifs. In some embodiments, the polypeptide comprises greater than 5 Ankyrin repeat motifs.

In some embodiments of the composition, the polypeptide inhibitor has at least 65% sequence identity with SEQ ID NO: 1. In some embodiments, the polypeptide inhibitor has at least 70% sequence identity with SEQ ID NO: 1. In some embodiments, the polypeptide inhibitor has at least 75% sequence identity with SEQ ID NO: 1. In some embodiments, the polypeptide inhibitor has at least 80% sequence identity with SEQ ID NO: 1. In some embodiments, the polypeptide inhibitor has at least 85% sequence identity with SEQ ID NO: 1. In some embodiments, the polypeptide inhibitor has at least 90% sequence identity with SEQ ID NO: 1. In some embodiments, the polypeptide comprises at least 95% sequence identity with SEQ ID NO: 1. In some embodiments, the polypeptide comprises at least 96%, 97%, 98%, or 99% sequence identity with SEQ ID NO: 1. In some embodiments, the polypeptide comprises less than 100% sequence identity with SEQ ID NO: 1.

In some embodiments of the composition, the polypeptide includes a F-box motif. In some embodiments, the polypeptide comprises a F-box motif but lacks at least one Ankyrin repeat motif as compared to a naturally-occurring counterpart polypeptide. In some embodiments, the polypeptide comprises a plurality of Ankyrin repeat motifs but lacks an F-box motif as compared to a naturally-occurring counterpart polypeptide. In some embodiments, the polypeptide has at least 65% sequence identity with any of SEQ ID NOs: 1-4. In some embodiments, the polypeptide has at least 70% sequence identity with any of SEQ ID NOs: 1-4. In some embodiments, the polypeptide has at least 75% sequence identity with any of SEQ ID NOs: 1-4. In some embodiments, the polypeptide has at least 80% sequence identity with any of SEQ ID NOs: 1-4. In some embodiments, the polypeptide has at least 85% sequence identity with any of SEQ ID NOs: 1-4. In some embodiments, the polypeptide has at least 90% sequence identity with any of SEQ ID NOs: 1-4. In some embodiments, the polypeptide has at least 95% sequence identity with any of SEQ ID NOs: 1-4. In some embodiments, the polypeptide comprises at least 96%, 97%, 98%, or 99% sequence identity with any of SEQ ID NOs: 1-4. In some embodiments, the polypeptide comprises less than 100% sequence identity with any of SEQ ID NOs: 1-4. In some embodiments, the polypeptide comprises any one of SEQ ID NOs: 1-4. In some embodiments, the polypeptide comprises at least one amino acid substitution that is not present in any one of SEQ ID NOs: 1-4.

In some embodiments of the composition, the polypeptide has at least 65% sequence identity with any of SEQ ID NOs: 5-12. In some embodiments, the polypeptide has at least 70% sequence identity with any of SEQ ID NOs: 5-12. In some embodiments, the polypeptide has at least 75% sequence identity with any of SEQ ID NOs: 5-12. In some embodiments, the polypeptide has at least 80% sequence identity with any of SEQ ID NOs: 5-12. In some embodiments, the polypeptide has at least 85% sequence identity with any of SEQ ID NOs: 5-12. In some embodiments, the polypeptide has at least 90% sequence identity with any of SEQ ID NOs: 5-12. In some embodiments, the polypeptide has at least 95% sequence identity with any of SEQ ID NOs: 5-12. In some embodiments, the polypeptide comprises at least 96%, 97%, 98%, or 99% sequence identity with any of SEQ ID NOs: 5-12. In some embodiments, the polypeptide comprises less than 100% sequence identity with any of SEQ ID NOs: 5-12. In some embodiments, the polypeptide comprises any one of SEQ ID NOs: 5-12. In some embodiments, the polypeptide comprises less than 100% sequence identity with any one of SEQ ID NOs: 1 and 5-12. In some embodiments, the polypeptide comprises at least one amino acid substitution that is not present in any one of SEQ ID NOs: 1 and 5-12.

In some embodiments of the composition, the inflammatory-modulating protein(s) that is inhibited by the recombinant polypeptide inhibitor (e.g., vIRD) includes one or more of receptor interacting protein kinase-1 (RIPK1), receptor interacting protein kinases-3 (RIPK3), TIR-domain-containing adapter-inducing interferon-β (TRIF), Z-DNA binding protein 1 (ZBP1), Cullin-1 (CUL1), and/or S-phase kinase associated protein 1 (SKP1). In some embodiments, the polypeptide binds to one or more of RIPK1, RIPK3, TRIF, ZBP1, CUL1, and/or SKP1, such that the binding of the polypeptide inhibits expression, activity, and/or promotes degradation of RIPK1, RIPK3, TRIF, ZBP1, CUL1, and/or SKP1.

The compositions described herein can be administered to a subject, either alone or in combination with a pharmaceutically acceptable excipient and/or carrier, in an amount sufficient to induce an appropriate immune response. The response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

Embodiments of the present disclosure provide methods of modulating an immune response in a subject, inhibiting necroptosis in a subject or cell, and vaccinating a subject from an infectious disease or cancer by administering to the subject an effective amount of a recombinant polypeptide inhibitor (e.g., vIRD) composition as described herein. An "effective amount" as used herein means an amount which provides a therapeutic or prophylactic benefit. Effective amounts of vIRDs can be determined by a physician with consideration of individual differences in age, weight, tumor size, extent of infection or metastasis, and condition of the patient (subject). It can generally be stated that a pharmaceutical composition comprising the vIRD described herein may be administered at a dosage of 20 to 200 U/l, preferably 40 to 175 U/l, including all integer values within those ranges. vIRD compositions may also be administered multiple times at these dosages. The optimal dosage and treatment regime for a particular patient can readily be determined by one skilled in the art of medicine by monitoring the patient for signs of disease and adjusting the treatment accordingly.

An effective amount of a recombinant polypeptide inhibitor (e.g., vIRD) composition as described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The present disclosure is not limited to dosing intervals that are spaced equally in time, but encompass doses at non-equal intervals, such as a priming schedule consisting of administration at 1 day, 4 days, 7 days, and 25 days, just to provide a non-limiting example.

A "pharmaceutically acceptable excipient and/or carrier" or "diagnostically acceptable excipient and/or carrier" includes but is not limited to, sterile distilled water, saline, phosphate buffered solutions, amino acid-based buffers, or bicarbonate buffered solutions. An excipient selected and the amount of excipient used will depend upon the mode of administration. Administration comprises an injection, infusion, or a combination thereof.

An effective amount for a particular subject/patient may vary depending on factors such as the condition being treated, the overall health of the patient, the route and dose of administration, and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

For any compositions described herein comprising a recombinant polypeptide inhibitor (e.g., vIRD), a therapeutically effective amount can be initially determined from animal models. A therapeutically effective dose can also be determined from human data for caspase inhibitors and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the present disclosure can be administered in pharmaceutically acceptable solutions, which may routinely contain pharmaceutically acceptable concentrations of salt, buffering agents, preservatives, compatible carriers, adjuvants, and optionally other therapeutic ingredients. For use in therapy, an effective amount of a composition comprising a recombinant polypeptide inhibitor (e.g., vIRD) can be administered to a subject by any mode that delivers the composition to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, a composition comprising a recombinant polypeptide inhibitor (e.g., vIRD) (including any additional therapeutic agents such as antigens, adjuvants, etc.) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also contemplated are oral dosage forms of a composition comprising a recombinant polypeptide inhibitor (e.g., vIRD). The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For a composition comprising a recombinant polypeptide inhibitor (e.g., vIRD), the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the caspase inhibitor or by release of the biologically active material beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression. Colorants and flavoring agents may all be included. For example, the caspase inhibitor may be formulated (such as by liposome or microsphere encapsulation) and then further contained within an edible product, such as a refrigerated beverage containing colorants and flavoring agents. One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the vIRD compositions either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions provided herein may take the form of tablets or lozenges formulated in conventional manner. For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Also contemplated herein is pulmonary delivery of a composition comprising a recombinant polypeptide inhibitor (e.g., vIRD). The vIRD composition is delivered to the lungs of a mammal while inhaling and traverses across the lung epithelial lining to the blood stream.

Contemplated for use in the practice of this present disclosure are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this present disclosure are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. All such devices require the use of formulations suitable for the dispensing of a composition comprising a recombinant polypeptide inhibitor (e.g., vIRD). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified caspase inhibitor may also be prepared in different formulations depending on the type of chemical modification or the type of device employed.

Formulations suitable for use with a nebulizer, either jet or ultrasonic, will typically comprise caspase inhibitor dissolved in water at a concentration of about 0.1 to 25 mg of biologically active compositions comprising a recombinant polypeptide inhibitor (e.g., vIRD) per mL of solution. The formulation may also include a buffer and a simple sugar (e.g., for caspase inhibitor stabilization and regulation of osmotic pressure). The nebulizer formulation may also contain a surfactant, to reduce or prevent surface induced aggregation of the caspase inhibitor caused by atomization of the solution in forming the aerosol. Formulations for use with a metered-dose inhaler device will generally comprise a finely divided powder containing the caspase inhibitor suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing caspase inhibitor and may also include a bulking agent, such as lactose, sorbitol, sucrose, or mannitol in amounts which facilitate dispersal of the powder from the device, e.g., 50 to 90% by weight of the formulation. The caspase inhibitor should most advantageously be prepared in particulate form with an average particle size of less than 10 mm (or microns), most preferably 0.5 to 5 mm, for most effective delivery to the distal lung. Nasal delivery of a pharmaceutical composition of the present disclosure is also contemplated. Nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present disclosure. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Compositions comprising a recombinant polypeptide inhibitor (e.g., vIRD) of the present disclosure, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compositions comprising a recombinant polypeptide inhibitor (e.g., vIRD) may be in powder form for constitution with a suitable vehicle, e.g., sterile pyrogen-free water, before use. The vIRD compositions may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

Compositions comprising a recombinant polypeptide inhibitor (e.g., vIRD) of the present disclosure can also optionally include other therapeutics and/or antigens and may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the present disclosure contain an effective amount of a composition comprising a recombinant polypeptide inhibitor (e.g., vIRD) and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The vaccines and compositions of the present disclosure may be formulated in a nanoparticle or microparticle. Nanoparticles and microparticles are small discrete particles that may be loaded with, coated with or encapsulate active agents. The nanoparticles and microparticles may be substantially spherical or oblong in shape or may be a mix of different shapes. The term "substantially spherical," as used herein, means that the shape of the particles does not deviate from a sphere by more than about 10%. The nanoparticle or microparticle may be solid or hollow or partially solid or hollow. Nanoparticles typically have a size range in the nanometer scale, i.e., from about 1 nm to about 999 nm or alternatively, from about 1 nm to about 100 nm. The size in some aspects refers to the average or median diameter of a plurality of nanoparticles when a plurality of nanoparticles are intended. Microparticles have a size of 1 micron or greater. Nanoparticles and microparticles may be polymeric particles. Polymeric particles and methods of making polymeric particles are well known in the art. In some embodiments, the particle is comprised of one or more biocompatible materials, e.g., biocompatible polymers, carbohydrates, or proteins, e.g., selected from the group consisting of poly(lactic-co-glycolic acid (PLGA), polyglutamic acid (PG), dextran, hyaluronic acid, poly(citrate), poly(glycerol sebacate), elastin, chitosan, poly(carbonate), poly(hydroxy acids), polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly (butyric acid), poly(valeric acid), and poly(lactide-co-caprolactone), ethylene vinyl acetate, copolymers and blends thereof. In certain embodiments, the biocompatible material is selected from the group consisting of poly(lactic-co-glycolic acid (PLGA), polyglutamic acid (PG) dextran, hyaluronic acid, poly(citrate), poly(glycerol sebacate), and poly(carbonate). Alternatively the particles may be formed by metals or metal oxides, such as Au, Fe, Ti.

A dosing schedule of, for example, once/week, twice/week, three times/week, four times/week, five times/week, six times/week, seven times/week, once every two weeks, once every three weeks, once every four weeks, once every five weeks, and the like, is available for the compositions comprising a recombinant polypeptide inhibitor (e.g., vIRD) of present disclosure. The dosing schedules encompass dosing for a total period of time, for example, of one week, two weeks, three weeks, four weeks, five weeks, six weeks, two months, three months, four months, five months, six months, seven months, eight months, nine months, ten months, eleven months, and twelve months.

Provided are possible cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Compositions comprising a recombinant polypeptide inhibitor (e.g., vIRD) according to the present disclosure may also be administered with one or more additional therapeutic agents (e.g., a vaccine, adjuvant, immunosuppressant, antigen, caspase inhibitor, cytokines, antibodies, etc.). In the instances when the vIRD composition is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the caspase inhibitor are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the compositions comprising a recombinant polypeptide inhibitor (e.g., vIRD). For instance, in a subject at risk of developing a cancer or an infectious disease, the subject may be administered the vIRD composition on a regular basis when that risk is greatest, i.e., after exposure to a cancer-causing agent. Additionally, the vIRD composition may be administered to travelers before they travel to foreign lands where they are at risk of exposure to infectious agents. Similarly, the vIRD composition may be administered to soldiers or civilians at risk of exposure to biowarfare to induce an antigen specific immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites. The term antigen broadly includes any type of molecule which is recognized by a host immune system as being foreign. Antigens include but are not limited to cancer antigens and microbial antigens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of infectious viruses that have been found in humans and are useful for formulating in whole or in part as a microbial antigen include but are not limited to: Retroviridae (e.g. human immunodeficiency viruses, such as HIV-1; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis, hepatitis C; Norwalk and related viruses, and astroviruses).

Gram positive bacteria serving as antigens in vertebrate animals include, but are not limited to, *Pasteurella* species, *Staphylococci species* and *Streptococcus* species. Gram negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* sps. (e.g. *M. tuberculosis, M.*

*avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia, Actinomyces israeli* and *Chlamydia*.

Examples of infectious fungi include: *Cryptococcus neoformans, Histoplasma capsulatum, Coccidioides immitis, Blastomyces dermatitidis, Chlamydia trachomatis* and *Candida albicans*. Other infectious organisms (i.e., protists) include: *Plasmodium* such as *Plasmodium falciparum, Plasmodium malariae, Plasmodium ovale, Plasmodium vivax, Toxoplasma gondii* and *Shistosoma*.

Other medically relevant microorganisms have been descried extensively in the literature, e.g., see C. G. A. Thomas, "Medical Microbiology", Bailliere Tindall, Great Britain 1983, the entire contents of which is hereby incorporated by reference.

Sub-unit vaccines containing anti-microbial antigens and which can be employed as a component of the vaccines are typically recombinant protein-based antigens. Examples of such anti-microbial recombinant protein-based antigens include Borrelia burgdorferi antigens, Hepatitis B protective antigens, Herpes Simplex Virus antigens, Influenza antigens, Congenital cytomegalovirus (CMV) antigens, Tuberculosis antigens, HIV antigens, Diphtheria antigens, Tetanus antigens, Pertussis antigens and Yersinia pestis protective antigens, such as antigens comprising one, two or more antigenic proteins, or an anthrax protective antigen, such as recombinant protective antigen (rPA).

Compositions comprising a recombinant polypeptide inhibitor (e.g., vIRD) of the present disclosure may optionally be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β interferon-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the present disclosure include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Compositions comprising a recombinant polypeptide inhibitor (e.g., vIRD) according to the present disclosure can include other therapeutic agents such as adjuvants to enhance immune responses. These vIRD composition and other therapeutic agent may be administered simultaneously or sequentially. When the other therapeutic agents are administered simultaneously they can be administered in the same or separate formulations, but are administered at the same time. The other therapeutic agents are administered sequentially with one another and with the vIRD composition, when the administration of the other therapeutic agents and the vIRD composition is temporally separated. The separation in time between the administration of these compounds may be a matter of minutes or it may be longer. Other therapeutic agents include but are not limited to adjuvants, cytokines, antibodies, antigens, etc. An adjuvant is any molecule or compound which can stimulate the humoral and/or cellular immune response. Adjuvants include, for instance, adjuvants that create a depo effect, immune stimulating adjuvants, and adjuvants that create a depo effect and stimulate the immune system.

Compositions comprising a recombinant polypeptide inhibitor (e.g., vIRD) according to the present disclosure may also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

In one embodiment, the cancer medicament is a chemotherapeutic agent selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastatin, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate. In an important embodiment, the cancer medicament is taxol.

In another embodiment, the cancer medicament is an immunotherapeutic agent selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf r3, ior c5, BABS, anti-FLK-2, MDX-260, ANA Ab, SMART 1D10 Ab, SMART ABL 364 Ab and ImmuRAIT-CEA.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Co-administration need to refer to administration at the same time in an individual, but rather may include administrations that are spaced by hours or even days, weeks, or longer, as long as the administration of multiple therapeutic agents is the result of a single treatment plan. By way of example, the co-administration may comprise administering compositions comprising a recombinant polypeptide inhibitor (e.g., vIRD) of the present disclosure before, after, or at the same time as the one or more additional therapeutic agents. In one example treatment schedule, the vIRD compositions of the present disclosure may be given as an initial dose in a multi-day protocol, with the one or more additional therapeutic agents given on later administration days; or the one or more additional therapeutic agents given as an initial dose in a multi-day protocol, with the vIRD compositions of the present disclosure given on later administration days. On another hand, one or more additional therapeutic agents and the vIRD compositions of the present disclosure may be administered on alternate days in a multi-day protocol. In still another example, a mixture of the one or more additional therapeutic agents and the vIRD compositions of the present disclosure may be administered to modulate the immune response, inhibit necroptosis, vaccinate the subject, etc. This is not meant to be a limiting list of possible administration protocols.

An effective amount of a one or more additional therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

Formulations of the one or more additional therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

4. Therapeutic Methods

Embodiments of the present disclosure include a method of modulating an immune response in a subject in need thereof that includes administering a recombinant polypeptide inhibitor of at least one inflammatory-modulating protein comprising a plurality of Ankyrin repeat motifs and at least 65% sequence identity with SEQ ID NO: 1. In accordance with these embodiments, inhibition of the at least one inflammatory-modulating protein modulates the immune response in the subject.

In some embodiments of the method, the recombinant polypeptide inhibitor is derived from a poxvirus peptide or polypeptide (e.g., a vIRD peptide or polypeptide), including any derivative or variant thereof. In some embodiments, the poxvirus peptide or polypeptide is derived from a cowpox virus, a ectromelia virus, a monkeypox virus, a variola virus (smallpox), a horsepox virus, a skunkpox virus, a taterapox virus, a camelpox virus, or a volepox virus, or any derivative, variant, or isolate thereof. As would be recognized by one of ordinary skill in the art based on the present disclosure, the recombinant polypeptide inhibitor of an inflammatory-modulating protein can be any other recombinant vIRD peptide or polypeptide derived from a poxvirus, that has less than 100% amino acid identity with a naturally-occurring counterpart peptide or polypeptide.

In some embodiments of the method, the polypeptide inhibitor includes a plurality of Ankyrin repeat motifs. In some embodiments, the polypeptide comprises between 2 and 6 Ankyrin repeat motifs. In some embodiments, the polypeptide comprises between 3 and 6 Ankyrin repeat motifs. In some embodiments, the polypeptide comprises between 4 and 6 Ankyrin repeat motifs. In some embodiments, the polypeptide comprises between 5 and 6 Ankyrin repeat motifs. In some embodiments, the polypeptide comprises at least 5 Ankyrin repeat motifs. In some embodiments, the polypeptide comprises greater than 5 Ankyrin repeat motifs.

In some embodiments of the method, the polypeptide inhibitor has at least 65% sequence identity with SEQ ID NO: 1. In some embodiments, the polypeptide inhibitor has at least 70% sequence identity with SEQ ID NO: 1. In some embodiments, the polypeptide inhibitor has at least 75% sequence identity with SEQ ID NO: 1. In some embodiments, the polypeptide inhibitor has at least 80% sequence identity with SEQ ID NO: 1. In some embodiments, the polypeptide inhibitor has at least 85% sequence identity with SEQ ID NO: 1. In some embodiments, the polypeptide inhibitor has at least 90% sequence identity with SEQ ID NO: 1. In some embodiments, the polypeptide comprises at least 95% sequence identity with SEQ ID NO: 1. In some embodiments, the polypeptide comprises at least 96%, 97%, 98%, or 99% sequence identity with SEQ ID NO: 1. In some embodiments, the polypeptide comprises less than 100% sequence identity with SEQ ID NO: 1.

In some embodiments of the method, the polypeptide includes a F-box motif. In some embodiments, the polypeptide comprises a F-box motif but lacks at least one Ankyrin repeat motif as compared to a naturally-occurring counterpart polypeptide. In some embodiments, the polypeptide comprises a plurality of Ankyrin repeat motifs but lacks an F-box motif as compared to a naturally-occurring counterpart polypeptide. In some embodiments, the polypeptide has at least 65% sequence identity with any of SEQ ID NOs: 1-4. In some embodiments, the polypeptide has at least 70% sequence identity with any of SEQ ID NOs: 1-4. In some embodiments, the polypeptide has at least 75% sequence identity with any of SEQ ID NOs: 1-4. In some embodiments, the polypeptide has at least 80% sequence identity with any of SEQ ID NOs: 1-4. In some embodiments, the polypeptide has at least 85% sequence identity with any of SEQ ID NOs: 1-4. In some embodiments, the polypeptide has at least 90% sequence identity with any of SEQ ID NOs: 1-4. In some embodiments, the polypeptide has at least 95% sequence identity with any of SEQ ID NOs: 1-4. In some embodiments, the polypeptide comprises at least 96%, 97%, 98%, or 99% sequence identity with any of SEQ ID NOs: 1-4. In some embodiments, the polypeptide comprises less than 100% sequence identity with any of SEQ ID NOs: 1-4. In some embodiments, the polypeptide comprises any one of SEQ ID NOs: 1-4. In some embodiments, the polypeptide comprises at least one amino acid substitution that is not present in any one of SEQ ID NOs: 1-4.

In some embodiments of the method, the polypeptide has at least 65% sequence identity with any of SEQ ID NOs: 5-12. In some embodiments, the polypeptide has at least 70% sequence identity with any of SEQ ID NOs: 5-12. In some embodiments, the polypeptide has at least 75% sequence identity with any of SEQ ID NOs: 5-12. In some embodiments, the polypeptide has at least 80% sequence identity with any of SEQ ID NOs: 5-12. In some embodiments, the polypeptide has at least 85% sequence identity with any of SEQ ID NOs: 5-12. In some embodiments, the polypeptide has at least 90% sequence identity with any of SEQ ID NOs: 5-12. In some embodiments, the polypeptide has at least 95% sequence identity with any of SEQ ID NOs: 5-12. In some embodiments, the polypeptide comprises at least 96%, 97%, 98%, or 99% sequence identity with any of SEQ ID NOs: 5-12. In some embodiments, the polypeptide comprises less than 100% sequence identity with any of SEQ ID NOs: 5-12. In some embodiments, the polypeptide comprises any one of SEQ ID NOs: 5-12. In some embodiments, the polypeptide comprises less than 100% sequence identity with any one of SEQ ID NOs: 1 and 5-12. In some embodiments, the polypeptide comprises at least one amino acid substitution that is not present in any one of SEQ ID NOs: 1 and 5-12.

In some embodiments of the method, the inflammatory-modulating protein(s) that is inhibited by the recombinant polypeptide inhibitor (e.g., vIRD) includes one or more of receptor interacting protein kinase-1 (RIPK1), receptor interacting protein kinases-3 (RIPK3), TIR-domain-containing adapter-inducing interferon-β (TRIF), Z-DNA binding protein 1 (ZBP1), Cullin-1 (CUL1), and/or S-phase kinase associated protein 1 (SKP1). In some embodiments, the polypeptide binds to one or more of RIPK1, RIPK3, TRIF, ZBP1, CUL1, and/or SKP1, such that the binding of the polypeptide inhibits expression, activity, and/or promotes degradation of RIPK1, RIPK3, TRIF, ZBP1, CUL1, and/or SKP1.

In accordance with these embodiments, the method includes modulating an immune response in a subject. In some embodiments, the method comprises enhancing expression and/or activity of one or more genes, including but not limited to, C-C motif chemokine ligand 2 (Ccl2), C-C motif chemokine ligand 4 (Ccl4), C-X-C motif chemokine ligand 1 (Cxcl1), C-X-C motif chemokine ligand 2 (Cxcl2), and Interleukin 6 (Il6). In some embodiments of the method, modulating an immune response in a subject involves attenuating expression and/or activity of one or more genes, including but not limited to, C-C motif chemokine ligand 8 (Ccl8), Arachidonate 15-lipoxygenase (Alox15), Complement C3 (C3), Prostaglandin-endoperoxide synthase 1 (Ptgs1), and Arginase 1 (Arg1). In some embodiments of the method, modulating an immune response in a subject comprises inhibiting expression of at least one gene controlled by Nuclear Factor kappa B (NF-κB).

In accordance with these embodiments, the method includes modulating an immune response in a subject to treat at least one inflammatory symptom associated with an autoinflammatory disease. In some embodiments, the autoinflammatory disease includes, but is not limited to, rheumatoid arthritis, inflammatory bowel disease, skin inflammation, atopic dermatitis, and systemic lupus erythematosus.

The compositions according to the present disclosure may be used in various methods, as described further herein. The methods of the present disclosure may be performed in vitro, ex vivo, or in vivo. In some embodiments, the present disclosure provides a method of inhibiting necroptosis in a cell, the method comprising, consisting of, consisting essentially of contacting the cell a therapeutically effective amount of a recombinant polypeptide inhibitor (e.g., vIRD) according to the present disclosure such that the necroptosis is inhibited in the cell.

In some embodiments, the present disclosure provides a method of inhibiting necroptosis in a subject, the method comprising, consisting of, consisting essentially of contacting the cell a therapeutically effective amount of a recombinant polypeptide inhibitor (e.g., vIRD) according to the present disclosure such that the necroptosis is inhibited in the subject. In some embodiments, the present disclosure provides a method of modulating the immune response in a subject comprising, consisting of, consisting essentially of administering to the subject a therapeutically effective amount of a recombinant polypeptide inhibitor (e.g., vIRD) according to the present disclosure such that the immune system is modulated in the subject. In some embodiments, the present disclosure provides a method vaccinating a subject against an infectious disease or cancer, the method comprising, consisting of, or consisting essentially of administering to the subject a therapeutically effective amount of a recombinant polypeptide inhibitor (e.g., vIRD) according to the present disclosure such that the subject is vaccinated.

In some embodiments, the present disclosure provides a method of treating a subject suffering from an infectious disease and/or cancer, the method comprising, consisting of, or consisting essentially of administering to the subject a therapeutically effective amount of a recombinant polypeptide inhibitor (e.g., vIRD) according to the present disclosure such that the subject is treated. A subject having an infection is a subject that has been exposed to an infectious pathogen and has acute or chronic detectable levels of the pathogen in the body. The vIRD compositions of the present disclosure can be used with or without an antigen or other additional therapeutic agent to mount an antigen specific immune response that is capable of reducing the level of or eradicating the infectious pathogen. An infectious disease, as used herein, is a disease arising from the presence of a foreign microorganism in the body.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment, the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

In some embodiments, the methods further comprise administering to the subject one or more additional therapeutic agents. In some embodiments, the additional agent comprises an antigen. In another embodiment, the additional agent comprises an adjuvant. In one embodiment, the antigen and vIRD are separate components. In another embodiment, the antigen and vIRD are a single component.

5. MATERIALS AND METHODS

Mice. All experimental procedures are approved by the Duke Institutional Animal Care and Use Committee. Generation of wild type Ripk3 -gfp$^{f/f}$ and Ripk3$^{\Delta R/\Delta R}$ mice have been described (Moriwaki et al., 2017). Male and female mice 8-10 weeks of age were infected intraperitoneally with $1 \times 10^6$ pfu of wild type CPXV-GFP or CPXV-ΔvIRD-GFP. Spleen, visceral fat pad, liver and peritoneal exudate cells (PECs) were harvested 3.5 days post-infection. Viral titers were determined by plaque assays using Vero cells and crystal violet staining as described before (Chan et al., 2003).

Transfection of DNA Plasmids and siRNA screen. For plasmid transfections, HEK293T cells (cultured in the high glucose version of Dulbecco's modified Eagle medium (DMEM) supplemented with 10% heat-inactivated fetal bovine serum, 2 mM glutamine, 10 mM HEPES (pH 7.2), 1× non-essential amino acids solution, 100 U ml$^{-1}$ penicillin and 100 μg ml$^{-1}$ streptomycin) were transfected with the indicated plasmids using the TransIT®-LT1 Transfection Reagent (Mirus, MIR2300). After 24 hours, cells were lysed with RIPA lysis buffer supplemented with Complete Protease inhibitors (Roche) and phosphatase inhibitor cocktail (Sigma). For siRNA screen, L929 cells were seeded at $2.5 \times 10^5$ cells per well on 12-well plate and transfected with 50 nM of siRNA with lipofectamine RNAiMax reagent as per manufacturer's protocol (Invitrogen). Twenty-four hours later, cells were infected with CPXV at moi=2. Six hours later, whole cell lysates were harvested for Western blot analysis. (The siRNA sequences can be provided upon request.)

Virus infection and cell death assays. Unless otherwise stated, cells were infected with viruses at moi=2. Cells were incubated with virus in DMEM (Colo205 and L929) or RPMI 1640 (TNFR2$^+$, FADD-deficient Jurkat (clone 142), TNFR2$^+$, Caspase 8-deficient Jurkat (clone J3.2), wild type TNFR2$^+$ Jurkat cells (clone 4E3)) medium supplemented with 2.5% fetal calf serum for 2 hours before changing to medium with 10% fetal bovine serum. For MEFs, cells were treated with 10 ng/ml TNF 16 hours post-infection. For FIG. 1 and FIG. 8, cell death was determined by propidium iodide in the infected (GFP+) and uninfected (GFP-) cells. Cell death was calculated using the formula:

$$\left(1 - \left(\frac{\text{\# cells in treated sample}}{\text{\# cells in untreated control sample}}\right)\right) * 100\%.$$

For Incucyte imaging, infected cells were treated with the TNF neutralizing antibody (R&D Systems, MAB4101 at 10 μg/ml), MLN4924 (APExBIO, 1 μM), GSK'963 (kind gift of GSK, 1 μM), GSK'872 (kind gift of GSK, 1 μM), Necls (APExBIO, 1 μM) or zVAD-fmk (APExBIO, 5 μM). Cell death was measured using 100 μM Cytotox Green (Essen Bioscience #4633) or 100 μM Cytotox Red (Essen Bioscience #4632).

Real time-PCR and Nanostring. Total RNA was isolated from visceral fat pads with RNeasy kit from Qiagen. cDNA was generated using iScript Reverse Transcription Supermix (Bio-Rad), real time-PCR was performed using iQ SYBR Green Supermix (Bio-Rad). Chemokine expression level was normalized to the internal control Tbp1. The primers for the Q-PCR reactions are:

```
Ccl2:
                                     (SEQ ID NO: 13)
5'-AGGTGTCCCAAAGAAGCTGTA-3', (SEQ ID NO: 14)
5'-ATGTCTGGACCCATTCCTTCT-3';

Cxcl2:
                                     (SEQ ID NO: 15)
5'-GAGCTTGAGTGTGACGCCCCAGG-3', (SEQ ID NO: 16)
5'-GTTAGCCTTGCCTTTGTTCAGTATC-3';

Ccl4:
                                     (SEQ ID NO: 17)
5'-TTGCTCCTCACGTTCAGATTTC-3', (SEQ ID NO: 18)
5'-GGAGACACGCGTCCTATAACTA-3';

Il6:
                                     (SEQ ID NO: 19)
5'-CGGAGAGGAGACTTCACAGA-3', (SEQ ID NO: 20)
5'-CCAGTTTGGTAGCATCCATC-3';

Tbp1:
                                     (SEQ ID NO: 21)
5'-CAAACCCAGAATTGTTCTCCTT-3', (SEQ ID NO: 22)
5'-ATGTGGTCTTCCTGAATCCCT-3'.
```

For Nanostring analysis, 300 ng of RNA was used per reaction using the nCounter Mouse Immunology v1 Gene Expression Panel. nSolver 3.0 software was used for background subtraction, normalization, and data analysis.

Recombinant and mutant viruses. Wild type, CPXV-LvIRD (Brighton Red strain) and Myxoma virus (Lausanne strain) have been previously described (Mohamed et al., 2009b). Vaccinia virus (Western Reserve strain) was used in FIG. 1. Recombinant VACV expressing wild type or mutant vIRD were generated using the small plaque/large plaque selection system in the vRB12 strain (Blasco and Moss, 1995). Large plaques were picked and subjected to three rounds of freeze/thaw. Recombinants viruses were selected and passaged for 3 rounds in BS-C-1 cells to obtain monoclonal clones. The resulting virus stocks were titrated on either BS-C-1 cells or Vero cells. Ectromelia virus (ECTV) was obtained from ATCC (VR-1374).

Immunoprecipitation and Western blot. For immunoprecipitations (IPs), HEK293T cells and L929 cells were plated at $2.5 \times 10^6$ cells per 10 cm or 15 cm dish, respectively. Cell lysates were prepared using RIPA lysis buffer (25 mM Tris-Cl, 150 mM NaCl, 0.5 mM EDTA, 0.1% SDS, 0.5% Sodium deoxycholate) containing protease and phosphatase inhibitors (Sigma). Insoluble material was removed via centrifugation at 15000 rpm, 15 min, 4° C. and supernatants mixed with 30 µl of magnetic beads (Sigma) and incubated overnight at 4° C. Beads were washed extensively with low and high salt wash buffer prior to boil in 2×SDS Laemmli lysis buffer for western blot analyses. Protein concentrations were determined with the BCA Protein Assay (Pierce). Antibodies for Western blot used in the study include: mRIPK3 (ProSci #2283 and Genentech PUR135347), RIPK1 (BD #610459), ZBP1 (Adipogen AG-208-0010), CUL1 (Life Technologies #718700), MLKL (EMD Millipore, MABC604), HSP90 (BD Bioscience #610418), K48-linked ubiquitin (CST #4289), Caspase 8 (Prosci #3473), FADD (Abcam, ab124812), c-Myc (Invitrogen, MA1-980-HRP), SKP1 (BD Bioscience #610530), TRIF (Genentech PUR136257), GFP (Santa Cruz sc-7868), FLAG (Sigma F3165, ThermoFisher A36797), β-actin (Prosci #3779), HA (Invitrogen #26183), mCherry (Invitrogen M11217). The rabbit anti-CPXV006 antibody (PAS21389) was generated using the peptide (CDYHLKSMLYGKNHYKHYPY (SEQ ID NO: 23)) as immunogen. The anti-human RIPK3 antibody has been described (Cho et al., 2009).

Flow cytometry analysis. Both splenocytes and peritoneal exudate cells (PECs) were stained with the indicated antibodies for flow cytometric analysis on a BD FACSCanto™ II. Cells were released from the spleen by physical disruption using glass slides. Red blood cells were lysed with ACK lysis buffer (150 mM $NH_4Cl$, 10 mM $KHCO_3$, 0.1 mM EDTA). Splenocytes were filtered and subjected to flow cytometric analysis. To harvest peritoneal exudate cells (PECs), peritoneal cavity was flushed with 5 ml DPBS. PECs were lysed with ACK lysis buffer and subjected to flow cytometric analysis. Prior to staining with primary antibodies, cells were incubated with anti-Fc receptor 2.4G2 antibody for 10 minutes. The following indicated antibodies were used, including CD16/CD32 (FcγRII/III; Clone 2.4G2), CD3E (Clone 145-2C11), F4/80 (Clone BM8), CD11b (Clone M1/70), CD11c (Clone N418), Ly6c (Clone HK1.4). Cells were analyzed by BD FACSCantoTM II. Data were analyzed with Flowjo (Treestar) and graphed using Prism 8 software (Graphpad).

Histology. Visceral fat pad was fixed in 10% Neutral Buffered Formalin (Leica Biosystems), embedded in paraffin and cut in 5 µm sections. Tissue sections were stained with H&E. Stained sections were scanned with Leica DMD108.

Statistical analysis. Mean+/−SEM were shown. Unpaired Student's t tests were used.

6. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Cowpox Virus Actively Inhibits Necroptosis. VACV is a laboratory adapted poxvirus that sensitizes infected cells to necroptosis (Cho et al., 2009). However, it is not clear if sensitization to necroptosis is the norm for other poxviruses. To interrogate whether naturally occurring poxviruses also sensitize cells to necroptosis, mouse embryonic fibroblasts (MEFs) were infected with different recombinant poxviruses expressing GFP. Uninfected MEFs are relatively resistant to TNF-induced cytotoxicity. Consistent with previous observations, infection with recombinant VACV (rVACV) expressing GFP rendered MEFs highly sensitive to TNF-induced necroptosis (FIG. 1A; FIG. 8A). Similar sensitization to necroptosis was also observed with the distantly related leporipoxvirus MYXV (FIG. 8A).

By contrast, MEFs infected with recombinant CPXV were completely resistant to TNF-induced necroptosis (FIG. 1A and FIG. 8A). Similarly, VACV and MYXV, but not CPXV, induced necroptosis in murine L929 cells (FIG. 8B). Because uninfected MEFs are not very sensitive to necroptosis, the results in MEFs could be due to failure of CPXV to prime cells for necroptosis. To rule out this possibility, similar experiments were performed in Caspase 8-deficient and FADD-deficient Jurkat cells, which readily undergo necroptosis in response to TNF. In these cells, CPXV, but not VACV, significantly inhibited TNF-induced necroptosis (FIGS. 8C-8E). Similar protection against necroptosis was also observed in CPXV-infected wild type TNFR2$^+$ Jurkat cells treated with TNF or TNF and Smac mimetic (FIGS. 8F-8G). These data demonstrate that CPXV actively inhibits necroptosis in different cell types.

Example 2

Figures 9A, 9B, 9C, 9D, 9E:
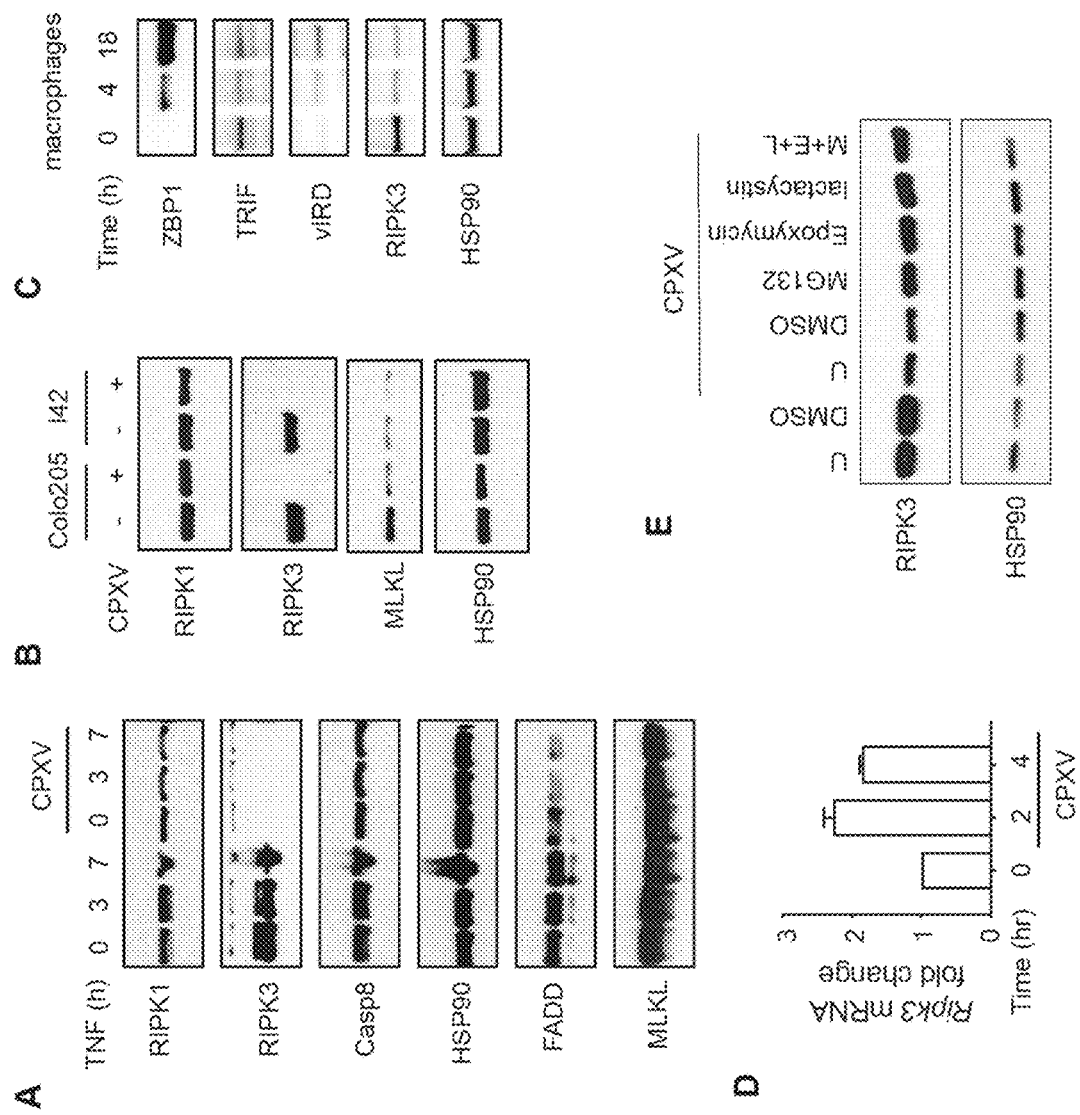

Cowpox Virus Induces Proteasomal Degradation of RIPK3. The murine fibrosarcoma L929 expresses high level of RIPK3 and is widely used to study necroptosis. The mechanism by which CPXV confers necroptosis resistance was examined, and it was found that RIPK3 protein expression was completely abolished in CPXV-infected, but not in MYXV- or VACV-infected L929 cells (FIG. 1B). In contrast, expression of other apoptosis or necroptosis adaptors including RIPK1, MLKL, FADD and caspase 8 was not affected (FIG. 1B and FIG. 9A). CPXV-induced RIPK3 protein disappearance was also observed in other human and mouse transformed cells (FIG. 9B), as well as primary bone marrow derived macrophages (FIG. 9C).

Poxviruses are known to inhibit transcription of certain host anti-viral genes (Harte et al., 2003; Myskiw et al., 2009; Sumner et al., 2014). However, Ripk3 mRNA was not reduced, but rather increased slightly in CPXV-infected cells (FIG. 9D). Kinetics analysis revealed that the loss of RIPK3 protein expression was apparent between 4-6 hours post-infection (FIG. 1C). This rapid kinetics without the loss of gene transcription suggests that proteolysis is involved.

Different protease inhibitors were tested, and it was found that RIPK3 expression in CPXV-infected cells was significantly rescued by proteasome inhibitors such as MG132 or lactacystin (FIG. 1D; FIG. 9E). By contrast, other protease inhibitors had no effects on virus-induced RIPK3 protein loss (FIG. 1D). Since proteasome activity is required for optimal late poxviral gene expression (Satheshkumar et al., 2009; Teale et al., 2009), the rescue of RIPK3 expression by MG132 could be due to blockade of late poxviral gene expression. To determine this, late poxvirus gene expression was inhibited with the DNA synthesis inhibitor AraC (Weir and Moss, 1984). Although AraC modestly rescued RIPK3 protein expression, it was not as effective as MG132 (FIG. 1E). Furthermore, K48-linked RIPK3 ubiquitination was greatly increased in response to CPXV infection (FIG. 1F). These data demonstrate that late gene transcription did not contribute significantly to the disappearance of RIPK3 protein expression. Rather, CPXV infection induces proteasome-mediated degradation of RIPK3.

Figures 2A, 2B, 2C, 2D, 2E, 2F:
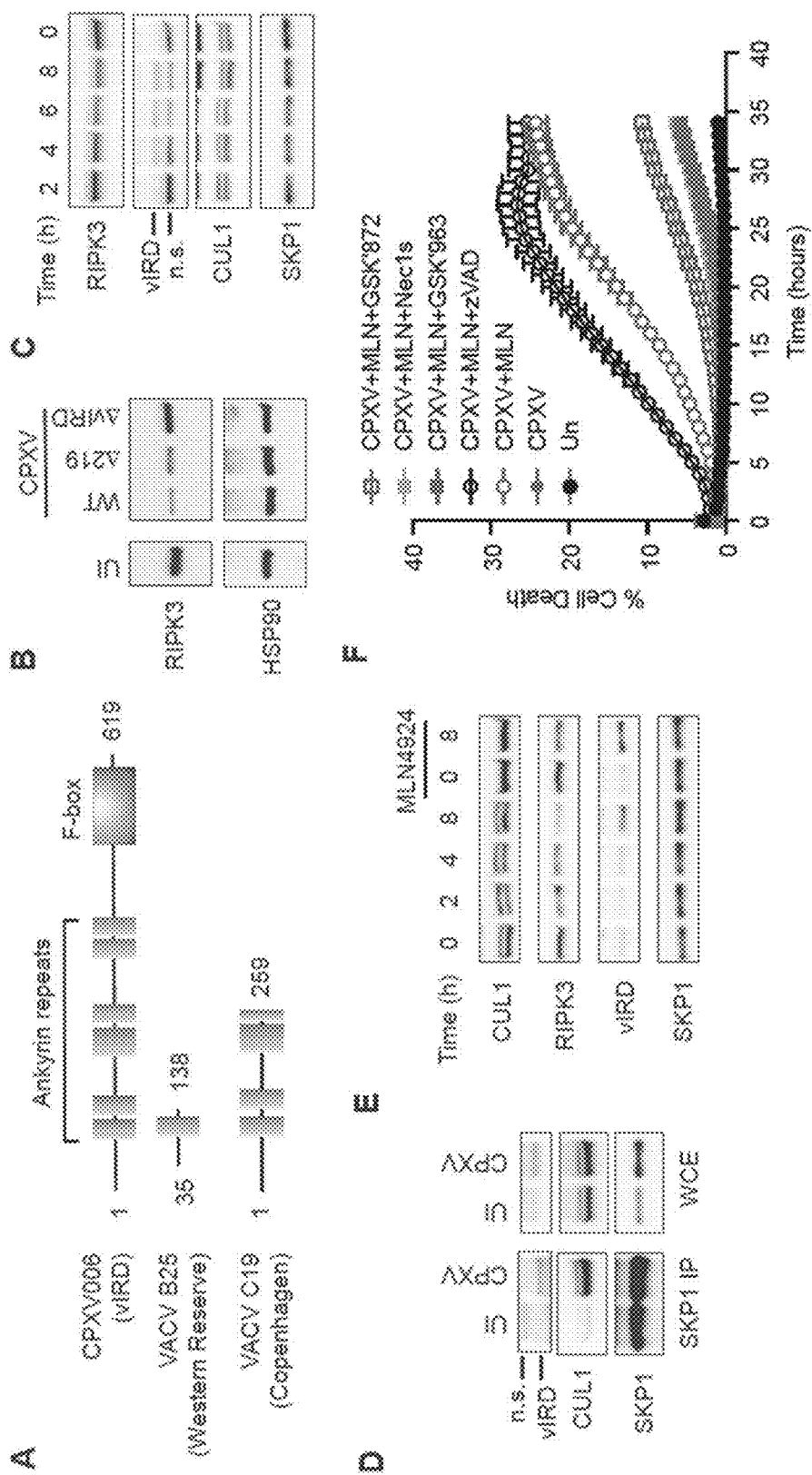

Example 3 siRNA Screen Identified Viral Inducer of RIPK3 Degradation (vIRD). When compared to other naturally occurring orthopoxviruses, the genome of VACV contains large segments of deletions and many fragmented genes in the inverted terminal repeats, a region that encodes many immune modulatory genes (Sanchez-Sampedro et al., 2015). It was postulated that CPXV might encode a "viral inducer of RIPK3 degradation" (vIRD) to promote RIPK3 degradation and necroptosis resistance. To this end, the CPXV genome was surveyed and the analysis identified genes that are either missing, significantly deleted or fragmented in VACV. The query returned 53 "unique" CPXV genes that matched the criteria (less than 60% identity with over 80% coverage, E value<0.0001). A focused siRNA screen was performed against these genes and used Western blot to determine the extent to which the siRNAs would reverse CPXV-induced RIPK3 degradation. One of the most prominent hits from the screen was CPXV006, which encodes a protein with six ankyrin repeats at the N-terminus and a C-terminal F-box (FIG. 2A). Deletion of CPXV006, but not the unrelated CPXV219, fully prevented CPXV-induced RIPK3 degradation (FIG. 2B). A polyclonal antibody against vIRD was generated, and it was found that its expression was detected as early as 4 hours post-infection (FIG. 2C), which tracked with the kinetics of when RIPK3 degradation became apparent (FIGS. 1C and 2D). The CPXV006 orthologues in the Western Reserve and Copenhagen strains of VACV are truncated and missing the C-terminal F-box (FIG. 2A), while other VACV strains lack vIRD orthologues that exhibit high level of sequence identity (https://4virology.net/). These data demonstrate that CPXV006 is the bona fide vIRD that promotes RIPK3 degradation.

Figures 10A, 10B, 10C, 10D:
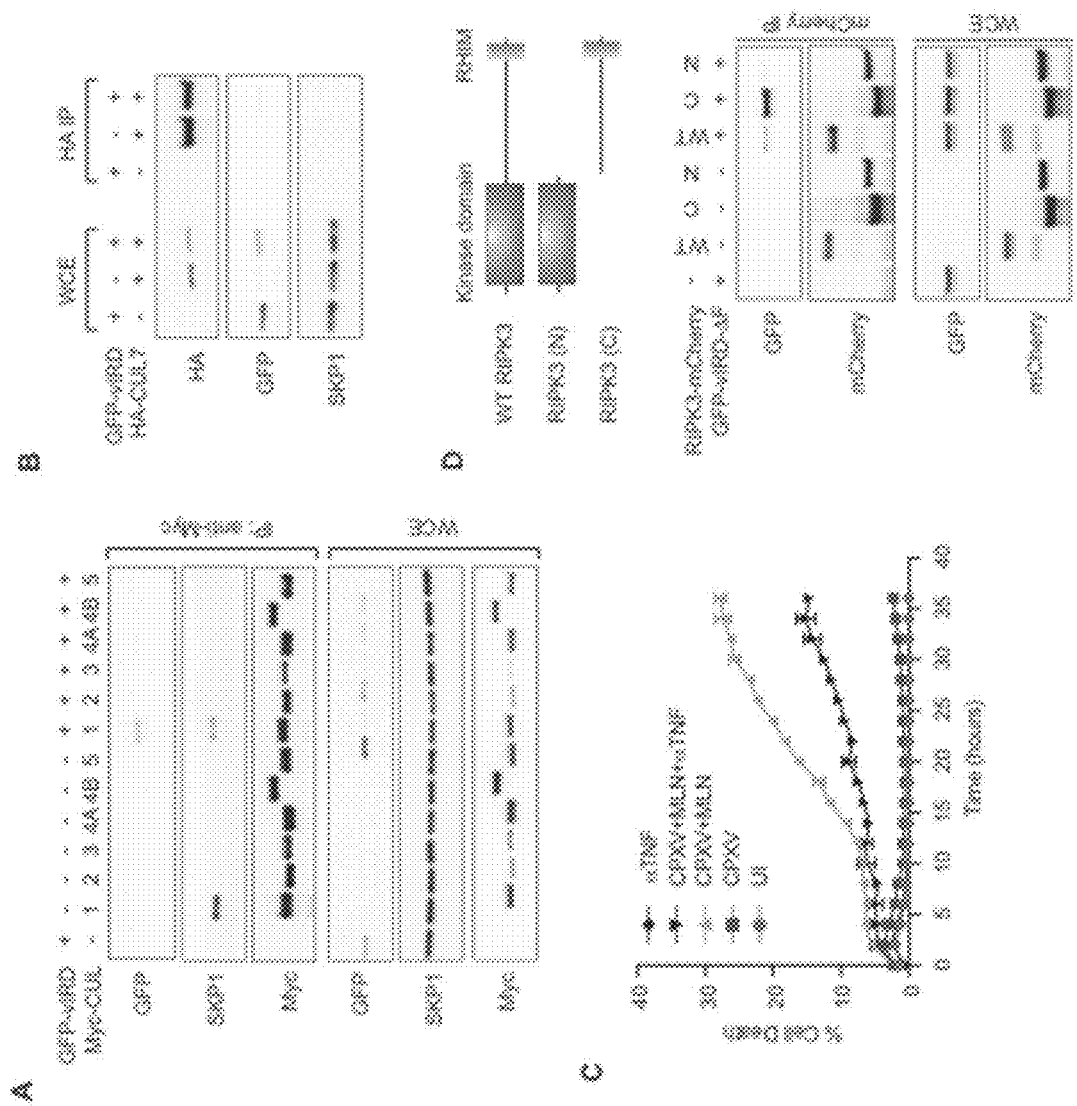

Example 4 vIRD Co-opts the Cellular SCF Machinery to Promote RIPK3 Degradation. Mammalian F-box proteins function as "bridge" to recruit protein substrates to the SKP1-Cullin1-F box (SCF) complex, a multi-subunit complex that promotes protein ubiquitination and proteasome degradation (Lee and Diehl, 2014). It was therefore postulated that vIRD interacts with the cellular SCF complex to mediate RIPK3 degradation. Indeed, CPXV infection induced specific interaction between vIRD, SKP1 and CUL1 (FIG. 2D). Similar interaction between vIRD, SKP1 and CUL1, but not with other mammalian Cullins, was confirmed in HEK293T cells (FIGS. 10A-10B).

SCF activity is activated by CUL1 neddylation (Enchev et al., 2015). To determine if components of the SCF complex are required for virus-induced RIPK3 degradation, the neddylation inhibitor MLN4924 was used. It was found that MLN4924 effectively converted all cellular CUL1 into the fast-migrating inactive de-neddylated form and rescued CPXV-induced RIPK3 degradation (FIG. 2E). CPXV infection did not trigger cell death of L929 cells (FIG. 10C). Surprisingly, MLN4924 induced rapid death of CPXV-infected L929 cells (FIG. 2F and FIG. 10C). Neutralizing TNF antibody partially inhibited CPXV and MLN4924-induced cell death (FIG. 10C), indicating that autocrine TNF was at least partially responsible for the virus-induced cell death. Virus-induced cell death in the presence of MLN4924 was fully inhibited by the RIPK1 kinase inhibitors GSK'963 and Necls, and the RIPK3 kinase inhibitor GSK'872. By contrast, the caspase inhibitor zVAD-fmk had minimal effects on necroptosis induced by CPXV and MLN4924 (FIG. 2F). Thus, during CPXV infection, vIRD co-opts the host SCF machinery to trigger RIPK3 degradation, thereby inhibiting TNF-, RIPK1-, and RIPK3-induced necroptosis.

Figures 3A, 3B, 3C:
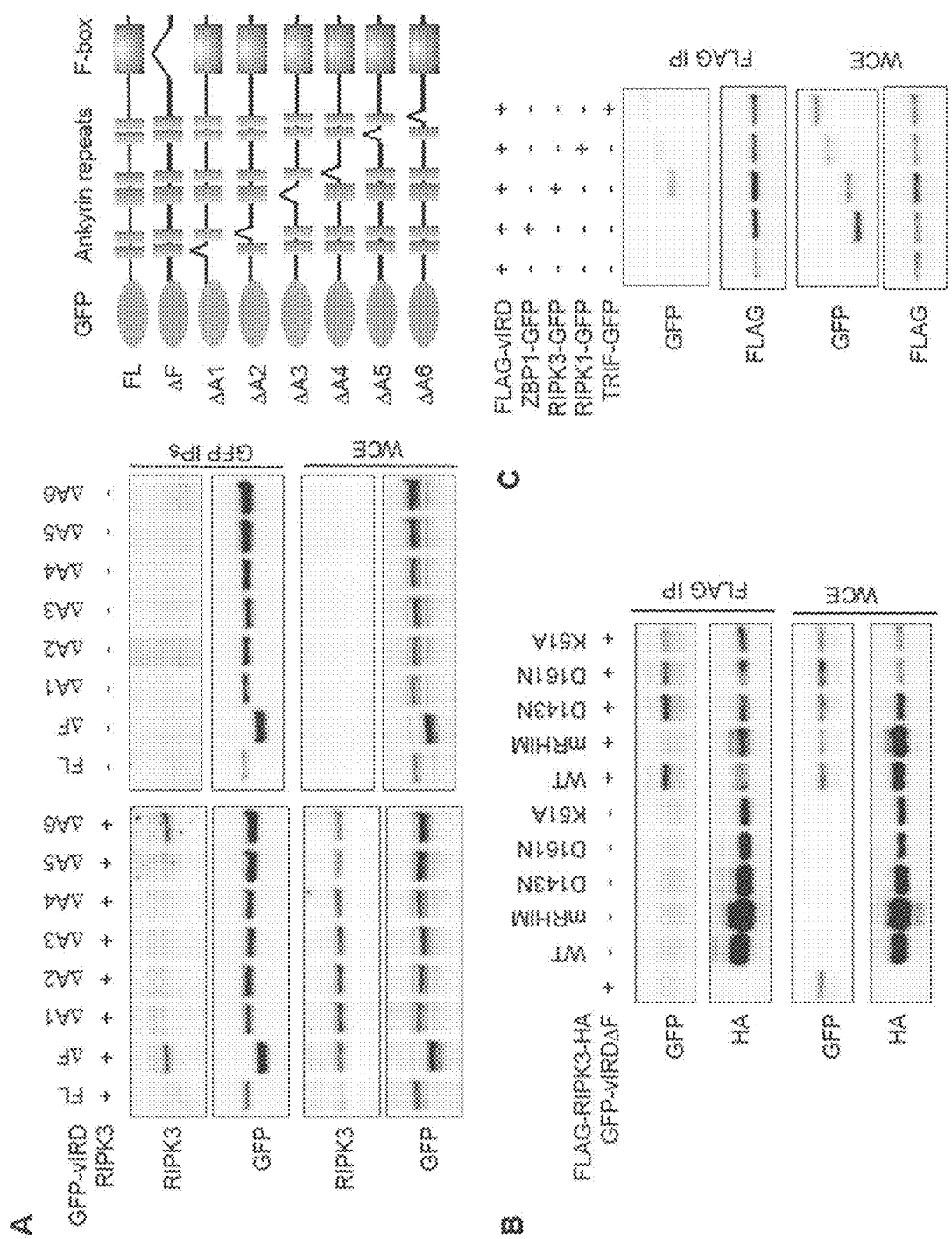

Example 5 vIRD binds to RIPK3 via the ankyrin repeats. F-box adaptors interact with SKP1 to recruit substrates to the SCF complex. Deletion of the F-box abolished vIRD-induced RIPK3 degradation in HEK293T cells (FIG. 3A, compare the first two lanes). By contrast, F-box deletion did not affect vIRD binding to RIPK3 (FIG. 3A), suggesting that vIRD interacts with RIPK3 via its N-terminal ankyrin repeats. Indeed, deletion of each of the first five ankyrin repeats abolished RIPK3 binding and vIRD-induced RIPK3 degradation (FIG. 3A). The RHIM is critical for mediating homotypic interaction among RHIM-containing signal adaptors (Li et al., 2012). Surprisingly, mutation of the tetra-peptide core RHIM sequence abolished RIPK3 binding to vIRD (FIG. 3B). Consistent with these results, the C-terminal fragment of RIPK3 encompassing the RHIM was sufficient to mediate binding to vIRD (FIG. 10D). In contrast, mutations of the kinase active site residues (D143, D161 and K51) did not affect vIRD-RIPK3 binding (FIG. 3B). Thus, vIRD and RIPK3 bind to each other through a previously unknown mode of interaction. Since other RHIM-containing adaptors such as RIPK1, TRIF and ZBP1 did not interact with vIRD or undergo degradation in response to CPXV infection (FIG. 3C and FIGS. 9A-9C), the RHIM is necessary but not sufficient to mediate vIRD targeting of RIPK3.

Figures 4A, 4B, 4C, 4D, 4E, 4F:
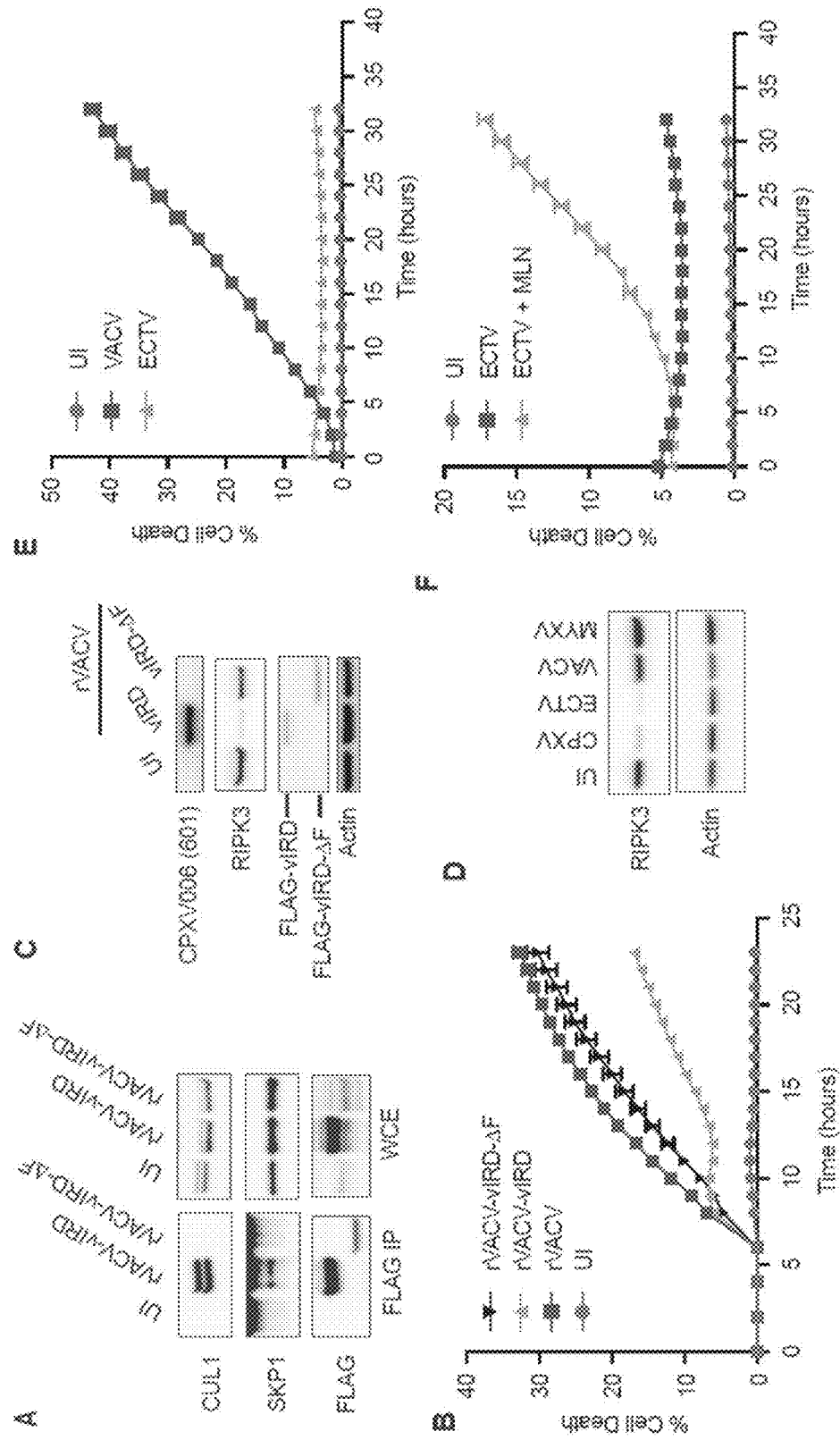

Example 6 vIRD reverses VACV-induced necroptosis sensitivity. To further test whether the loss of an intact vIRD underlies the sensitization of VACV-infected cells to necroptosis, recombinant VACV expressing FLAG-tagged or GFP-tagged wild type or F-box deleted vIRD constructs were generated. As in the case of CPXV, infection of rVACV-vIRD stimulated the assembly of the vIRD-SKP1-CUL1 complex (FIG. 4A). Moreover, while control rVACV readily triggered necroptosis in L929 cells (FIGS. 4B and 11A), rVACV-vIRD greatly reduced RIPK3 protein expression and virus-induced necroptosis (FIGS. 4C-4D). Furthermore, rVACV-vIRD-ΔF failed to induce RIPK3 degradation or necroptosis resistance (FIGS. 4C-4D). Thus, vIRD expression is sufficient to reverse necroptosis sensitivity of VACV-infected cells.

Example 7

Figures 11A, 11B, 11C, 11D:
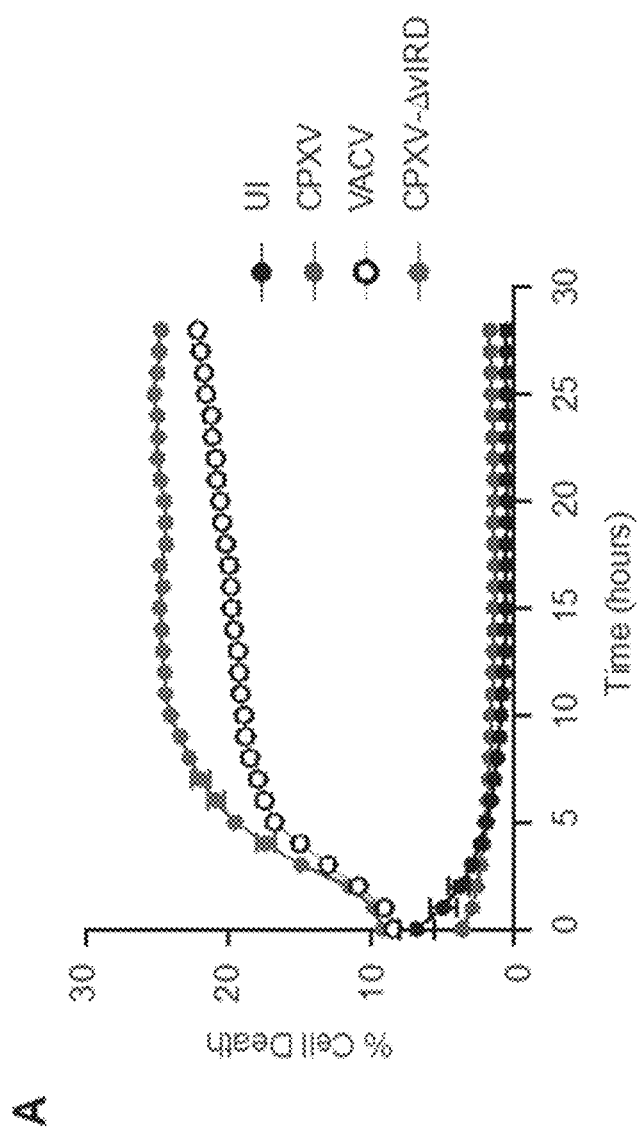
Figures 11A, 11B, 11C, 11D:
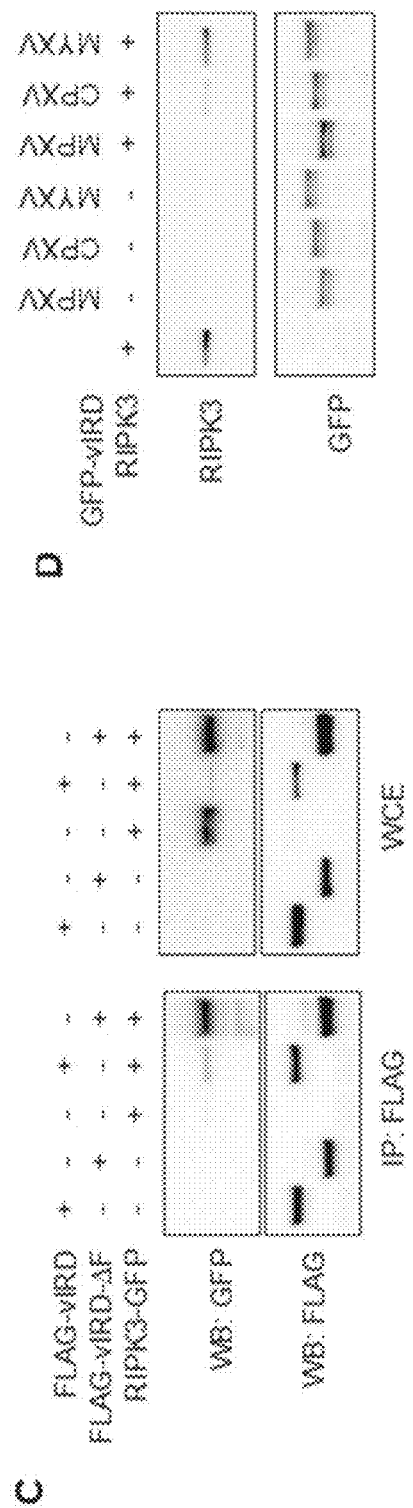

Conservation of vIRD in other orthopoxviruses. The divergent effect of CPXV and VACV on necroptosis prompted questioning of whether necroptosis inhibition by vIRD is a common strategy employed by other poxviruses. The genomes of orthopoxviruses were queried, and it was found that the majority of them encode highly conserved vIRD orthologues (FIG. 11B). Similar to CPXV, ectromelia virus (ECTV) also induced RIPK3 degradation (FIG. 4D). Moreover, ectopic expression of the vIRD orthologues from ECTV and Monkeypox virus (MPXV) both induced RIPK3 degradation (FIGS. 11C-11D). Furthermore, deletion of the F-box from the ECTV-vIRD also abolished RIPK3 degradation (FIG. 11C). These results indicate that with the exception of VACV, vIRD is a highly conserved immune inhibitory mechanism within the orthopoxvirus genus.

In contrast to orthopoxviruses, the related leporipoxvirus MYXV did not confer necroptosis resistance (FIG. 8A). Interestingly, the closest vIRD-like orthologue in MYXV encoded by the m148R gene contains 8 ankyrin repeats with only ~30% sequence identity when compared to the vIRDs from CPXV, MPXV and ECTV. Moreover, the MYXV vIRD orthologue lacks a F-box at the C-terminus and did not trigger RIPK3 degradation (FIG. 11D). Similar to MYXV, ankyrin repeats-containing adaptors in the avipoxvirus genus also exhibit poor sequence homology to the orthopoxvirus vIRDs (~30-40%), which is consistent with the fact that their hosts largely lack RIPK3 expression. Thus, vIRD-mediated RIPK3 degradation is a strategy specifically employed by most orthopoxviruses to evade host cell necroptosis.

Figures 12A, 12B:
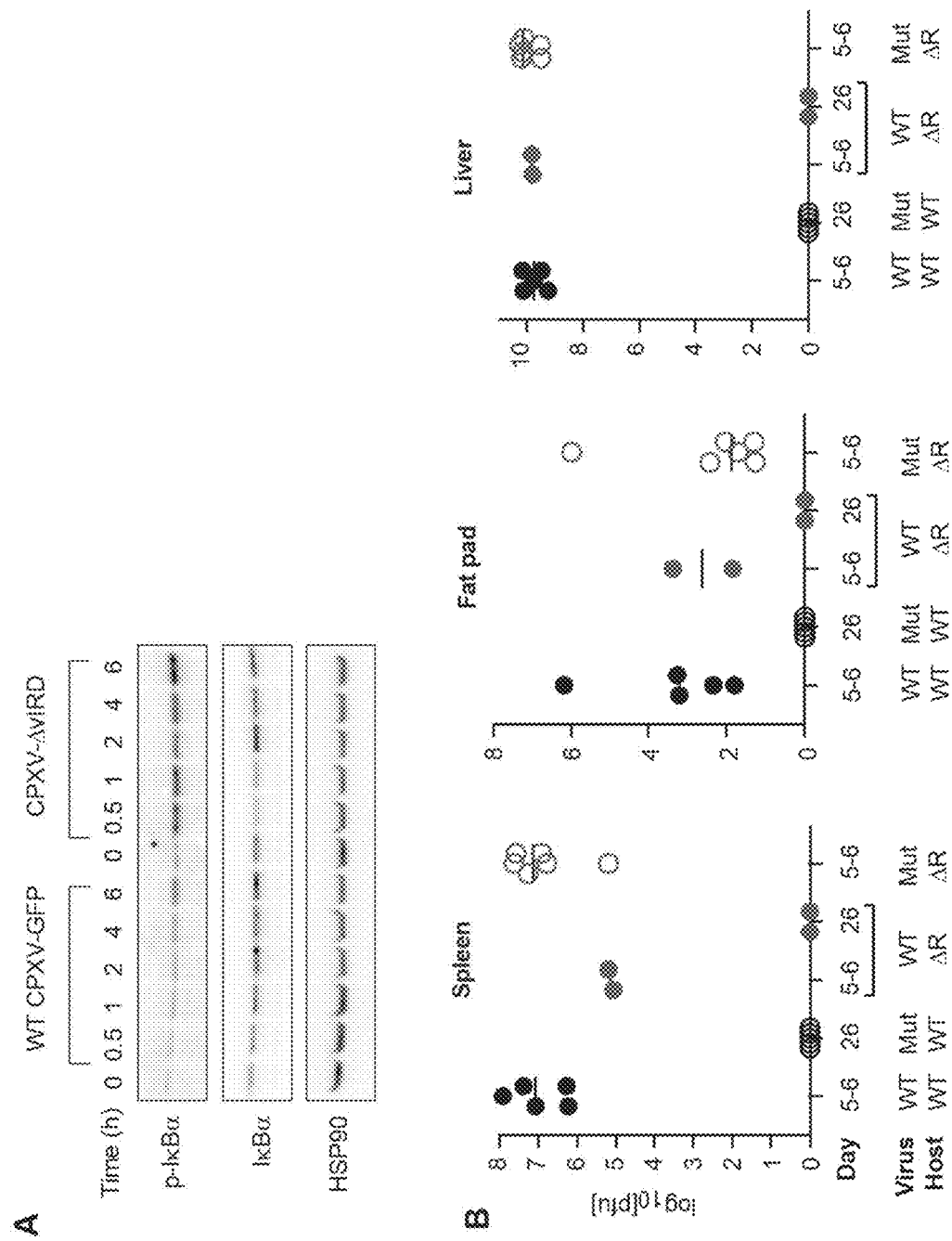

Example 8 vIRD Targets RIPK3 to Promote Pathogenesis. The loss of vIRD in VACV prompted an examination of whether it might contribute to viral pathogenesis. The role of vIRD in CPXV infection in mice was first determined. Three and a half day post-infection, viral load in wild type CPXV-infected mice was much greater than that of CPXV-ΔvIRD infected mice (FIG. 5A), which is consistent with the previous observation that RIPK3 deficiency greatly enhanced VACV replication in vivo. Since vIRD might also disrupt proteasomal degradation of normal SCF complex substrates such as IkBa, the changes in viral replication could be due to effects on NF-κB activation. Indeed, consistent with previous observation, it was found that loss of vIRD increased CPXV-induced phosphorylation and degradation of IkBa (FIG. 12A).

Figures 5A, 5B, 5C:
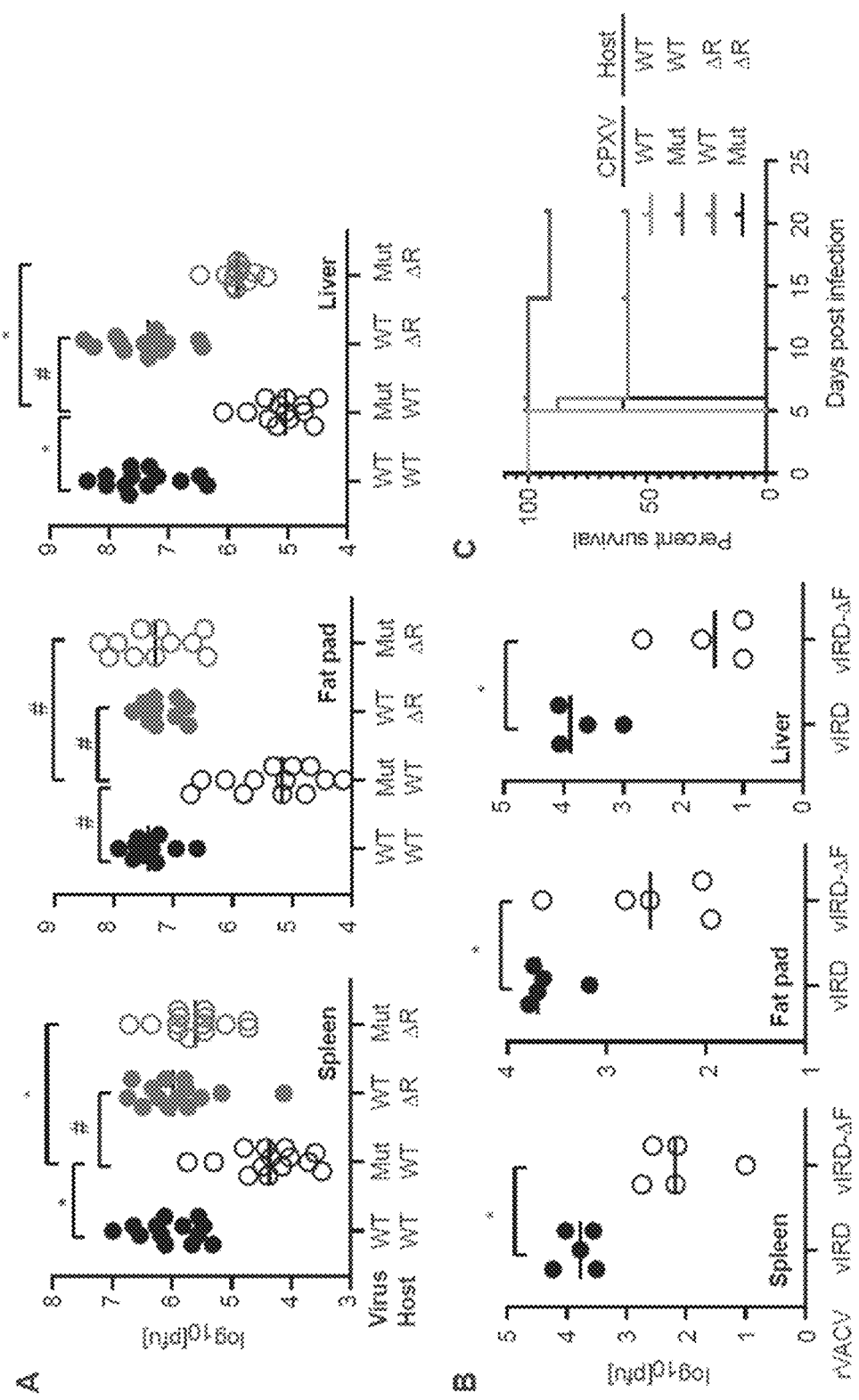
Figure 7:
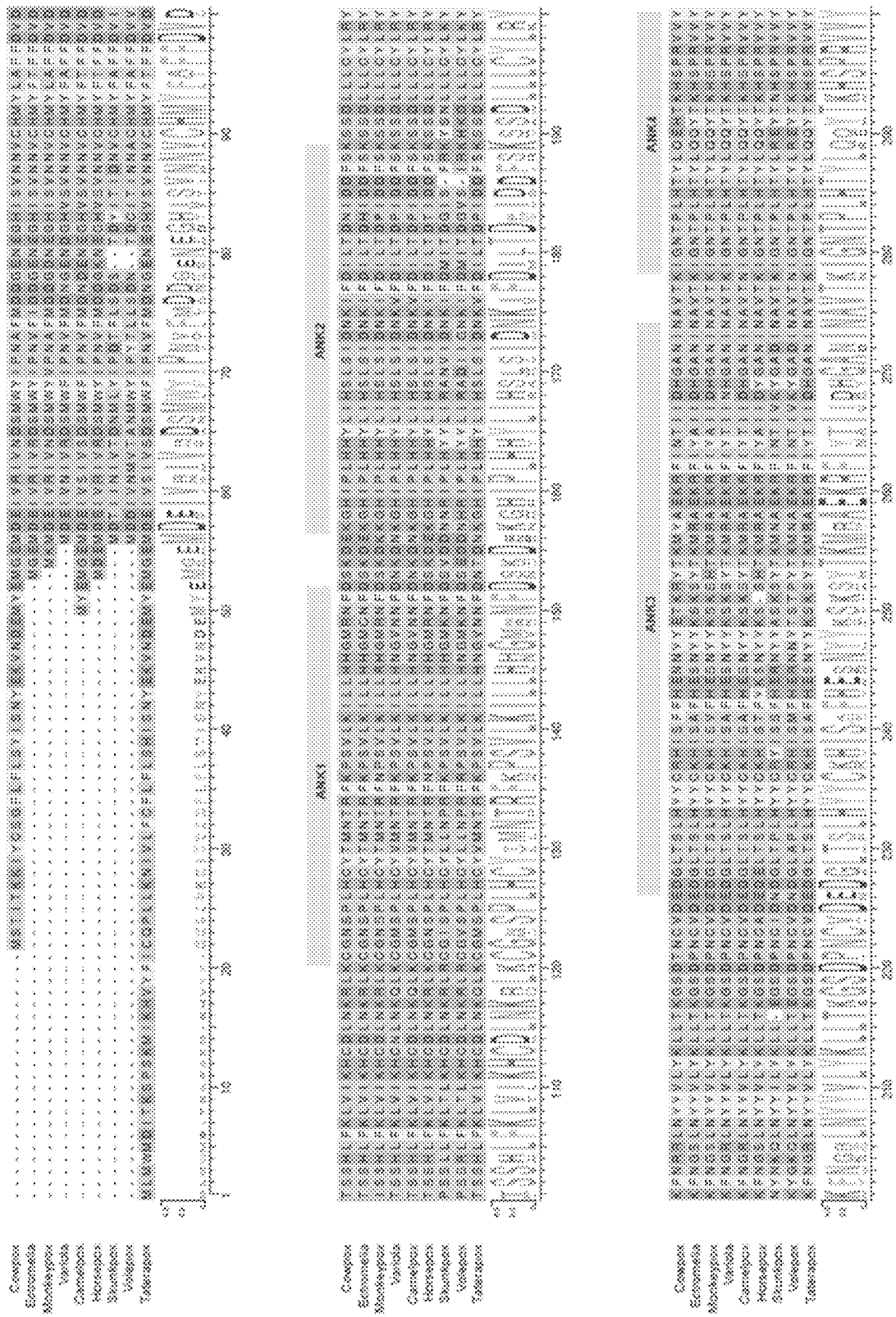
Figure 7:
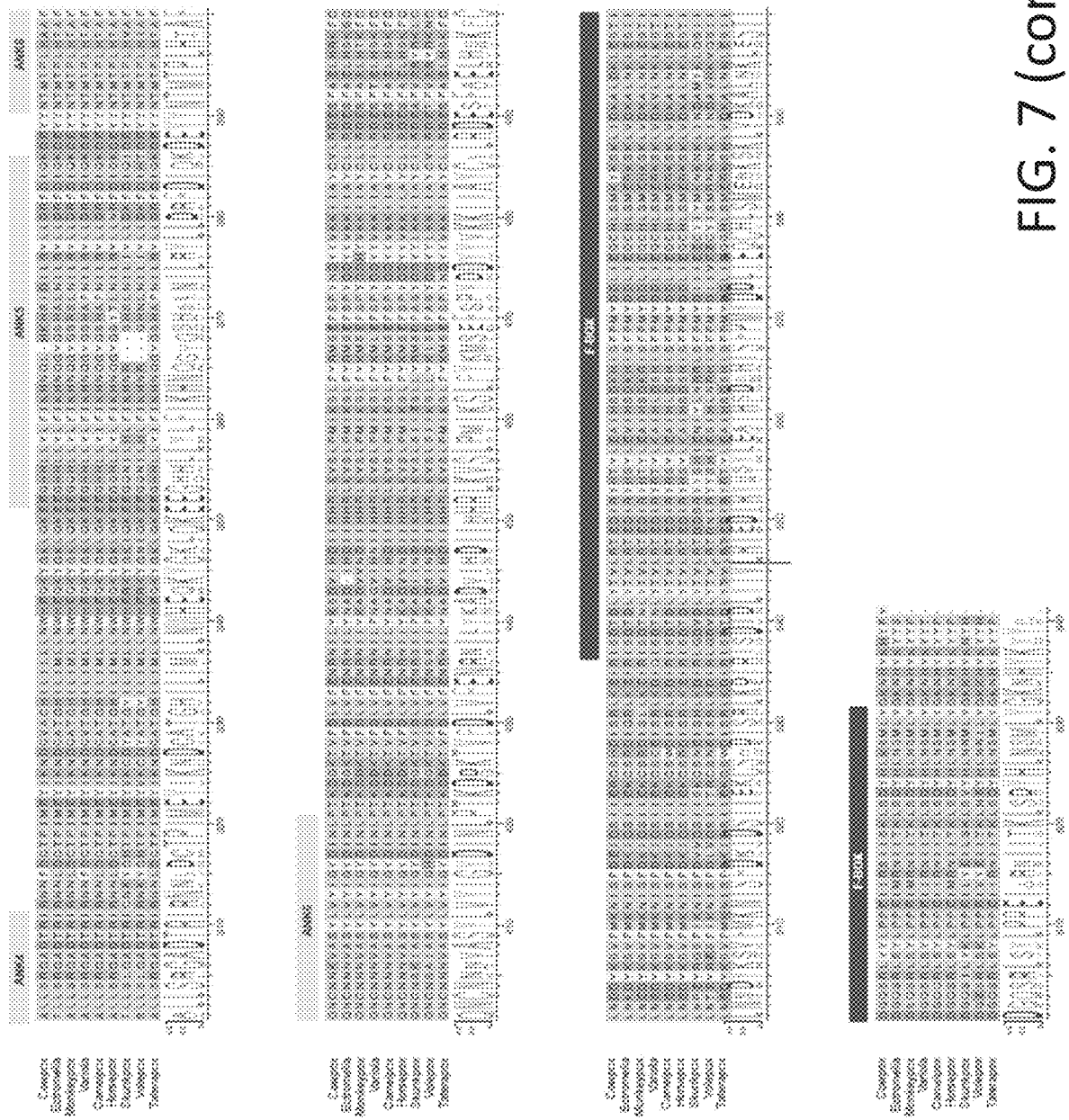

To distinguish whether RIPK3 degradation or IkBa are relevant vIRD cellular targets that controls viral replication in vivo, similar infections were performed in $Ripk3^{\Delta R/\Delta R}$ mice. $Ripk3^{\Delta R/\Delta R}$ mice express a truncated RIPK3 lacking the C-terminal RHIM and are functionally equivalent to $Ripk3^{-/-}$ mice (Moriwaki et al., 2017). Surprisingly, replication of CPXV-ΔvIRD was restored to normal level in $Ripk3^{\Delta R/\Delta R}$ mice in the spleen and fat pad (FIG. 5A). The rescue of CPXV-ΔvIRD replication in the liver of $Ripk3^{\Delta R/\Delta R}$ mice was significant but incomplete (FIG. 5A), suggesting that RIPK3-independent mechanisms may contribute to the control of viral replication in the liver. Re-expression of an intact vIRD, but not a F-box-deleted vIRD, enhanced VACV replication (FIG. 5B). Mice infected with wild type CPXV, but not CPXV-ΔvIRD, failed to clear the virus and eventually succumbed to the infection (FIGS. 5C and FIG. 12B). Consistently with a key role for RIPK3 targeting in viral pathogenesis, CPXV-ΔvIRD infection led to uncontrolled viral replication and lethal disease in $Ripk3^{\Delta R/\Delta R}$ mice (FIGS. 5C and FIG. 12B). Taken together, these results demonstrate that vIRD mainly targets RIPK3 to promote viral replication and pathogenesis in vivo.

Example 9

Figures 6A, 6B, 6C, 6D:
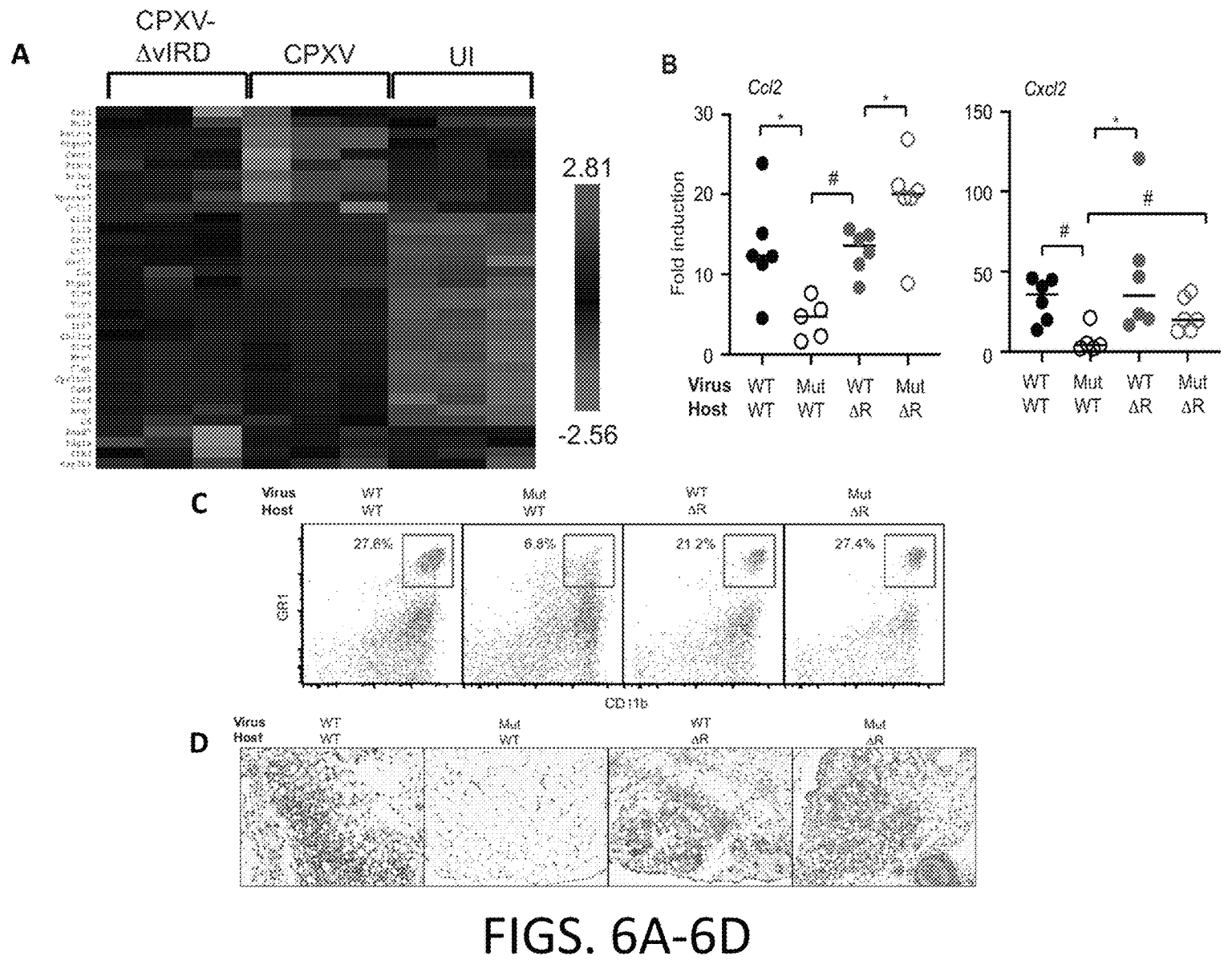

Inhibition of necroptosis does not suppress inflammation. Necroptosis is widely viewed as an inflammatory form of cell death. Thus, vIRD-mediated necroptosis inhibition would be expected to suppress innate inflammation. Surprisingly, Nanostring analysis of the visceral fat pad revealed distinct clusters of differentially expressed (DE) genes that were enhanced or inhibited by vIRD (FIG. 6A). Of the top DE genes identified, chemokines such as Ccl2 and Cxcl2 were differentially upregulated in wild type CPXV-infected mice but showed impaired induction in CPXV-ΔvIRD infected mice (FIGS. 6B and FIG. 13A). The reduced Cxcl2 expression correlated with a decrease in neutrophil infiltration in the fat pad of CPXV-ΔvIRD infected mice (FIG. 6C). Deletion of vIRD also dramatically reduced necrotic cell death and tissue damage in the visceral fat pad (FIG. 6D). Additionally, neutrophil infiltration and virus-induced tissue necrosis were restored in $Ripk3^{\Delta R/\Delta R}$ mice (FIGS. 6C-6D). These results indicate that RIPK3 is the main cellular target through which vIRD exerts its pathogenic effects.

7. SEQUENCES

Sequences relevant to the embodiments of the present disclosure are provided in the table below.

TABLE 1

Sequences.

| SEQ ID NO: | Name | Sequence |
|---|---|---|
| 1 | CPXV-vIRD (Cowpox) | MSTITKKIYCSGFLFLSYISNYEKVNDEMYEMGEMDEIVRIVNDSM WYIPNAFMDDGENEGHISVNNVCHMYLAFFDVDTSSHLFKLVIKHC DLNKRLKCGNSPLHCYTMNTRFKPSVLKILLHHGMRNFDSKDEKGH IPLHHYLIHSLSIDNKIFDILTDNIDDFSKSSDLLLCYLRYKFNRR LNYYVLYKLLTKGSDTNCVDEDGLTSLHYYCRHISFFHENNYYETK RYTKMYAEKRFINTIIDHGANINAVTKIGNTPLHTYLQEHTKHSPR VVYALLSRGADTRIRNNFDCTPIMEYIKNDCVACHILILLLNWHEQ KYGKLQKEEGHHLLYLFIKHNQLHKHSIDILRYLLDRFDIQKDEYY NTMTPLHAAFQNCNNKVASYLVYIGYDINLPTKDGKTVFDLVFENR NILYKSDVIHDIIRHRLKVSLPMIKSLFYRMSEFSPYNDYYVKKII AYCVLRDESFAELHRKFCLNDDYKSVFMKNISFDEIDSIIERCSHD |

TABLE 1-continued

Sequences.

| SEQ ID NO: | Name | Sequence |
|---|---|---|
| | | ISRLKEIRISDTDLYTVLRTEDIRYHTYLEAIHSDKHISFPMYDDL IEQCHLSMKYKSKLIDKALDKLESTIDGQSRLYYLPPEIIRSIISK LSDYHLKSMLYGKNHYKHYPY |
| 2 | CPXV-vIRD Δ6 | MSTITKKIYCSGFLFLSYISNYEKVNDEMYEMGEMDEIVRIVNDSM WYIPNAFMDDGENEGHISVNNVCHMYLAFFDVDTSSHLFKLVIKHC DLNKRLKCGNSPLHCYTMNTRFKPSVLKILLHHGMRNFDSKDEKGH IPLHHYLIHSLSIDNKIFDILTDNIDDFSKSSDLLLCYLRYKFNRR LNYYVLYKLLTKGSDTNCVDEDGLTSLHYYCRHISFFHENNYYETK RYTKMYAEKRFINTIIDHGANINAVTKIGNTPLHTYLQEHTKHSPR VVYALLSRGADTRIRNNFDCTPIMEYIKNDCVACHILILLLNWHEQ KYGKLQKEEGHHLLYLFIKHNQLHKHSIDILRYLLDRFDIQKDEYY PTKDGKTVFDLVFENRNILYKSDVIHDIIRHRLKVSLPMIKSLFYR MSEFSPYNDYYVKKIIAYCVLRDESFAELHRKFCLNDDYKSVFMKN ISFDEIDSIIERCSHDISRLKEIRISDTDLYTVLRTEDIRYHTYLE AIHSDKHISFPMYDDLIEQCHLSMKYKSKLIDKALDKLESTIDGQS RLYYLPPEIIRSIISKLSDYHLKSMLYGKNHYKHYPY |
| 3 | CPXV-vIRD Δ6+ Δ FBox | MSTITKKIYCSGFLFLSYISNYEKVNDEMYEMGEMDEIVRIVNDSM WYIPNAFMDDGENEGHISVNNVCHMYLAFFDVDTSSHLFKLVIKHC DLNKRLKCGNSPLHCYTMNTRFKPSVLKILLHHGMRNFDSKDEKGH IPLHHYLIHSLSIDNKIFDILTDNIDDFSKSSDLLLCYLRYKFNRR LNYYVLYKLLTKGSDTNCVDEDGLTSLHYYCRHISFFHENNYYETK RYTKMYAEKRFINTIIDHGANINAVTKIGNTPLHTYLQEHTKHSPR VVYALLSRGADTRIRNNFDCTPIMEYIKNDCVACHILILLLNWHEQ KYGKLQKEEGHHLLYLFIKHNQLHKHSIDILRYLLDRFDIQKDEYY PTKDGKTVFDLVFENRNILYKSDVIHDIIRHRLKVSLPMIKSLFYR MSEFSPYNDYYVKKIIAYCVLRDESFAELHRKFCLNDDYKSVFMKN ISFDEIDSIIERCSHDISRLKEIRKNHYKHYPY |
| 4 | CPXV-vIRD Δ FBox | MSTITKKIYCSGFLFLSYISNYEKVNDEMYEMGEMDEIVRIVNDSM WYIPNAFMDDGENEGHISVNNVCHMYLAFFDVDTSSHLFKLVIKHC DLNKRLKCGNSPLHCYTMNTRFKPSVLKILLHHGMRNFDSKDEKGH IPLHHYLIHSLSIDNKIFDILTDNIDDFSKSSDLLLCYLRYKFNRR LNYYVLYKLLTKGSDTNCVDEDGLTSLHYYCRHISFFHENNYYETK RYTKMYAEKRFINTIIDHGANINAVTKIGNTPLHTYLQEHTKHSPR VVYALLSRGADTRIRNNFDCTPIMEYIKNDCVACHILILLLNWHEQ KYGKLQKEEGHHLLYLFIKHNQLHKHSIDILRYLLDRFDIQKDEYY NTMTPLHAAFQNCNNKVASYLVYIGYDINLPTKDGKTVFDLVFENR NILYKSDVIHDIIRHRLKVSLPMIKSLFYRMSEFSPYNDYYVKKII AYCVLRDESFAELHRKFCLNDDYKSVFMKNISFDEIDSIIERCSHD ISRLKEIRGKNHYKHYPY |
| 5 | ECTV-vIRD (Ectromelia) | MGEMDEIVRIVRDSMWYIPNVFIDDGENEGHISVNNVCHMYFTFFD VDTSSHLFKLVIKHCDLNKRLKCGNSPLHCYTMNTRFKPSVLKIL HHGMCNFDSKDEKGHIPLHHYLIHSLSIDNKIFDILTDHIDDFSKS SDLLLCYLRYKFNGSLNYYVLYKLLTKGSDPNCVDEDGLTSLHYYC KHISAFHESNYYKSKSYTKMRAEKRFIYAIIDHGANINAVTKIGNT PLHTYLQQYTKHSPRVVYTLLSRGADTRIRNNLDCTPIMEYIKNDC ATGHILIMLLNWHEQKYGKLQKEEGHHLLYLFIKHNQGYGSHALNI LRYLLDRFDIQKDEYYNTMTPLHTAFQNCNNNVASYLVYIGYDINL PTKDGKTVFDLVFENRNILYNADIHDIIHHRLKVSLPMIKSLFYRM SEFSPYDDYYVKKIIAYCLLRDESFAELHSKSCLNKDYKSVFMKNI SFDKIDSIIEKCSRDIGRLKEIRISDTDLYTVLRTEDIRYHSYLEV IHSDKHISFPMYDDLIEQCHLSMERKSKLVDKALNKLESIIDGQSR LSYLPPEIMRNIITKLSDYHLNSMLYGKNHYKYYS |
| 6 | MPXV-vIRD (Monkeypox) | KLEKMDEIVRIVNDSMWYVPNAFMDDGDNEGHISVNNVCHMYLAFF DVDISSHLFKLVIKHCDLNKRLKCGNSPLHCYTMNTRFNPSVLKIL LRHGMRNFDSKDKKGHIPLHHYLIHSLSIDNKIFDILTDPIDDFSK SSDLLLCYLRYKFNGSLNYYVLYKLLTKGSDPNCVDEDGLTSLHYY CKHISVFHESNYYKSKSHTKMRAEKRFIYAIIDHGANINAVTKIGN TPLHTYLQQYTKHSPRVVYALLSRGADTRIRNNLDCTPIMEYIKND CATGHILIMLLNWHEQKYGKLQKEEGQHLLYLFIKHNQGYGSRSLN ILRYLLDRFDIQKDEYYNTMTPLHTAFQNCNNNVASYLVYIGYDIN LPTKDDKTVFDLVFENRNIIYKADVVNDIIHHRLKVSLPMIKSLFY KMSEFSPYDDHYVKKIIAYCLLRDESFAELHTKFCLNEDYKSVFMK NISFDKIDSIIEKCSRDISLLKEIRISDTNLYTVLRTEDIRYHTYL EAIHSDKRISFPMYDDLIEQCHLSMEHKSKLVDKALNKLESTIDSQ SRLSYLPPEIMRNIITKLSDYHLNSMLYGKNHYKYYPEFN |
| 7 | Variola-vIRD (Smallpox) | SLEDEIVNIVRDSMWFIPNVFMDNGENDGHVSVNNVCHMYFAFFDV DTSSHLFKLVIKHCNLNKQLKCGMSPLHCYVMNTRFKPSVLKILLH NGVNNFDNKDNKGHIPLHHYLIHSLSIDNKVFDILTDPIDDFSKSS DLLLCYLRYKFNGRLNYYVLYKLLTKGSDPNCVDEDGLTSLHYYCK |

TABLE 1-continued

Sequences.

| SEQ ID NO: | Name | Sequence |
|---|---|---|
| | | HISAFHESNYYKSKSYTKMRAEKRFIYTIINHGANINAVTKIGNTP LHTYLQQYTKHSPRVVYALLSRGADTRIRNNFDCTPIMEYIKNDCV TGHILIMLLNWHEQKYGKLQKEEGHHLLYLFIKHNQGYGSHAFNIL RYLLDRFDIQKDEYYNTMTPLHTAFQNCNNNVASYLVYIGYDINLP TKDDKTVFDLVFENRNILFNAGVIHNIIHHRLKVSLPMIKSLFYKM LEFSPYDDYYVKKIIAYCILRDESFTELHSKFCLNEDYKSVFMKNI SFDKIDSIIEKCSCEISRLKDIQISDTNLYTVLRTEDIRYRTYLKA IHLDSHISFPMYDDLIEQCHLSMERKSKLVDKVLNKLKSTIDGQSR LSYLPPEIIRNIITKLSDYHLNSMLYGKNHYKYYTEFR |
| 8 | Horsepox-vIRD | MDEMDEIVRIVRDSMWYIPNVFMDDGKNEGHVSVNNVCHMYFTFFD VDTSSHLFKLVIKHCDLNKRLKCGNSPLHCYTMNTRFNPSVLKILL HHGMRNFDSKDEKGHIPLHHYLIHSLSIDNKIFDILTDTIDDFSKS SDLLLCYLRYKFNGSLNYYVLYKLLTKGSDPNCADEDELTSLHYYC KHISTFYKSNYYKSSHTKMRAEKRFIYAIIDYGANINAVTKIGNTP LHTYLQQYTKHSPRVVYALLSRGADTRIRNNLDCTPIMEYIKNDCA TGHILIMLLNWHEQKYGKLQKEEGQHLLYLFIKHNQGYGSYTLNIL RYLLNRFDIQKDEYYNTMTPLHTAFQNCNNNVASYLVYIGYDINLP TKDDKTVFDLVFENRNIIYKADVVNDIIHHRLKVSLPMIKSLFYKM SEFSPYDDYYVKKILAYCLLRDESFAELHSKFCLNEDYKSVFMKNI SFDKIDSIIEKCSRDISRLKEIRISDTDLYTVLRTEDIRYHSYLKA IHSDSHISFPMYDDLIEQCHLSMERKSKLVDKALNKLESTIDGQSR LSYLPPEIMRNIITKLSDYHLNSMLYGKNHYKYYP |
| 9 | Skunk-pox-vIRD | MDTIINIVTDNMLYIPDTFLSDSTDYITIDNVCHMYFAFFDVIPSS LLFKLTLKHCDLNKRLRCGISPLHCYLLNPRFKPSVLKILLHHGMK NFDSVDDNNRIPLHYYLIRANVIDNKIFDMITDGISFRKYSNLLLC YLKYNYNKQLNYYILYKLLEGSDPNCIDNDGLTPLHYYCRYISSFH ERNYYASKSYTKMNAEKRFINTIVKYGADINAVTKIGNTPLHTYLR EYTNHSPRVVYTLLSLGADTRICNKYGHTPIMEYVKCDYATGYILI MLLNWHERKYGKIQKEEGQNILHLFIKHNRSHSLNILIYLLDKFDI QIDEYYNTMTPLHVAFQNCNSKIASYLVYIGYDINLPTKDGKTVID LVFENRSIIFKADIINDIIKHRLKVSLSIIESLLYRMSDFASYDDY YLKKIIAYCLRDEAFVERYRKLCLNPEYRGSFIKNISFDVVDSII SKCSNEISHLKDIRLGDVDLYTVLRTDDSRYYSHIENIYLNRRLSF PMYDIIIEECYIYMKNKNKLINDAMYKLQSIIDGQSILYKLPPEIL YEILSKLSVYHLNNMLYGKKHYKNYH |
| 10 | Tetrapox-vIRD | MLMWMDITKSPSKMIKHVYFICQPLLKNIVLFCFLFLSHISNYEKV NDEMYEMGEMDEIVSIVSDSMWFIPNVFMDNGENEGHVSVNNVCHM YFTFFDVDTSSHLFKLVIKHCDLNKQLKCGMSPLHCYVMNTRFKPS VLKILLHNGVNNFDNTDNKGHIPLHHYLIHSLSIDNKVFDILTDPI DDFSKSSDLLLCYLRYKFNGRLNYYVLYKLLTKGSDPNCVDEDGLT SLHYYCKHISAFHESNYYKSKSYTKMRAEKRFIYTIIDHGANINAV TKIGNTPLHTYLQQYTKHSPRVVYALLSRGADTRIRNNLDCTPIME YIKNDCATGHILIMLLNWHEQKYGKLQKEEGHHLLYIFIKHNQGYG SHAFNILRYLLDRFDIQKDEYYNTMTPLHTAFQNCNNNVASYLVYI GYDINLPTKDDKTVFDLVFENRNILYNADVIHDIIHHRLKVSLPMI KSLFYKMSEFSPYNDYYVKKIIAYCLLRDESFAELHSKFCLNEDYK SVFMKNISFDKIDSIIEKCSWDISRLKDIRISDTDLYTVLRTEDIR YRTYLEAIHSDSHISFPMYDDLIEQCHLSMERKSKLVDKALNKLES IIDGQSRLSYLPPEIIRNIITKLSDYHLNSMLYGKNHYKYYP |
| 11 | Camelpox-vIRD | MYEMGEMDEIVSIVSDSMWFIPNVFMDNDENEGHVSVNNVCHMYFT FFDVDTSSHLFKLVIKHCDLNKQLKCGMSPLHCYVMNTRFKPSVLK ILLHNGVNNFDNKDNKGHIPLHHYLIHSLSIDNKVFDILTDPIDDF SKSSDLLLCYLRYKFNGRLNYYVLYKLLTKGSDPNCVDEDGLTSLH YYCKHISAFHESNYYKSKSYTKMRAEKRFIYTIIDHGANINAVTNI GNTPLHTYLQQYTKHSPRVVYALLSRGADTRIRNNLDCTPIMEYIK NDCATGHILIMLLNWHEQKYGKLQKEEGHHLLYIFIKHNQGYGSHA FNILRYLLDRFDIQKDEYYNTMTPLHTAFQNCNNNVASYLVYIGYD INLPTKDDKTVFDLVFENRNILYNADVIHDIIHHRLKVSLPMIKSL FYKMSEFSPYDDYYVKKIIAYCILRDESFAELHSKFCLNEDYKSVF MKNISFDKIDSIIEKCSWDISRLKDIRISDTDLYTVLRTEDIRYRS YLEAIHLDSHISFPMYDDLIEQCHLSMERKSKLVDKALNKLESTID GQCRLSYLPPEIIRNIITKLSDYHLNSMLYGKNHYKYYP |
| 12 | Volepox-vIRD | MDDIVNMVTANMWYIPYTLLSDNTDCITINNACHMYFAFFDVVPSS RLFKLTLKHCDLNKRLRCGVSPLHCYLLNPRFRPSVLKILLHNGMK NFDSEDDNHRIPLHYYLIRADIIGNKIFDMITDGVSIRKHKDLLLC YLKYKYGKQLNYYVLYKLLTEGSDPNCVDNDGLAPLHYYCRHISMF HERNNYTSTPYTKMNAEKRFINTIVKYGADINAVTNIGNTPLHTYL REYTKHSPRVVYSLLSLGADTRIRNKYGHTPIMEYVKCDYATGYIL IMLLNWHERKYGNIQKEEGQNILHLFIKHNRGHNLNILIYLLDKFD IHTDEYYNTMTPLHIAFQNCNSAIASYLVYIGHDINLPTKDGKTVI |

TABLE 1-continued

Sequences.

| SEQ ID NO: | Name | Sequence |
|---|---|---|
| | | DLVFENSSIIFKADSINDIIKHRLKVSLSIIKSLLYKISDFASYDD YYLKKIIAYCVLRDETFVERYRKNCLNTEYRESFIKNISFDLVDSI ITRCSNEISRLKDIRLGDVDLYTVLRTDNIRYYSHIESIHLNRHIS FPMYDIIVEECYISMRNKNKLINDAVHKVQSIIDGESRLSKLPPEI VYEIITKLNEYHLNNILYGKKHYKYYH |

It is understood that the foregoing detailed description and accompanying examples are merely illustrative and are not to be taken as limitations upon the scope of the disclosure, which is defined solely by the appended claims and their equivalents.

All publications and patents mentioned in the above specification are herein incorporated by reference as if expressly set forth herein. Various changes and modifications to the disclosed embodiments will be apparent to those skilled in the art and may be made without departing from the spirit and scope thereof.

What is claimed is:

1. A recombinant polypeptide comprising a sequence having at least 95% sequence identity relative to the full-length sequence of SEQ ID NO: 3, wherein the polypeptide does not comprise an F-box motif.

2. The polypeptide of claim 1, wherein the polypeptide comprises at least 98% sequence identity relative to the full-length sequence of SEQ ID NO: 3.

3. A pharmaceutical composition comprising:
a recombinant polypeptide comprising a sequence having at least 95% sequence identity relative to the full-length sequence of SEQ ID NO: 3, wherein the polypeptide does not comprise an F-box motif; and
a pharmaceutically acceptable carrier or excipient.

4. The composition of claim 3, wherein the polypeptide comprises at least 98% sequence identity relative to the full-length sequence of SEQ ID NO: 3.

* * * * *

SEQUENCE LISTING

<160> NUMBER OF SEQ ID NOS: 23

<210> SEQ ID NO 1
<211> LENGTH: 619
<212> TYPE: PRT
<213> ORGANISM: Artificial sequence
<220> FEATURE:
<223> OTHER INFORMATION: synthetic

<400> SEQUENCE: 1

Met Ser Thr Ile Thr Lys Lys Ile Tyr Cys Ser Gly Phe Leu Phe Leu
1               5                   10                  15

Ser Tyr Ile Ser Asn Tyr Glu Lys Val Asn Asp Glu Met Tyr Glu Met
                20                  25                  30

Gly Glu Met Asp Glu Ile Val Arg Ile Val Asn Asp Ser Met Trp Tyr
            35                  40                  45

Ile Pro Asn Ala Phe Met Asp Asp Gly Glu Asn Glu Gly His Ile Ser
        50                  55                  60

Val Asn Asn Val Cys His Met Tyr Leu Ala Phe Phe Asp Val Asp Thr
65                  70                  75                  80

Ser Ser His Leu Phe Lys Leu Val Ile Lys His Cys Asp Leu Asn Lys
                85                  90                  95

Arg Leu Lys Cys Gly Asn Ser Pro Leu His Cys Tyr Thr Met Asn Thr
                100                 105                 110

Arg Phe Lys Pro Ser Val Leu Lys Ile Leu Leu His His Gly Met Arg
            115                 120                 125

Asn Phe Asp Ser Lys Asp Glu Lys Gly His Ile Pro Leu His His Tyr
        130                 135                 140

Leu Ile His Ser Leu Ser Ile Asp Asn Lys Ile Phe Asp Ile Leu Thr
145                 150                 155                 160

Asp Asn Ile Asp Asp Phe Ser Lys Ser Ser Asp Leu Leu Cys Tyr
                165                 170                 175

Leu Arg Tyr Lys Phe Asn Arg Arg Leu Asn Tyr Tyr Val Leu Tyr Lys
                180                 185                 190

Leu Leu Thr Lys Gly Ser Asp Thr Asn Cys Val Asp Glu Asp Gly Leu
            195                 200                 205

-continued

```
Thr Ser Leu His Tyr Tyr Cys Arg His Ile Ser Phe Phe His Glu Asn
    210                 215                 220
Asn Tyr Tyr Glu Thr Lys Arg Tyr Thr Lys Met Tyr Ala Glu Lys Arg
225                 230                 235                 240
Phe Ile Asn Thr Ile Ile Asp His Gly Ala Asn Ile Asn Ala Val Thr
                245                 250                 255
Lys Ile Gly Asn Thr Pro Leu His Thr Tyr Leu Gln Glu His Thr Lys
            260                 265                 270
His Ser Pro Arg Val Val Tyr Ala Leu Leu Ser Arg Gly Ala Asp Thr
        275                 280                 285
Arg Ile Arg Asn Asn Phe Asp Cys Thr Pro Ile Met Glu Tyr Ile Lys
    290                 295                 300
Asn Asp Cys Val Ala Cys His Ile Leu Ile Leu Leu Asn Trp His
305                 310                 315                 320
Glu Gln Lys Tyr Gly Lys Leu Gln Lys Glu Gly His His Leu Leu
                325                 330                 335
Tyr Leu Phe Ile Lys His Asn Gln Leu His Lys His Ser Ile Asp Ile
            340                 345                 350
Leu Arg Tyr Leu Leu Asp Arg Phe Asp Ile Gln Lys Asp Glu Tyr Tyr
        355                 360                 365
Asn Thr Met Thr Pro Leu His Ala Ala Phe Gln Asn Cys Asn Asn Lys
    370                 375                 380
Val Ala Ser Tyr Leu Val Tyr Ile Gly Tyr Asp Ile Asn Leu Pro Thr
385                 390                 395                 400
Lys Asp Gly Lys Thr Val Phe Asp Leu Val Phe Glu Asn Arg Asn Ile
                405                 410                 415
Leu Tyr Lys Ser Asp Val Ile His Asp Ile Ile Arg His Arg Leu Lys
            420                 425                 430
Val Ser Leu Pro Met Ile Lys Ser Leu Phe Tyr Arg Met Ser Glu Phe
        435                 440                 445
Ser Pro Tyr Asn Asp Tyr Tyr Val Lys Lys Ile Ile Ala Tyr Cys Val
    450                 455                 460
Leu Arg Asp Glu Ser Phe Ala Glu Leu His Arg Lys Phe Cys Leu Asn
465                 470                 475                 480
Asp Asp Tyr Lys Ser Val Phe Met Lys Asn Ile Ser Phe Asp Glu Ile
                485                 490                 495
Asp Ser Ile Ile Glu Arg Cys Ser His Asp Ile Ser Arg Leu Lys Glu
            500                 505                 510
Ile Arg Ile Ser Asp Thr Asp Leu Tyr Thr Val Leu Arg Thr Glu Asp
        515                 520                 525
Ile Arg Tyr His Thr Tyr Leu Glu Ala Ile His Ser Asp Lys His Ile
    530                 535                 540
Ser Phe Pro Met Tyr Asp Asp Leu Ile Glu Gln Cys His Leu Ser Met
545                 550                 555                 560
Lys Tyr Lys Ser Lys Leu Ile Asp Lys Ala Leu Asp Lys Leu Glu Ser
                565                 570                 575
Thr Ile Asp Gly Gln Ser Arg Leu Tyr Tyr Leu Pro Pro Glu Ile Ile
            580                 585                 590
Arg Ser Ile Ile Ser Lys Leu Ser Asp Tyr His Leu Lys Ser Met Leu
        595                 600                 605
Tyr Gly Lys Asn His Tyr Lys His Tyr Pro Tyr
    610                 615
```

<210> SEQ ID NO 2
<211> LENGTH: 589
<212> TYPE: PRT
<213> ORGANISM: Artificial sequence
<220> FEATURE:
<223> OTHER INFORMATION: synthetic

<400> SEQUENCE: 2

```
Met Ser Thr Ile Thr Lys Lys Ile Tyr Cys Ser Gly Phe Leu Phe Leu
1               5                   10                  15

Ser Tyr Ile Ser Asn Tyr Glu Lys Val Asn Asp Glu Met Tyr Glu Met
            20                  25                  30

Gly Glu Met Asp Glu Ile Val Arg Ile Val Asn Asp Ser Met Trp Tyr
        35                  40                  45

Ile Pro Asn Ala Phe Met Asp Asp Gly Glu Asn Glu Gly His Ile Ser
    50                  55                  60

Val Asn Asn Val Cys His Met Tyr Leu Ala Phe Phe Asp Val Asp Thr
65                  70                  75                  80

Ser Ser His Leu Phe Lys Leu Val Ile Lys His Cys Asp Leu Asn Lys
                85                  90                  95

Arg Leu Lys Cys Gly Asn Ser Pro Leu His Cys Tyr Thr Met Asn Thr
            100                 105                 110

Arg Phe Lys Pro Ser Val Leu Lys Ile Leu Leu His His Gly Met Arg
        115                 120                 125

Asn Phe Asp Ser Lys Asp Glu Lys Gly His Ile Pro Leu His His Tyr
    130                 135                 140

Leu Ile His Ser Leu Ser Ile Asp Asn Lys Ile Phe Asp Ile Leu Thr
145                 150                 155                 160

Asp Asn Ile Asp Asp Phe Ser Lys Ser Ser Asp Leu Leu Cys Tyr
                165                 170                 175

Leu Arg Tyr Lys Phe Asn Arg Arg Leu Asn Tyr Tyr Val Leu Tyr Lys
            180                 185                 190

Leu Leu Thr Lys Gly Ser Asp Thr Asn Cys Val Asp Glu Asp Gly Leu
        195                 200                 205

Thr Ser Leu His Tyr Tyr Cys Arg His Ile Ser Phe Phe His Glu Asn
    210                 215                 220

Asn Tyr Tyr Glu Thr Lys Arg Tyr Thr Lys Met Tyr Ala Glu Lys Arg
225                 230                 235                 240

Phe Ile Asn Thr Ile Ile Asp His Gly Ala Asn Ile Asn Ala Val Thr
                245                 250                 255

Lys Ile Gly Asn Thr Pro Leu His Thr Tyr Leu Gln Glu His Thr Lys
            260                 265                 270

His Ser Pro Arg Val Val Tyr Ala Leu Leu Ser Arg Gly Ala Asp Thr
        275                 280                 285

Arg Ile Arg Asn Asn Phe Asp Cys Thr Pro Ile Met Glu Tyr Ile Lys
    290                 295                 300

Asn Asp Cys Val Ala Cys His Ile Leu Ile Leu Leu Asn Trp His
305                 310                 315                 320

Glu Gln Lys Tyr Gly Lys Leu Gln Lys Glu Gly His His Leu Leu
                325                 330                 335

Tyr Leu Phe Ile Lys His Asn Gln Leu His Lys His Ser Ile Asp Ile
            340                 345                 350

Leu Arg Tyr Leu Leu Asp Arg Phe Asp Ile Gln Lys Asp Glu Tyr Tyr
        355                 360                 365
```

Pro Thr Lys Asp Gly Lys Thr Val Phe Asp Leu Val Phe Glu Asn Arg
370             375                 380

Asn Ile Leu Tyr Lys Ser Asp Val Ile His Asp Ile Ile Arg His Arg
385                 390                 395                 400

Leu Lys Val Ser Leu Pro Met Ile Lys Ser Leu Phe Tyr Arg Met Ser
            405                 410                 415

Glu Phe Ser Pro Tyr Asn Asp Tyr Val Lys Ile Ile Ala Tyr
        420                 425                 430

Cys Val Leu Arg Asp Glu Ser Phe Ala Glu Leu His Arg Lys Phe Cys
            435                 440                 445

Leu Asn Asp Asp Tyr Lys Ser Val Phe Met Lys Asn Ile Ser Phe Asp
450                 455                 460

Glu Ile Asp Ser Ile Ile Glu Arg Cys Ser His Asp Ile Ser Arg Leu
465                 470                 475                 480

Lys Glu Ile Arg Ile Ser Asp Thr Asp Leu Tyr Thr Val Leu Arg Thr
                485                 490                 495

Glu Asp Ile Arg Tyr His Thr Tyr Leu Glu Ala Ile His Ser Asp Lys
            500                 505                 510

His Ile Ser Phe Pro Met Tyr Asp Asp Leu Ile Glu Gln Cys His Leu
        515                 520                 525

Ser Met Lys Tyr Lys Ser Lys Leu Ile Asp Lys Ala Leu Asp Lys Leu
530                 535                 540

Glu Ser Thr Ile Asp Gly Gln Ser Arg Leu Tyr Tyr Leu Pro Pro Glu
545                 550                 555                 560

Ile Ile Arg Ser Ile Ile Ser Lys Leu Ser Asp Tyr His Leu Lys Ser
                565                 570                 575

Met Leu Tyr Gly Lys Asn His Tyr Lys His Tyr Pro Tyr
            580                 585

<210> SEQ ID NO 3
<211> LENGTH: 493
<212> TYPE: PRT
<213> ORGANISM: Artificial sequence
<220> FEATURE:
<223> OTHER INFORMATION: synthetic

<400> SEQUENCE: 3

Met Ser Thr Ile Thr Lys Lys Ile Tyr Cys Ser Gly Phe Leu Phe Leu
1               5                   10                  15

Ser Tyr Ile Ser Asn Tyr Glu Lys Val Asn Asp Glu Met Tyr Glu Met
            20                  25                  30

Gly Glu Met Asp Glu Ile Val Arg Ile Val Asn Asp Ser Met Trp Tyr
        35                  40                  45

Ile Pro Asn Ala Phe Met Asp Asp Gly Glu Asn Glu Gly His Ile Ser
50                  55                  60

Val Asn Asn Val Cys His Met Tyr Leu Ala Phe Phe Asp Val Asp Thr
65                  70                  75                  80

Ser Ser His Leu Phe Lys Leu Val Ile Lys His Cys Asp Leu Asn Lys
                85                  90                  95

Arg Leu Lys Cys Gly Asn Ser Pro Leu His Cys Tyr Thr Met Asn Thr
            100                 105                 110

Arg Phe Lys Pro Ser Val Leu Lys Ile Leu Leu His Gly Met Arg
        115                 120                 125

Asn Phe Asp Ser Lys Asp Glu Lys Gly His Ile Pro Leu His His Tyr
130                 135                 140

```
Leu Ile His Ser Leu Ser Ile Asp Asn Lys Ile Phe Asp Ile Leu Thr
145                 150                 155                 160

Asp Asn Ile Asp Asp Phe Ser Lys Ser Ser Asp Leu Leu Leu Cys Tyr
                165                 170                 175

Leu Arg Tyr Lys Phe Asn Arg Arg Leu Asn Tyr Tyr Val Leu Tyr Lys
            180                 185                 190

Leu Leu Thr Lys Gly Ser Asp Thr Asn Cys Val Asp Glu Asp Gly Leu
        195                 200                 205

Thr Ser Leu His Tyr Tyr Cys Arg His Ile Ser Phe Phe His Glu Asn
    210                 215                 220

Asn Tyr Tyr Glu Thr Lys Arg Tyr Thr Lys Met Tyr Ala Glu Lys Arg
225                 230                 235                 240

Phe Ile Asn Thr Ile Ile Asp His Gly Ala Asn Ile Asn Ala Val Thr
                245                 250                 255

Lys Ile Gly Asn Thr Pro Leu His Thr Tyr Leu Gln Glu His Thr Lys
                260                 265                 270

His Ser Pro Arg Val Val Tyr Ala Leu Leu Ser Arg Gly Ala Asp Thr
            275                 280                 285

Arg Ile Arg Asn Asn Phe Asp Cys Thr Pro Ile Met Glu Tyr Ile Lys
290                 295                 300

Asn Asp Cys Val Ala Cys His Ile Leu Ile Leu Leu Asn Trp His
305                 310                 315                 320

Glu Gln Lys Tyr Gly Lys Leu Gln Lys Glu Gly His His Leu Leu
                325                 330                 335

Tyr Leu Phe Ile Lys His Asn Gln Leu His Lys His Ser Ile Asp Ile
            340                 345                 350

Leu Arg Tyr Leu Leu Asp Arg Phe Asp Ile Gln Lys Asp Glu Tyr Tyr
        355                 360                 365

Pro Thr Lys Asp Gly Lys Thr Val Phe Asp Leu Val Phe Glu Asn Arg
    370                 375                 380

Asn Ile Leu Tyr Lys Ser Asp Val Ile His Asp Ile Ile Arg His Arg
385                 390                 395                 400

Leu Lys Val Ser Leu Pro Met Ile Lys Ser Leu Phe Tyr Arg Met Ser
                405                 410                 415

Glu Phe Ser Pro Tyr Asn Asp Tyr Tyr Val Lys Lys Ile Ile Ala Tyr
            420                 425                 430

Cys Val Leu Arg Asp Glu Ser Phe Ala Glu Leu His Arg Lys Phe Cys
        435                 440                 445

Leu Asn Asp Asp Tyr Lys Ser Val Phe Met Lys Asn Ile Ser Phe Asp
    450                 455                 460

Glu Ile Asp Ser Ile Ile Glu Arg Cys Ser His Asp Ile Ser Arg Leu
465                 470                 475                 480

Lys Glu Ile Arg Lys Asn His Tyr Lys His Tyr Pro Tyr
                485                 490

<210> SEQ ID NO 4
<211> LENGTH: 524
<212> TYPE: PRT
<213> ORGANISM: Artificial sequence
<220> FEATURE:
<223> OTHER INFORMATION: synthetic

<400> SEQUENCE: 4

Met Ser Thr Ile Thr Lys Lys Ile Tyr Cys Ser Gly Phe Leu Phe Leu
1               5                   10                  15
```

```
Ser Tyr Ile Ser Asn Tyr Glu Lys Val Asn Asp Glu Met Tyr Glu Met
            20                  25                  30

Gly Glu Met Asp Glu Ile Val Arg Ile Val Asn Asp Ser Met Trp Tyr
        35                  40                  45

Ile Pro Asn Ala Phe Met Asp Asp Gly Glu Asn Glu Gly His Ile Ser
    50                  55                  60

Val Asn Asn Val Cys His Met Tyr Leu Ala Phe Phe Asp Val Asp Thr
65                  70                  75                  80

Ser Ser His Leu Phe Lys Leu Val Ile Lys His Cys Asp Leu Asn Lys
                85                  90                  95

Arg Leu Lys Cys Gly Asn Ser Pro Leu His Cys Tyr Thr Met Asn Thr
            100                 105                 110

Arg Phe Lys Pro Ser Val Leu Lys Ile Leu Leu His His Gly Met Arg
        115                 120                 125

Asn Phe Asp Ser Lys Asp Glu Lys Gly His Ile Pro Leu His His Tyr
    130                 135                 140

Leu Ile His Ser Leu Ser Ile Asp Asn Lys Ile Phe Asp Ile Leu Thr
145                 150                 155                 160

Asp Asn Ile Asp Asp Phe Ser Lys Ser Ser Asp Leu Leu Leu Cys Tyr
                165                 170                 175

Leu Arg Tyr Lys Phe Asn Arg Arg Leu Asn Tyr Tyr Val Leu Tyr Lys
            180                 185                 190

Leu Leu Thr Lys Gly Ser Asp Thr Asn Cys Val Asp Glu Asp Gly Leu
        195                 200                 205

Thr Ser Leu His Tyr Tyr Cys Arg His Ile Ser Phe Phe His Glu Asn
    210                 215                 220

Asn Tyr Tyr Glu Thr Lys Arg Tyr Thr Lys Met Tyr Ala Glu Lys Arg
225                 230                 235                 240

Phe Ile Asn Thr Ile Ile Asp His Gly Ala Asn Ile Asn Ala Val Thr
                245                 250                 255

Lys Ile Gly Asn Thr Pro Leu His Thr Tyr Leu Gln Glu His Thr Lys
            260                 265                 270

His Ser Pro Arg Val Val Tyr Ala Leu Leu Ser Arg Gly Ala Asp Thr
        275                 280                 285

Arg Ile Arg Asn Asn Phe Asp Cys Thr Pro Ile Met Glu Tyr Ile Lys
    290                 295                 300

Asn Asp Cys Val Ala Cys His Ile Leu Ile Leu Leu Leu Asn Trp His
305                 310                 315                 320

Glu Gln Lys Tyr Gly Lys Leu Gln Lys Glu Glu Gly His His Leu Leu
                325                 330                 335

Tyr Leu Phe Ile Lys His Asn Gln Leu His Lys His Ser Ile Asp Ile
            340                 345                 350

Leu Arg Tyr Leu Leu Asp Arg Phe Asp Ile Gln Lys Asp Glu Tyr Tyr
        355                 360                 365

Asn Thr Met Thr Pro Leu His Ala Ala Phe Gln Asn Cys Asn Asn Lys
    370                 375                 380

Val Ala Ser Tyr Leu Val Tyr Ile Gly Tyr Asp Ile Asn Leu Pro Thr
385                 390                 395                 400

Lys Asp Gly Lys Thr Val Phe Asp Leu Val Phe Glu Asn Arg Asn Ile
                405                 410                 415

Leu Tyr Lys Ser Asp Val Ile His Asp Ile Ile Arg His Arg Leu Lys
            420                 425                 430

Val Ser Leu Pro Met Ile Lys Ser Leu Phe Tyr Arg Met Ser Glu Phe
```

```
                435                 440                 445
Ser Pro Tyr Asn Asp Tyr Tyr Val Lys Lys Ile Ile Ala Tyr Cys Val
450                 455                 460
Leu Arg Asp Glu Ser Phe Ala Glu Leu His Arg Lys Phe Cys Leu Asn
465                 470                 475                 480
Asp Asp Tyr Lys Ser Val Phe Met Lys Asn Ile Ser Phe Asp Glu Ile
                485                 490                 495
Asp Ser Ile Ile Glu Arg Cys Ser His Asp Ile Ser Arg Leu Lys Glu
            500                 505                 510
Ile Arg Gly Lys Asn His Tyr Lys His Tyr Pro Tyr
        515                 520

<210> SEQ ID NO 5
<211> LENGTH: 587
<212> TYPE: PRT
<213> ORGANISM: Artificial sequence
<220> FEATURE:
<223> OTHER INFORMATION: synthetic

<400> SEQUENCE: 5

Met Gly Glu Met Asp Glu Ile Val Arg Ile Val Arg Asp Ser Met Trp
1               5                   10                  15
Tyr Ile Pro Asn Val Phe Ile Asp Asp Gly Glu Asn Glu Gly His Ile
            20                  25                  30
Ser Val Asn Asn Val Cys His Met Tyr Phe Thr Phe Asp Val Asp
        35                  40                  45
Thr Ser Ser His Leu Phe Lys Leu Val Ile Lys His Cys Asp Leu Asn
50                  55                  60
Lys Arg Leu Lys Cys Gly Asn Ser Pro Leu His Cys Tyr Thr Met Asn
65                  70                  75                  80
Thr Arg Phe Lys Pro Ser Val Leu Lys Ile Leu Leu His His Gly Met
                85                  90                  95
Cys Asn Phe Asp Ser Lys Asp Glu Lys Gly His Ile Pro Leu His His
            100                 105                 110
Tyr Leu Ile His Ser Leu Ser Ile Asp Asn Lys Ile Phe Asp Ile Leu
        115                 120                 125
Thr Asp His Ile Asp Asp Phe Ser Lys Ser Ser Asp Leu Leu Leu Cys
130                 135                 140
Tyr Leu Arg Tyr Lys Phe Asn Gly Ser Leu Asn Tyr Tyr Val Leu Tyr
145                 150                 155                 160
Lys Leu Leu Thr Lys Gly Ser Asp Pro Asn Cys Val Asp Glu Asp Gly
                165                 170                 175
Leu Thr Ser Leu His Tyr Tyr Cys Lys His Ile Ser Ala Phe His Glu
            180                 185                 190
Ser Asn Tyr Tyr Lys Ser Lys Ser Tyr Thr Lys Met Arg Ala Glu Lys
        195                 200                 205
Arg Phe Ile Tyr Ala Ile Ile Asp His Gly Ala Asn Ile Asn Ala Val
210                 215                 220
Thr Lys Ile Gly Asn Thr Pro Leu His Thr Tyr Leu Gln Gln Tyr Thr
225                 230                 235                 240
Lys His Ser Pro Arg Val Val Tyr Thr Leu Leu Ser Arg Gly Ala Asp
                245                 250                 255
Thr Arg Ile Arg Asn Asn Leu Asp Cys Thr Pro Ile Met Glu Tyr Ile
            260                 265                 270
Lys Asn Asp Cys Ala Thr Gly His Ile Leu Ile Met Leu Leu Asn Trp
```

```
                275                 280                 285
His Glu Gln Lys Tyr Gly Lys Leu Gln Lys Glu Glu Gly His His Leu
            290                 295                 300
Leu Tyr Leu Phe Ile Lys His Asn Gln Gly Tyr Gly Ser His Ala Leu
305                 310                 315                 320
Asn Ile Leu Arg Tyr Leu Leu Asp Arg Phe Asp Ile Gln Lys Asp Glu
                325                 330                 335
Tyr Tyr Asn Thr Met Thr Pro Leu His Thr Ala Phe Gln Asn Cys Asn
            340                 345                 350
Asn Asn Val Ala Ser Tyr Leu Val Tyr Ile Gly Tyr Asp Ile Asn Leu
        355                 360                 365
Pro Thr Lys Asp Gly Lys Thr Val Phe Asp Leu Val Phe Glu Asn Arg
370                 375                 380
Asn Ile Leu Tyr Asn Ala Asp Ile His Asp Ile His His Arg Leu
385                 390                 395                 400
Lys Val Ser Leu Pro Met Ile Lys Ser Leu Phe Tyr Arg Met Ser Glu
                405                 410                 415
Phe Ser Pro Tyr Asp Asp Tyr Val Lys Lys Ile Ala Tyr Cys
            420                 425                 430
Leu Leu Arg Asp Glu Ser Phe Ala Glu Leu His Ser Lys Ser Cys Leu
        435                 440                 445
Asn Lys Asp Tyr Lys Ser Val Phe Met Lys Asn Ile Ser Phe Asp Lys
450                 455                 460
Ile Asp Ser Ile Ile Glu Lys Cys Ser Arg Asp Ile Gly Arg Leu Lys
465                 470                 475                 480
Glu Ile Arg Ile Ser Asp Thr Asp Leu Tyr Thr Val Leu Arg Thr Glu
                485                 490                 495
Asp Ile Arg Tyr His Ser Tyr Leu Glu Val Ile His Ser Asp Lys His
            500                 505                 510
Ile Ser Phe Pro Met Tyr Asp Asp Leu Ile Glu Gln Cys His Leu Ser
        515                 520                 525
Met Glu Arg Lys Ser Lys Leu Val Asp Lys Ala Leu Asn Lys Leu Glu
530                 535                 540
Ser Ile Ile Asp Gly Gln Ser Arg Leu Ser Tyr Leu Pro Pro Glu Ile
545                 550                 555                 560
Met Arg Asn Ile Ile Thr Lys Leu Ser Asp Tyr His Leu Asn Ser Met
                565                 570                 575
Leu Tyr Gly Lys Asn His Tyr Lys Tyr Tyr Ser
            580                 585

<210> SEQ ID NO 6
<211> LENGTH: 592
<212> TYPE: PRT
<213> ORGANISM: Artificial sequence
<220> FEATURE:
<223> OTHER INFORMATION: synthetic

<400> SEQUENCE: 6

Lys Leu Glu Lys Met Asp Glu Ile Val Arg Ile Val Asn Asp Ser Met
1               5                   10                  15
Trp Tyr Val Pro Asn Ala Phe Met Asp Asp Gly Asp Asn Glu Gly His
            20                  25                  30
Ile Ser Val Asn Asn Val Cys His Met Tyr Leu Ala Phe Phe Asp Val
        35                  40                  45
Asp Ile Ser Ser His Leu Phe Lys Leu Val Ile Lys His Cys Asp Leu
```

```
            50                  55                  60
Asn Lys Arg Leu Lys Cys Gly Asn Ser Pro Leu His Cys Tyr Thr Met
 65                  70                  75                  80

Asn Thr Arg Phe Asn Pro Ser Val Leu Lys Ile Leu Leu Arg His Gly
                 85                  90                  95

Met Arg Asn Phe Asp Ser Lys Asp Lys Gly His Ile Pro Leu His
                100                 105                 110

His Tyr Leu Ile His Ser Leu Ser Ile Asp Asn Lys Ile Phe Asp Ile
            115                 120                 125

Leu Thr Asp Pro Ile Asp Asp Phe Ser Lys Ser Ser Asp Leu Leu Leu
        130                 135                 140

Cys Tyr Leu Arg Tyr Lys Phe Asn Gly Ser Leu Asn Tyr Tyr Val Leu
145                 150                 155                 160

Tyr Lys Leu Leu Thr Lys Gly Ser Asp Pro Asn Cys Val Asp Glu Asp
                165                 170                 175

Gly Leu Thr Ser Leu His Tyr Tyr Cys Lys His Ile Ser Val Phe His
            180                 185                 190

Glu Ser Asn Tyr Tyr Lys Ser Lys Ser His Thr Lys Met Arg Ala Glu
        195                 200                 205

Lys Arg Phe Ile Tyr Ala Ile Ile Asp His Gly Ala Asn Ile Asn Ala
210                 215                 220

Val Thr Lys Ile Gly Asn Thr Pro Leu His Thr Tyr Leu Gln Gln Tyr
225                 230                 235                 240

Thr Lys His Ser Pro Arg Val Val Tyr Ala Leu Leu Ser Arg Gly Ala
                245                 250                 255

Asp Thr Arg Ile Arg Asn Asn Leu Asp Cys Thr Pro Ile Met Glu Tyr
            260                 265                 270

Ile Lys Asn Asp Cys Ala Thr Gly His Ile Leu Ile Met Leu Leu Asn
        275                 280                 285

Trp His Glu Gln Lys Tyr Gly Lys Leu Gln Lys Glu Glu Gly Gln His
290                 295                 300

Leu Leu Tyr Leu Phe Ile Lys His Asn Gln Gly Tyr Gly Ser Arg Ser
305                 310                 315                 320

Leu Asn Ile Leu Arg Tyr Leu Leu Asp Arg Phe Asp Ile Gln Lys Asp
                325                 330                 335

Glu Tyr Tyr Asn Thr Met Thr Pro Leu His Thr Ala Phe Gln Asn Cys
            340                 345                 350

Asn Asn Asn Val Ala Ser Tyr Leu Val Tyr Ile Gly Tyr Asp Ile Asn
        355                 360                 365

Leu Pro Thr Lys Asp Asp Lys Thr Val Phe Asp Leu Val Phe Glu Asn
370                 375                 380

Arg Asn Ile Ile Tyr Lys Ala Asp Val Val Asn Asp Ile Ile His His
385                 390                 395                 400

Arg Leu Lys Val Ser Leu Pro Met Ile Lys Ser Leu Phe Tyr Lys Met
                405                 410                 415

Ser Glu Phe Ser Pro Tyr Asp Asp His Tyr Val Lys Lys Ile Ile Ala
            420                 425                 430

Tyr Cys Leu Leu Arg Asp Glu Ser Phe Ala Glu Leu His Thr Lys Phe
        435                 440                 445

Cys Leu Asn Glu Asp Tyr Lys Ser Val Phe Met Lys Asn Ile Ser Phe
450                 455                 460

Asp Lys Ile Asp Ser Ile Ile Glu Lys Cys Ser Arg Asp Ile Ser Leu
465                 470                 475                 480
```

```
Leu Lys Glu Ile Arg Ile Ser Asp Thr Asn Leu Tyr Thr Val Leu Arg
                485                 490                 495

Thr Glu Asp Ile Arg Tyr His Thr Tyr Leu Glu Ala Ile His Ser Asp
            500                 505                 510

Lys Arg Ile Ser Phe Pro Met Tyr Asp Asp Leu Ile Glu Gln Cys His
        515                 520                 525

Leu Ser Met Glu His Lys Ser Lys Leu Val Asp Lys Ala Leu Asn Lys
    530                 535                 540

Leu Glu Ser Thr Ile Asp Ser Gln Ser Arg Leu Ser Tyr Leu Pro Pro
545                 550                 555                 560

Glu Ile Met Arg Asn Ile Ile Thr Lys Leu Ser Asp Tyr His Leu Asn
                565                 570                 575

Ser Met Leu Tyr Gly Lys Asn His Tyr Lys Tyr Tyr Pro Glu Phe Asn
                580                 585                 590
```

<210> SEQ ID NO 7
<211> LENGTH: 590
<212> TYPE: PRT
<213> ORGANISM: Artificial sequence
<220> FEATURE:
<223> OTHER INFORMATION: synthetic

<400> SEQUENCE: 7

```
Ser Leu Glu Asp Glu Ile Val Asn Ile Val Arg Asp Ser Met Trp Phe
1               5                   10                  15

Ile Pro Asn Val Phe Met Asp Asn Gly Glu Asn Asp Gly His Val Ser
                20                  25                  30

Val Asn Asn Val Cys His Met Tyr Phe Ala Phe Phe Asp Val Asp Thr
            35                  40                  45

Ser Ser His Leu Phe Lys Leu Val Ile Lys His Cys Asn Leu Asn Lys
        50                  55                  60

Gln Leu Lys Cys Gly Met Ser Pro Leu His Cys Tyr Val Met Asn Thr
65                  70                  75                  80

Arg Phe Lys Pro Ser Val Leu Lys Ile Leu Leu His Asn Gly Val Asn
                85                  90                  95

Asn Phe Asp Asn Lys Asp Asn Lys Gly His Ile Pro Leu His His Tyr
                100                 105                 110

Leu Ile His Ser Leu Ser Ile Asp Asn Lys Val Phe Asp Ile Leu Thr
            115                 120                 125

Asp Pro Ile Asp Asp Phe Ser Lys Ser Ser Asp Leu Leu Leu Cys Tyr
        130                 135                 140

Leu Arg Tyr Lys Phe Asn Gly Arg Leu Asn Tyr Tyr Val Leu Tyr Lys
145                 150                 155                 160

Leu Leu Thr Lys Gly Ser Asp Pro Asn Cys Val Asp Glu Asp Gly Leu
                165                 170                 175

Thr Ser Leu His Tyr Tyr Cys Lys His Ile Ser Ala Phe His Glu Ser
                180                 185                 190

Asn Tyr Tyr Lys Ser Lys Ser Tyr Thr Lys Met Arg Ala Glu Lys Arg
            195                 200                 205

Phe Ile Tyr Thr Ile Ile Asn His Gly Ala Asn Ile Asn Ala Val Thr
        210                 215                 220

Lys Ile Gly Asn Thr Pro Leu His Thr Tyr Leu Gln Gln Tyr Thr Lys
225                 230                 235                 240

His Ser Pro Arg Val Val Tyr Ala Leu Leu Ser Arg Gly Ala Asp Thr
                245                 250                 255
```

```
Arg Ile Arg Asn Asn Phe Asp Cys Thr Pro Ile Met Glu Tyr Ile Lys
            260                 265                 270

Asn Asp Cys Val Thr Gly His Ile Leu Ile Met Leu Leu Asn Trp His
        275                 280                 285

Glu Gln Lys Tyr Gly Lys Leu Gln Lys Glu Gly His His Leu Leu
    290                 295                 300

Tyr Leu Phe Ile Lys His Asn Gln Gly Tyr Gly Ser His Ala Phe Asn
305                 310                 315                 320

Ile Leu Arg Tyr Leu Leu Asp Arg Phe Asp Ile Gln Lys Asp Glu Tyr
            325                 330                 335

Tyr Asn Thr Met Thr Pro Leu His Thr Ala Phe Gln Asn Cys Asn Asn
            340                 345                 350

Asn Val Ala Ser Tyr Leu Val Tyr Ile Gly Tyr Asp Ile Asn Leu Pro
        355                 360                 365

Thr Lys Asp Asp Lys Thr Val Phe Asp Leu Val Phe Glu Asn Arg Asn
    370                 375                 380

Ile Leu Phe Asn Ala Gly Val Ile His Asn Ile Ile His His Arg Leu
385                 390                 395                 400

Lys Val Ser Leu Pro Met Ile Lys Ser Leu Phe Tyr Lys Met Leu Glu
            405                 410                 415

Phe Ser Pro Tyr Asp Asp Tyr Val Lys Lys Ile Ile Ala Tyr Cys
            420                 425                 430

Ile Leu Arg Asp Glu Ser Phe Thr Glu Leu His Ser Lys Phe Cys Leu
            435                 440                 445

Asn Glu Asp Tyr Lys Ser Val Phe Met Lys Asn Ile Ser Phe Asp Lys
    450                 455                 460

Ile Asp Ser Ile Ile Glu Lys Cys Ser Cys Glu Ile Ser Arg Leu Lys
465                 470                 475                 480

Asp Ile Gln Ile Ser Asp Thr Asn Leu Tyr Thr Val Leu Arg Thr Glu
            485                 490                 495

Asp Ile Arg Tyr Arg Thr Tyr Leu Lys Ala Ile His Leu Asp Ser His
            500                 505                 510

Ile Ser Phe Pro Met Tyr Asp Asp Leu Ile Glu Gln Cys His Leu Ser
        515                 520                 525

Met Glu Arg Lys Ser Lys Leu Val Asp Lys Val Leu Asn Lys Leu Lys
    530                 535                 540

Ser Thr Ile Asp Gly Gln Ser Arg Leu Ser Tyr Leu Pro Pro Glu Ile
545                 550                 555                 560

Ile Arg Asn Ile Ile Thr Lys Leu Ser Asp Tyr His Leu Asn Ser Met
            565                 570                 575

Leu Tyr Gly Lys Asn His Tyr Lys Tyr Tyr Thr Glu Phe Arg
            580                 585                 590

<210> SEQ ID NO 8
<211> LENGTH: 587
<212> TYPE: PRT
<213> ORGANISM: Artificial sequence
<220> FEATURE:
<223> OTHER INFORMATION: synthetic

<400> SEQUENCE: 8

Met Asp Glu Met Asp Glu Ile Val Arg Ile Val Arg Asp Ser Met Trp
1               5                   10                  15

Tyr Ile Pro Asn Val Phe Met Asp Asp Gly Lys Asn Glu Gly His Val
            20                  25                  30
```

-continued

```
Ser Val Asn Asn Val Cys His Met Tyr Phe Thr Phe Phe Asp Val Asp
         35                  40                  45

Thr Ser Ser His Leu Phe Lys Leu Val Ile Lys His Cys Asp Leu Asn
     50                  55                  60

Lys Arg Leu Lys Cys Gly Asn Ser Pro Leu His Cys Tyr Thr Met Asn
 65                  70                  75                  80

Thr Arg Phe Asn Pro Ser Val Leu Lys Ile Leu Leu His His Gly Met
                 85                  90                  95

Arg Asn Phe Asp Ser Lys Asp Glu Lys Gly His Ile Pro Leu His His
                100                 105                 110

Tyr Leu Ile His Ser Leu Ser Ile Asp Asn Lys Ile Phe Asp Ile Leu
            115                 120                 125

Thr Asp Thr Ile Asp Asp Phe Ser Lys Ser Ser Asp Leu Leu Leu Cys
        130                 135                 140

Tyr Leu Arg Tyr Lys Phe Asn Gly Ser Leu Asn Tyr Tyr Val Leu Tyr
145                 150                 155                 160

Lys Leu Leu Thr Lys Gly Ser Asp Pro Asn Cys Ala Asp Glu Asp Glu
                165                 170                 175

Leu Thr Ser Leu His Tyr Tyr Cys Lys His Ile Ser Thr Phe Tyr Lys
            180                 185                 190

Ser Asn Tyr Tyr Lys Ser Ser His Thr Lys Met Arg Ala Glu Lys Arg
        195                 200                 205

Phe Ile Tyr Ala Ile Ile Asp Tyr Gly Ala Asn Ile Asn Ala Val Thr
    210                 215                 220

Lys Ile Gly Asn Thr Pro Leu His Thr Tyr Leu Gln Gln Tyr Thr Lys
225                 230                 235                 240

His Ser Pro Arg Val Val Tyr Ala Leu Leu Ser Arg Gly Ala Asp Thr
                245                 250                 255

Arg Ile Arg Asn Asn Leu Asp Cys Thr Pro Ile Met Glu Tyr Ile Lys
            260                 265                 270

Asn Asp Cys Ala Thr Gly His Ile Leu Ile Met Leu Leu Asn Trp His
        275                 280                 285

Glu Gln Lys Tyr Gly Lys Leu Gln Lys Glu Gly Gln His Leu Leu
    290                 295                 300

Tyr Leu Phe Ile Lys His Asn Gln Gly Tyr Gly Ser Tyr Thr Leu Asn
305                 310                 315                 320

Ile Leu Arg Tyr Leu Leu Asn Arg Phe Asp Ile Gln Lys Asp Glu Tyr
                325                 330                 335

Tyr Asn Thr Met Thr Pro Leu His Thr Ala Phe Gln Asn Cys Asn Asn
            340                 345                 350

Asn Val Ala Ser Tyr Leu Val Tyr Ile Gly Tyr Asp Ile Asn Leu Pro
        355                 360                 365

Thr Lys Asp Asp Lys Thr Val Phe Asp Leu Val Phe Glu Asn Arg Asn
    370                 375                 380

Ile Ile Tyr Lys Ala Asp Val Val Asn Asp Ile His His Arg Leu
385                 390                 395                 400

Lys Val Ser Leu Pro Met Ile Lys Ser Leu Phe Tyr Lys Met Ser Glu
                405                 410                 415

Phe Ser Pro Tyr Asp Asp Tyr Val Lys Lys Ile Leu Ala Tyr Cys
            420                 425                 430

Leu Leu Arg Asp Glu Ser Phe Ala Glu Leu His Ser Lys Phe Cys Leu
        435                 440                 445
```

```
Asn Glu Asp Tyr Lys Ser Val Phe Met Lys Asn Ile Ser Phe Asp Lys
        450                 455                 460

Ile Asp Ser Ile Ile Glu Lys Cys Ser Arg Asp Ile Ser Arg Leu Lys
465                 470                 475                 480

Glu Ile Arg Ile Ser Asp Thr Asp Leu Tyr Thr Val Leu Arg Thr Glu
                485                 490                 495

Asp Ile Arg Tyr His Ser Tyr Leu Lys Ala Ile His Ser Asp Ser His
                500                 505                 510

Ile Ser Phe Pro Met Tyr Asp Asp Leu Ile Glu Gln Cys His Leu Ser
            515                 520                 525

Met Glu Arg Lys Ser Lys Leu Val Asp Lys Ala Leu Asn Lys Leu Glu
530                 535                 540

Ser Thr Ile Asp Gly Gln Ser Arg Leu Ser Tyr Leu Pro Pro Glu Ile
545                 550                 555                 560

Met Arg Asn Ile Ile Thr Lys Leu Ser Asp Tyr His Leu Asn Ser Met
                565                 570                 575

Leu Tyr Gly Lys Asn His Tyr Lys Tyr Tyr Pro
                580                 585

<210> SEQ ID NO 9
<211> LENGTH: 578
<212> TYPE: PRT
<213> ORGANISM: Artificial sequence
<220> FEATURE:
<223> OTHER INFORMATION: synthetic

<400> SEQUENCE: 9

Met Asp Thr Ile Ile Asn Ile Val Thr Asp Asn Met Leu Tyr Ile Pro
1               5                   10                  15

Asp Thr Phe Leu Ser Asp Ser Thr Asp Tyr Ile Thr Ile Asp Asn Val
                20                  25                  30

Cys His Met Tyr Phe Ala Phe Phe Asp Val Ile Pro Ser Ser Leu Leu
            35                  40                  45

Phe Lys Leu Thr Leu Lys His Cys Asp Leu Asn Lys Arg Leu Arg Cys
    50                  55                  60

Gly Ile Ser Pro Leu His Cys Tyr Leu Leu Asn Pro Arg Phe Lys Pro
65                  70                  75                  80

Ser Val Leu Lys Ile Leu Leu His His Gly Met Lys Asn Phe Asp Ser
                85                  90                  95

Val Asp Asp Asn Asn Arg Ile Pro Leu His Tyr Tyr Leu Ile Arg Ala
                100                 105                 110

Asn Val Ile Asp Asn Lys Ile Phe Asp Met Ile Thr Asp Gly Ile Ser
            115                 120                 125

Phe Arg Lys Tyr Ser Asn Leu Leu Leu Cys Tyr Leu Lys Tyr Asn Tyr
    130                 135                 140

Asn Lys Gln Leu Asn Tyr Tyr Ile Leu Tyr Lys Leu Leu Glu Gly Ser
145                 150                 155                 160

Asp Pro Asn Cys Ile Asp Asn Asp Gly Leu Thr Pro Leu His Tyr Tyr
                165                 170                 175

Cys Arg Tyr Ile Ser Ser Phe His Glu Arg Asn Tyr Tyr Ala Ser Lys
                180                 185                 190

Ser Tyr Thr Lys Met Asn Ala Glu Lys Arg Phe Ile Asn Thr Ile Val
            195                 200                 205

Lys Tyr Gly Ala Asp Ile Asn Ala Val Thr Lys Ile Gly Asn Thr Pro
    210                 215                 220
```

Leu His Thr Tyr Leu Arg Glu Tyr Thr Asn His Ser Pro Arg Val Val
225                 230                 235                 240

Tyr Thr Leu Leu Ser Leu Gly Ala Asp Thr Arg Ile Cys Asn Lys Tyr
            245                 250                 255

Gly His Thr Pro Ile Met Glu Tyr Val Lys Cys Asp Tyr Ala Thr Gly
            260                 265                 270

Tyr Ile Leu Ile Met Leu Leu Asn Trp His Glu Arg Lys Tyr Gly Lys
        275                 280                 285

Ile Gln Lys Glu Glu Gly Gln Asn Ile Leu His Leu Phe Ile Lys His
    290                 295                 300

Asn Arg Ser His Ser Leu Asn Ile Leu Ile Tyr Leu Leu Asp Lys Phe
305                 310                 315                 320

Asp Ile Gln Ile Asp Glu Tyr Tyr Asn Thr Met Thr Pro Leu His Val
            325                 330                 335

Ala Phe Gln Asn Cys Asn Ser Lys Ile Ala Ser Tyr Leu Val Tyr Ile
            340                 345                 350

Gly Tyr Asp Ile Asn Leu Pro Thr Lys Asp Gly Lys Thr Val Ile Asp
        355                 360                 365

Leu Val Phe Glu Asn Arg Ser Ile Ile Phe Lys Ala Asp Ile Ile Asn
370                 375                 380

Asp Ile Ile Lys His Arg Leu Lys Val Ser Leu Ser Ile Ile Glu Ser
385                 390                 395                 400

Leu Leu Tyr Arg Met Ser Asp Phe Ala Ser Tyr Asp Tyr Tyr Leu
            405                 410                 415

Lys Lys Ile Ile Ala Tyr Cys Ile Leu Arg Asp Glu Ala Phe Val Glu
            420                 425                 430

Arg Tyr Arg Lys Leu Cys Leu Asn Pro Glu Tyr Arg Gly Ser Phe Ile
        435                 440                 445

Lys Asn Ile Ser Phe Asp Val Val Asp Ser Ile Ile Ser Lys Cys Ser
    450                 455                 460

Asn Glu Ile Ser His Leu Lys Asp Ile Arg Leu Gly Asp Val Asp Leu
465                 470                 475                 480

Tyr Thr Val Leu Arg Thr Asp Asp Ser Arg Tyr Tyr Ser His Ile Glu
            485                 490                 495

Asn Ile Tyr Leu Asn Arg Arg Leu Ser Phe Pro Met Tyr Asp Ile Ile
            500                 505                 510

Ile Glu Glu Cys Tyr Ile Tyr Met Lys Asn Lys Asn Lys Leu Ile Asn
        515                 520                 525

Asp Ala Met Tyr Lys Leu Gln Ser Ile Ile Asp Gly Gln Ser Ile Leu
530                 535                 540

Tyr Lys Leu Pro Pro Glu Ile Leu Tyr Glu Ile Leu Ser Lys Leu Ser
545                 550                 555                 560

Val Tyr His Leu Asn Asn Met Leu Tyr Gly Lys Lys His Tyr Lys Asn
            565                 570                 575

Tyr His

<210> SEQ ID NO 10
<211> LENGTH: 640
<212> TYPE: PRT
<213> ORGANISM: Artificial sequence
<220> FEATURE:
<223> OTHER INFORMATION: synthetic

<400> SEQUENCE: 10

Met Leu Met Trp Met Asp Ile Thr Lys Ser Pro Ser Lys Met Ile Lys

-continued

```
1               5                   10                  15
His Val Tyr Phe Ile Cys Gln Pro Leu Leu Lys Asn Ile Val Leu Phe
                20                  25                  30
Cys Phe Leu Phe Leu Ser His Ile Ser Asn Tyr Glu Lys Val Asn Asp
                35                  40                  45
Glu Met Tyr Glu Met Gly Glu Met Asp Glu Ile Val Ser Ile Val Ser
                50                  55                  60
Asp Ser Met Trp Phe Ile Pro Asn Val Phe Met Asp Asn Gly Glu Asn
 65                 70                  75                  80
Glu Gly His Val Ser Val Asn Asn Val Cys His Met Tyr Phe Thr Phe
                85                  90                  95
Phe Asp Val Asp Thr Ser Ser His Leu Phe Lys Leu Val Ile Lys His
                100                 105                 110
Cys Asp Leu Asn Lys Gln Leu Lys Cys Gly Met Ser Pro Leu His Cys
                115                 120                 125
Tyr Val Met Asn Thr Arg Phe Lys Pro Ser Val Leu Lys Ile Leu Leu
                130                 135                 140
His Asn Gly Val Asn Asn Phe Asp Asn Thr Asp Asn Lys Gly His Ile
145                 150                 155                 160
Pro Leu His His Tyr Leu Ile His Ser Leu Ser Ile Asp Asn Lys Val
                165                 170                 175
Phe Asp Ile Leu Thr Asp Pro Ile Asp Asp Phe Ser Lys Ser Ser Asp
                180                 185                 190
Leu Leu Leu Cys Tyr Leu Arg Tyr Lys Phe Asn Gly Arg Leu Asn Tyr
                195                 200                 205
Tyr Val Leu Tyr Lys Leu Leu Thr Lys Gly Ser Asp Pro Asn Cys Val
210                 215                 220
Asp Glu Asp Gly Leu Thr Ser Leu His Tyr Tyr Cys Lys His Ile Ser
225                 230                 235                 240
Ala Phe His Glu Ser Asn Tyr Tyr Lys Ser Lys Ser Tyr Thr Lys Met
                245                 250                 255
Arg Ala Glu Lys Arg Phe Ile Tyr Thr Ile Ile Asp His Gly Ala Asn
                260                 265                 270
Ile Asn Ala Val Thr Lys Ile Gly Asn Thr Pro Leu His Thr Tyr Leu
                275                 280                 285
Gln Gln Tyr Thr Lys His Ser Pro Arg Val Val Tyr Ala Leu Leu Ser
                290                 295                 300
Arg Gly Ala Asp Thr Arg Ile Arg Asn Asn Leu Asp Cys Thr Pro Ile
305                 310                 315                 320
Met Glu Tyr Ile Lys Asn Asp Cys Ala Thr Gly His Ile Leu Ile Met
                325                 330                 335
Leu Leu Asn Trp His Glu Gln Lys Tyr Gly Lys Leu Gln Lys Glu Glu
                340                 345                 350
Gly His His Leu Leu Tyr Ile Phe Ile Lys His Asn Gln Gly Tyr Gly
                355                 360                 365
Ser His Ala Phe Asn Ile Leu Arg Tyr Leu Leu Asp Arg Phe Asp Ile
                370                 375                 380
Gln Lys Asp Glu Tyr Tyr Asn Thr Met Thr Pro Leu His Thr Ala Phe
385                 390                 395                 400
Gln Asn Cys Asn Asn Asn Val Ala Ser Tyr Leu Val Tyr Ile Gly Tyr
                405                 410                 415
Asp Ile Asn Leu Pro Thr Lys Asp Asp Lys Thr Val Phe Asp Leu Val
                420                 425                 430
```

```
Phe Glu Asn Arg Asn Ile Leu Tyr Asn Ala Asp Val Ile His Asp Ile
            435                 440                 445

Ile His His Arg Leu Lys Val Ser Leu Pro Met Ile Lys Ser Leu Phe
450                 455                 460

Tyr Lys Met Ser Glu Phe Ser Pro Tyr Asn Asp Tyr Val Lys Lys
465                 470                 475                 480

Ile Ile Ala Tyr Cys Leu Leu Arg Asp Glu Ser Phe Ala Glu Leu His
            485                 490                 495

Ser Lys Phe Cys Leu Asn Glu Asp Tyr Lys Ser Val Phe Met Lys Asn
            500                 505                 510

Ile Ser Phe Asp Lys Ile Asp Ser Ile Ile Glu Lys Cys Ser Trp Asp
            515                 520                 525

Ile Ser Arg Leu Lys Asp Ile Arg Ile Ser Asp Thr Asp Leu Tyr Thr
            530                 535                 540

Val Leu Arg Thr Glu Asp Ile Arg Tyr Arg Thr Tyr Leu Glu Ala Ile
545                 550                 555                 560

His Ser Asp Ser His Ile Ser Phe Pro Met Tyr Asp Leu Ile Glu
            565                 570                 575

Gln Cys His Leu Ser Met Glu Arg Lys Ser Lys Leu Val Asp Lys Ala
            580                 585                 590

Leu Asn Lys Leu Glu Ser Ile Ile Asp Gly Gln Ser Arg Leu Ser Tyr
            595                 600                 605

Leu Pro Pro Glu Ile Ile Arg Asn Ile Ile Thr Lys Leu Ser Asp Tyr
            610                 615                 620

His Leu Asn Ser Met Leu Tyr Gly Lys Asn His Tyr Lys Tyr Tyr Pro
625                 630                 635                 640

<210> SEQ ID NO 11
<211> LENGTH: 591
<212> TYPE: PRT
<213> ORGANISM: Artificial sequence
<220> FEATURE:
<223> OTHER INFORMATION: synthetic

<400> SEQUENCE: 11

Met Tyr Glu Met Gly Glu Met Asp Glu Ile Val Ser Ile Val Ser Asp
1               5                   10                  15

Ser Met Trp Phe Ile Pro Asn Val Phe Met Asn Asp Glu Asn Glu
            20                  25                  30

Gly His Val Ser Val Asn Asn Val Cys His Met Tyr Phe Thr Phe Phe
            35                  40                  45

Asp Val Asp Thr Ser Ser His Leu Phe Lys Leu Val Ile Lys His Cys
50                  55                  60

Asp Leu Asn Lys Gln Leu Lys Cys Gly Met Ser Pro Leu His Cys Tyr
65                  70                  75                  80

Val Met Asn Thr Arg Phe Lys Pro Ser Val Leu Lys Ile Leu Leu His
            85                  90                  95

Asn Gly Val Asn Asn Phe Asp Asn Lys Asp Asn Lys Gly His Ile Pro
            100                 105                 110

Leu His His Tyr Leu Ile His Ser Leu Ser Ile Asp Asn Lys Val Phe
            115                 120                 125

Asp Ile Leu Thr Asp Pro Ile Asp Asp Phe Ser Lys Ser Ser Asp Leu
130                 135                 140

Leu Leu Cys Tyr Leu Arg Tyr Lys Phe Asn Gly Arg Leu Asn Tyr Tyr
145                 150                 155                 160
```

```
Val Leu Tyr Lys Leu Leu Thr Lys Gly Ser Asp Pro Asn Cys Val Asp
            165                 170                 175

Glu Asp Gly Leu Thr Ser Leu His Tyr Tyr Cys Lys His Ile Ser Ala
            180                 185                 190

Phe His Glu Ser Asn Tyr Tyr Lys Ser Lys Ser Tyr Thr Lys Met Arg
            195                 200                 205

Ala Glu Lys Arg Phe Ile Tyr Thr Ile Ile Asp His Gly Ala Asn Ile
210                 215                 220

Asn Ala Val Thr Asn Ile Gly Asn Thr Pro Leu His Thr Tyr Leu Gln
225                 230                 235                 240

Gln Tyr Thr Lys His Ser Pro Arg Val Val Tyr Ala Leu Leu Ser Arg
            245                 250                 255

Gly Ala Asp Thr Arg Ile Arg Asn Asn Leu Asp Cys Thr Pro Ile Met
            260                 265                 270

Glu Tyr Ile Lys Asn Asp Cys Ala Thr Gly His Ile Leu Ile Met Leu
            275                 280                 285

Leu Asn Trp His Glu Gln Lys Tyr Gly Lys Leu Gln Lys Glu Glu Gly
            290                 295                 300

His His Leu Leu Tyr Ile Phe Ile Lys His Asn Gln Gly Tyr Gly Ser
305                 310                 315                 320

His Ala Phe Asn Ile Leu Arg Tyr Leu Leu Asp Arg Phe Asp Ile Gln
                325                 330                 335

Lys Asp Glu Tyr Tyr Asn Thr Met Thr Pro Leu His Thr Ala Phe Gln
            340                 345                 350

Asn Cys Asn Asn Asn Val Ala Ser Tyr Leu Val Tyr Ile Gly Tyr Asp
            355                 360                 365

Ile Asn Leu Pro Thr Lys Asp Asp Lys Thr Val Phe Asp Leu Val Phe
            370                 375                 380

Glu Asn Arg Asn Ile Leu Tyr Asn Ala Asp Val Ile His Asp Ile Ile
385                 390                 395                 400

His His Arg Leu Lys Val Ser Leu Pro Met Ile Lys Ser Leu Phe Tyr
            405                 410                 415

Lys Met Ser Glu Phe Ser Pro Tyr Asp Asp Tyr Val Lys Lys Ile
            420                 425                 430

Ile Ala Tyr Cys Ile Leu Arg Asp Glu Ser Phe Ala Glu Leu His Ser
            435                 440                 445

Lys Phe Cys Leu Asn Glu Asp Tyr Lys Ser Val Phe Met Lys Asn Ile
            450                 455                 460

Ser Phe Asp Lys Ile Asp Ser Ile Ile Glu Lys Cys Ser Trp Asp Ile
465                 470                 475                 480

Ser Arg Leu Lys Asp Ile Arg Ile Ser Asp Thr Asp Leu Tyr Thr Val
            485                 490                 495

Leu Arg Thr Glu Asp Ile Arg Tyr Arg Ser Tyr Leu Glu Ala Ile His
            500                 505                 510

Leu Asp Ser His Ile Ser Phe Pro Met Tyr Asp Asp Leu Ile Glu Gln
            515                 520                 525

Cys His Leu Ser Met Glu Arg Lys Ser Lys Leu Val Asp Lys Ala Leu
            530                 535                 540

Asn Lys Leu Glu Ser Thr Ile Asp Gly Gln Cys Arg Leu Ser Tyr Leu
545                 550                 555                 560

Pro Pro Glu Ile Ile Arg Asn Ile Ile Thr Lys Leu Ser Asp Tyr His
            565                 570                 575
```

```
Leu Asn Ser Met Leu Tyr Gly Lys Asn His Tyr Lys Tyr Tyr Pro
                580                 585                 590

<210> SEQ ID NO 12
<211> LENGTH: 579
<212> TYPE: PRT
<213> ORGANISM: Artificial sequence
<220> FEATURE:
<223> OTHER INFORMATION: synthetic

<400> SEQUENCE: 12

Met Asp Asp Ile Val Asn Met Val Thr Ala Asn Met Trp Tyr Ile Pro
1               5                   10                  15

Tyr Thr Leu Leu Ser Asp Asn Thr Asp Cys Ile Thr Ile Asn Asn Ala
                20                  25                  30

Cys His Met Tyr Phe Ala Phe Phe Asp Val Val Pro Ser Ser Arg Leu
            35                  40                  45

Phe Lys Leu Thr Leu Lys His Cys Asp Leu Asn Lys Arg Leu Arg Cys
    50                  55                  60

Gly Val Ser Pro Leu His Cys Tyr Leu Leu Asn Pro Arg Phe Arg Pro
65                  70                  75                  80

Ser Val Leu Lys Ile Leu Leu His Asn Gly Met Lys Asn Phe Asp Ser
                85                  90                  95

Glu Asp Asp Asn His Arg Ile Pro Leu His Tyr Tyr Leu Ile Arg Ala
                100                 105                 110

Asp Ile Ile Gly Asn Lys Ile Phe Asp Met Ile Thr Asp Gly Val Ser
            115                 120                 125

Ile Arg Lys His Lys Asp Leu Leu Cys Tyr Leu Lys Tyr Lys Tyr
    130                 135                 140

Gly Lys Gln Leu Asn Tyr Tyr Val Leu Tyr Lys Leu Leu Thr Glu Gly
145                 150                 155                 160

Ser Asp Pro Asn Cys Val Asp Asn Asp Gly Leu Ala Pro Leu His Tyr
                165                 170                 175

Tyr Cys Arg His Ile Ser Met Phe His Glu Arg Asn Asn Tyr Thr Ser
            180                 185                 190

Thr Pro Tyr Thr Lys Met Asn Ala Glu Lys Arg Phe Ile Asn Thr Ile
    195                 200                 205

Val Lys Tyr Gly Ala Asp Ile Asn Ala Val Thr Asn Ile Gly Asn Thr
210                 215                 220

Pro Leu His Thr Tyr Leu Arg Glu Tyr Thr Lys His Ser Pro Arg Val
225                 230                 235                 240

Val Tyr Ser Leu Leu Ser Leu Gly Ala Asp Thr Arg Ile Arg Asn Lys
                245                 250                 255

Tyr Gly His Thr Pro Ile Met Gln Tyr Val Lys Cys Asp Tyr Ala Thr
            260                 265                 270

Gly Tyr Ile Leu Ile Met Leu Leu Asn Trp His Glu Arg Lys Tyr Gly
    275                 280                 285

Asn Ile Gln Lys Glu Glu Gly Gln Asn Ile Leu His Leu Phe Ile Lys
290                 295                 300

His Asn Arg Gly His Asn Leu Asn Ile Leu Tyr Leu Leu Asp Lys
305                 310                 315                 320

Phe Asp Ile His Thr Asp Glu Tyr Tyr Asn Thr Met Thr Pro Leu His
                325                 330                 335

Ile Ala Phe Gln Asn Cys Asn Ser Ala Ile Ala Ser Tyr Leu Val Tyr
            340                 345                 350
```

Ile Gly His Asp Ile Asn Leu Pro Thr Lys Asp Gly Lys Thr Val Ile
            355                 360                 365

Asp Leu Val Phe Glu Asn Ser Ser Ile Ile Phe Lys Ala Asp Ser Ile
370                 375                 380

Asn Asp Ile Ile Lys His Arg Leu Lys Val Ser Leu Ser Ile Ile Lys
385                 390                 395                 400

Ser Leu Leu Tyr Lys Ile Ser Asp Phe Ala Ser Tyr Asp Asp Tyr Tyr
                405                 410                 415

Leu Lys Lys Ile Ile Ala Tyr Cys Val Leu Arg Asp Glu Thr Phe Val
            420                 425                 430

Glu Arg Tyr Arg Lys Asn Cys Leu Asn Thr Glu Tyr Arg Glu Ser Phe
        435                 440                 445

Ile Lys Asn Ile Ser Phe Asp Leu Val Asp Ser Ile Ile Thr Arg Cys
    450                 455                 460

Ser Asn Glu Ile Ser Arg Leu Lys Asp Ile Arg Leu Gly Asp Val Asp
465                 470                 475                 480

Leu Tyr Thr Val Leu Arg Thr Asp Asn Ile Arg Tyr Tyr Ser His Ile
                485                 490                 495

Glu Ser Ile His Leu Asn Arg His Ile Ser Phe Pro Met Tyr Asp Ile
            500                 505                 510

Ile Val Glu Glu Cys Tyr Ile Ser Met Arg Asn Lys Asn Lys Leu Ile
        515                 520                 525

Asn Asp Ala Val His Lys Val Gln Ser Ile Asp Gly Glu Ser Arg
    530                 535                 540

Leu Ser Lys Leu Pro Pro Glu Ile Val Tyr Glu Ile Ile Thr Lys Leu
545                 550                 555                 560

Asn Glu Tyr His Leu Asn Asn Ile Leu Tyr Gly Lys Lys His Tyr Lys
                565                 570                 575

Tyr Tyr His

<210> SEQ ID NO 13
<211> LENGTH: 21
<212> TYPE: DNA
<213> ORGANISM: Artificial sequence
<220> FEATURE:
<223> OTHER INFORMATION: synthetic

<400> SEQUENCE: 13
aggtgtccca agaagctgt a                                          21

<210> SEQ ID NO 14
<211> LENGTH: 21
<212> TYPE: DNA
<213> ORGANISM: Artificial sequence
<220> FEATURE:
<223> OTHER INFORMATION: synthetic

<400> SEQUENCE: 14
atgtctggac ccattccttc t                                         21

<210> SEQ ID NO 15
<211> LENGTH: 24
<212> TYPE: DNA
<213> ORGANISM: Artificial sequence
<220> FEATURE:
<223> OTHER INFORMATION: synthetic

<400> SEQUENCE: 15
gagcttgagt gtgacgcccc cagg                                      24

<210> SEQ ID NO 16
<211> LENGTH: 25
<212> TYPE: DNA
<213> ORGANISM: Artificial sequence
<220> FEATURE:
<223> OTHER INFORMATION: synthetic

<400> SEQUENCE: 16
gttagccttg cctttgttca gtatc                                         25

<210> SEQ ID NO 17
<211> LENGTH: 22
<212> TYPE: DNA
<213> ORGANISM: Artificial sequence
<220> FEATURE:
<223> OTHER INFORMATION: synthetic

<400> SEQUENCE: 17
ttgctcctca cgttcagatt tc                                            22

<210> SEQ ID NO 18
<211> LENGTH: 22
<212> TYPE: DNA
<213> ORGANISM: Artificial sequence
<220> FEATURE:
<223> OTHER INFORMATION: synthetic

<400> SEQUENCE: 18
ggagacacgc gtcctataac ta                                            22

<210> SEQ ID NO 19
<211> LENGTH: 20
<212> TYPE: DNA
<213> ORGANISM: Artificial sequence
<220> FEATURE:
<223> OTHER INFORMATION: synthetic

<400> SEQUENCE: 19
cggagaggag acttcacaga                                               20

<210> SEQ ID NO 20
<211> LENGTH: 20
<212> TYPE: DNA
<213> ORGANISM: Artificial sequence
<220> FEATURE:
<223> OTHER INFORMATION: synthetic

<400> SEQUENCE: 20
ccagtttggt agcatccatc                                               20

<210> SEQ ID NO 21
<211> LENGTH: 22
<212> TYPE: DNA
<213> ORGANISM: Artificial sequence
<220> FEATURE:
<223> OTHER INFORMATION: synthetic

<400> SEQUENCE: 21
caaacccaga attgttctcc tt                                            22

<210> SEQ ID NO 22
<211> LENGTH: 21
<212> TYPE: DNA
<213> ORGANISM: Artificial sequence
<220> FEATURE:

-continued

```
<223> OTHER INFORMATION: synthetic

<400> SEQUENCE: 22
atgtggtctt cctgaatccc t                                              21

<210> SEQ ID NO 23
<211> LENGTH: 20
<212> TYPE: PRT
<213> ORGANISM: Artificial sequence
<220> FEATURE:
<223> OTHER INFORMATION: synthetic

<400> SEQUENCE: 23

Cys Asp Tyr His Leu Lys Ser Met Leu Tyr Gly Lys Asn His Tyr Lys
1               5                   10                  15

His Tyr Pro Tyr
            20
```